(12) United States Patent
Steiner et al.

(10) Patent No.: US 11,083,726 B2
(45) Date of Patent: Aug. 10, 2021

(54) METHODS AND COMPOSITIONS FOR TREATING VASOMOTOR SYMPTOMS

(71) Applicant: UNIVERSITY OF WASHINGTON THROUGH ITS CENTER FOR COMMERCIALIZATION, Seattle, WA (US)

(72) Inventors: Robert A. Steiner, Seattle, WA (US); Charles Chavkin, Seattle, WA (US); Donald K. Clifton, Seattle, WA (US); Susan Reed, Seattle, WA (US); Victor Navarro, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 16/114,661

(22) Filed: Aug. 28, 2018

(65) Prior Publication Data

US 2019/0255037 A1 Aug. 22, 2019
US 2021/0030745 A9 Feb. 4, 2021

Related U.S. Application Data

(63) Continuation of application No. 15/586,762, filed on May 4, 2017, now abandoned, which is a continuation of application No. 15/226,408, filed on Aug. 2, 2016, now abandoned, which is a continuation of application No. 14/439,585, filed as application No. PCT/US2013/072772 on Dec. 3, 2013, now abandoned.

(60) Provisional application No. 61/732,586, filed on Dec. 3, 2012.

(51) Int. Cl.

| A61K 31/485 | (2006.01) |
|---|---|
| A61K 45/06 | (2006.01) |
| A61K 31/439 | (2006.01) |
| A61K 31/40 | (2006.01) |
| A61K 31/47 | (2006.01) |

(52) U.S. Cl.
CPC ............ *A61K 31/485* (2013.01); *A61K 31/40* (2013.01); *A61K 31/439* (2013.01); *A61K 31/47* (2013.01); *A61K 45/06* (2013.01)

(58) Field of Classification Search
None
See application file for complete search history.

(56) References Cited

U.S. PATENT DOCUMENTS 10,052,317 B2 * 8/2018 Dhillo ................ A61K 31/4545
2002/0016283 A1 2/2002 Guttuso et al.

FOREIGN PATENT DOCUMENTS

| WO | 2004/054511 A2 | 7/2004 |
|---|---|---|
| WO | 2016/033163 | 3/2015 |

OTHER PUBLICATIONS

Grady et al. ("Discontinuation of postmenopausal hormone therapy" The American Journal of Medicine; vol. 118, Issue 12, Supplement 2, 163-165, 2005).*
Ambach, et al., "Blood Supply of the Rat Hypothalamus. IV. Retrochiasmatic Area, Median Erminece, Arcuate Nucleus," Acta Morphologica Acad Sci Hung, vol. 24, pp. 93-119, 197.
Ayers, "Effectiveness of group and self-help cognitive behavior therapy in reducing problematic menopausal hot flushes and night sweats (MENOS 2): a randomized controlled trial," Menopuase: The Journal of the North American Menopause Society, vol. 19, No. 7, pp. 749-759, 2012.
Bardia, et al., "Pilot evaluation of aprepitant for the treatment of hot flashes," Supportive Cancer Therapy, vol. 3, No. 4. pp. 24-246, 2006.
Benarroch, "Thermoregulation Recent concepts and remaining questions," Neurology, pp. 1293-1297, 2007.
Burke, et al., "Coexpression of Dynorphin and Neurokinin B Immunoreactivity in the Rat Hypothalamus: Morphologic Evidence of Interrelated Function Within the Arcuate Nucleus," The Journal of Comparative Neurology, vol. 498, pp. 712-726, 2006.
Carpenter, et al., "Laboratory and ambulatory evaluation of vasomotor symptom monitors from the Menopause Strategies Finding Lasting Answers for Symptoms and Health network," Menopause: The Journal of the North American Menopause Society, vol. 19, No. 6, 2011.
Carpenter, et al., "Other complementary and alternative medicine modalities: acupuncture, magnets, reflexology, and homeopathy," The American Journal of Medicine, vol. 118, No. 12B, pp. 109S-117S, 2005.
Charig, et al., "Long-Term Side Effect of Orchiectomy in Treatment of Prostatic Carcinoma," Urology, vol. 33, No. 3, pp. 175- 178, 1989.
Dacks, et al., "Activation of Neurokinin 3 Receptors in the Median Preoptic N~cleus Decreases Core Temperature in the Rat," Endocrinology, vol. 152, No. 12, 2011.
Deecher, et al., "Understanding the pathophysiology of vasomotor symptoms (hot flushes and night sweats) that occur in perimenopause, menopause, and postmenopause life stages," Arch Womens Men Health, vol. 10, pp. 247-257, 2007.
Engstrom, et al., "Hot Flash Experience in Men With Prostate Cancer: A Concept Analysis," Oncology Nursing Forum, vol. 32, No. 5, pp. 1043-1048, 2005.
Feng et al., "Central Depressor Effect of U-50488h A Highly Selective Kappa Opioid Agonist", ACTA Physiolica Sinica, vol. 39, No. 3, pp. 305-309, 1987.
Freedman, "Pathophysiology and Treatment of Menopausal Hot Flashes," Seminars in Reproductive Medicine, vol. 23, No. 2, pp. 117-125, 2005.

(Continued)

*Primary Examiner* — James H Alstrum-Acevedo
*Assistant Examiner* — Tara L Martinez
(74) *Attorney, Agent, or Firm* — McDonnell Boehnen Hulbert & Berghoff LLP

(57) ABSTRACT

The present disclosure is generally directed to compositions and methods for treating or limiting development of vasomotor symptoms in a subject.

1 Claim, 2 Drawing Sheets

(56) References Cited

OTHER PUBLICATIONS

Freeman, et al., "Efficacy of Escitalopram for Hot Flashes in Healthy Menopausal Women," JAMA, vol. 305, No. 3, pp. 267-274, 2011.

Fry, et al., "NK3 receptors in the feline nucleus tractus solitaries are not involved with the muscle pressor response," Neuropeptides, vol. 35, No. 3-4, pp. 154-161, 2001.

Gallo et al., "Kappa-Opioid Receptor Involvement in the Regulation of Pulsatile Luteinizing Hormone Release During Early Pregnancy in the Rat," Jounal of Neuroendocrinology, vol. 2, No. 5, 1990.

Gilbeau, et al.,"Dynorphin Effects on Plasma Concentrations of Anterior Pituitary Hormones in the Nonhuman Primate," The Journal of Phrmacology and Experimental Therapeutics, vol. 228, No. 3, pp. 974-977, 1986.

Gottsch, et al., "A Role for Kisspeptins in the Regulation of Gonadotropin Secretion in the Mouse," Endocrinology, vol. 145, No. 9, pp. 4073-4077, 2004.

Han, et al., Activation of Gonadotropin-Releasing Hormone Neurons by Kisspeptin as a Neuroendocrine Switch for the Onset of Puberty, The Journal of Neuroscience, vol. 25, No. 49, pp. 11349-11356, 2005.

Hrabovszky, et al., "The kisspeptin system of the human hypothalamus: sexual dimorphism and relationship with gonadotropin-releasinghormone and neurokinin B neurons," European Journal of Neuroscience, vol. 31, pp. 1984-1998, 2010.

Hrabovszky, et al., "Sexual dimorphism of kisspeptin and neurokinin B immunoreactive neurons in the infundibular nucleus of aged men and women," Endocrinology, vol. 2, No. 80, 2011.

Karling, et al,. "Prevalence arid Duration of Hot Flushes After Surgical or Medical Castration in Men with Prostatic Carcinoma," the Journal of Urology, vol. 152, pp. 1170-1173, 1994.

Keen, et al., "An increase in Kisspeptin-54 Release Occurs with the Pubertal Increase in Luteinizing Hormone-Releasing Hormone-1 Release in the Stalk-Median Eminence of Female Rhesus Monkeys in Vivo," Endocrinology, vol. 149, No. 8, pp. 4151-4157, 2008.

Kinoshita, et al., "Suppresive Effecti of Dynorphin-(1-13) on Luteinizing Hormone Release in Conscious Castrated Rats," Life Sciences, vol. 30, pp. 1915-1919, 1982.

Krajewski, et al., "Forebrain Projections of Arcuate Neurokinin B Neurons Demonstrated by Anterograde Tract-Tracing and Monosodium Glutamate Lesions in the Rat," Neuroscience, vol. 166, No. 2, pp. 680-697, 2010.

Kronenberg, "Hot Flashes: Phenomenology, Quality of Life, and Search for Treatment Options," Experimental Gerontology, vol. 29, No. 3/4, pp. 319-336, 1994.

Loprinzi, et al., "A phase III randomized, double-blind, placebo-controlled trial of gabapentin in the management of hot flashes in men (N00CB)," Annals of Oncology, vol. 20, pp. 542-549, 2009.

MacLennan, "Oral oestrogen and combined oestrogen/progestogen therapy versus placebo for hot flushes (Review)," The Chochrane Collabration 2004.

Maeda, et al., "Neurobiological mechanisms underlying GnRH pulse generation by the hypothalamus," Brain Research, pp. 103-115, 2010.

Meldrum, et al., "Elevations in skin temperature of the finer as an objective index of postmenopausal hot flashes: Standardization of the technique," Am J Obster Gynecol, vol. 135, No. 6, pp. 713-717, 1979.

Mittelman-Smith, et al, "Role for kisspeptin/neurokinin B/dynorphin (KNDy) neurons in cutaneous vasodilation and the estrogen modulation of body temperature," PNAS, vol. 109, No. 48, pp. 19846-19851, 2012.

Mom, et al., "Hot flushes in breast cancer patients," Critical Reviews in Oncology/Hematology, vol. 57, pp. 63-77, 2006.

Nachtigali, "Nonhormonal treatment of hot flashes—a viable alternative?" Endocrinology, vol. 6, pp. 66-67, 2010.

Navarro, et al., "Regulation of Gonadotropin-Releasing Hormone Secretion by Kisspeptin/Dynorphin/Neurokinin B Neurons in the Arcuate Nucleus of the Mouse," The Journal of Neuroscience, vol. 29, No. 38, 2009.

NIH Conference, "National Institutes of Health State-of-the-Science Conference Statement: Management of Menopause-Related Symptoms," Annals of INternal Medicine, vol. 142, No. 12, pp. 1003-1014, 2005.

Notelovitz, et al., "Initial 17b-Estradiol Dose for Treating Vasomotor Symptoms," Obstetrics & Gynocology, vol. 95, No. 5, pp. 726-731, 2000.

Ohkura, et al., "Gonadotrophin-Releasing Hormone Pulse Generator Activity in the Hypothalamus of the Goat," Journal of Neuroendocrinology, vol. 21, pp. 813-821, 2009.

Pachman, et al., "Management of menopuse-associated vasomotor symptoms: Current treatment options, challenges and future directions," International Journal of Women's Health, pp. 123-135, 2010.

Palkovits, et al., "Stress-induced Activation of Neurons in the Ventromedial Arcuate Nucleus: A Blood-Brain-CSF Interface of the Hypothalamus," Stress, pp. 57-63, 2008.

PCT/US2013/072772 International Search Report and Written Opinion, dated 2014.

Ramaswamy, et al., "Neurokinin B Stimulates GnRH Release in the Male Monkey (*Macaca mulatta*) and Is Colocalized with Kisspeptin in the Arcuate Nucleus," Endocrinology, vol. 151, No. 9, pp. 4494-4503, 2010.

Rance, et al., "Neurokinin B Stimulates GnRH Release in the Male Monkey (*Macaca mulatta*) and Is Colocalized with Kisspeptin in the Arcuate Nucleus," Peptides, vol. 30, pp. 111-122, 2009.

Rance, et al., Modulation of body temperature and LH secretion by hypothalamic KNDy (kisspeptin, neurokinin B and dynorphin) neurons: A novel hypothesys on the mechanism of hot flushes,: Frontiers in Neuroendocrinology, vol. 34, No. 3, pp. 211-227, 2013.

Reed, et al., "Night sweats, sleep disturbance, and depression associated with diminished libido in late menopausal transition and early postmenopause: baseline data for the Herbal Alternatives for Menopause Trial (HALT)," American Journal of Obstetrics & Gynecology, pp. 593-535, 2007.

Rometo, et al., "Hypertrophy and Increased Kisspeptin Gene Expressionin the Hypothalamic Infundibular Nucleus of Postmenopausal Women and Ovariectomized Monkeys," The Journal of Clinical Endocrinology & Metabolism, vol. 92 (7):2744-2750.

Roseweir, et al, Discovery of Potent Kissdxcapeptin Antagonists Delineate Physiological Mechanisms of Gonadotropin Regulation, The Journal of Neuroscience, vol. 29, No. 12, pp. 3920-3929, 2009.

Schmidt, "The 2012 Hormone Therapy Position Statement of the North American Menopause Society," Menopause, vol. 19, No. 13, pp. 257-271, 2012.

Shaver, et al., "Morphology and Function of Capillary Networks, in Subregions of Rat Tuber Cinereum," Cell tissue Res, vol. 267, pp. 437-448, 1992.

Sieras, et al., "Nonhormonal Management of Hot Flashes for Women on Risk Reduction Therapy," J Natl Compr Can Netw, vol. 8, No. 10, pp. 1171-1179, 2010.

Smith, et al.,"Regulation of Kiss1 Gene Expression in the Brain of the Female Mouse," Endocrinology, vol. 146, No. 9, pp. 3686-3692, 2005.

Sturdee, "The menopausal hot flush—Anything new?" Maturitas, vol. 60, pp. 42-49, 2008.

Tataryn, et al., "LH, FSH and Skin GTemperature During the Menopausal Hot Flash," Journal of Clinical Endocrinology and Metabolism, vol. 43, No. 1, pp. 152-154, 1979.

Utian, "Estrogen and progestogen use in postmenopausal women: Jul. 2008 position statement of the North American Menopause Society," Menopause: The Journal of the North American Menopause Society, vol. 15, No. 4, pp. 584-603, 2008.

Wakabayashi, et al., "Neurokinin B and Dynorphin A in Kisspeptin Neurons of the Arcuate Nucleus Participate in Generation of Periodic Oscillation of Neural Activity Driving Pulsatile Gonadotropin-Releasing Hormone Secretion in the Goat," The Journal of Neuroscience, vol. 30, No. 8, pp. 3124-3132, 2010.

(56) References Cited

OTHER PUBLICATIONS

Yeo, et al., "Projections of Arcuate Nucleus and Rostral Periventricular Kisspeptin Neurons in the Adult Female Mouse Brain," Endocrinology, vol. 152, No. 6, pp. 2387-3299, 2011.

Zhen, et al.,"The Effect of Blockade of k-Opioid Receoptors in the Medial Basal Hypothalamus and Medial Preoptic Area on Luteinizing Hormone Release during Midpregnancy in the Rat," Endocrinology, vol. 131, No. 4, pp. 1650-1656,1992.

Zsoter, et al., The effect of diazepam and pentazocine on the venomotor reflexes in man, The Journal of Clinical Pharmacology and New Drugs, vol. 12, No. 2, pp. 91, 1972.

Li, et al., "In vitro assessment of metabolic drug-drug interaction potential of AZD2624, neuro-kinin-3 receptor antagonist, through cytochrome P450 enzyme identification, inhibition, and induction, "Xenoblotica, 2010; 40(11): 721-729.

\* cited by examiner

METHODS AND COMPOSITIONS FOR TREATING VASOMOTOR SYMPTOMS

CROSS REFERENCE

This application is a continuation of U.S. application Ser. No. 15/586,762, filed on May 4, 2017, now abandoned, which is a continuation of U.S. application Ser. No. 15/226,408, filed on Aug. 2, 2016, now abandoned, which is a continuation of U.S. application Ser. No. 14/439,585, filed on Apr. 29, 2015, now abandoned, which is a national stage entry of PCT/US2013/072772, filed on Dec. 3, 2013, which claims priority to U.S. Provisional Patent Application Ser. No. 61/732,586 filed on Dec. 3, 2012, which are all incorporated by reference herein in their entireties.

BACKGROUND

Vasomotor symptoms (VMS), e.g., thermal instability manifest as hot flashes, chills, night sweats, anxiety, racing heart, facial flushing, and/or heart palpitations, can greatly impact quality of life as women transition through menopause or as they experience declining levels of estradiol following medical or surgical oophorectomy. VMS can be unpleasant, distressing and debilitating. Men may also experience VMS as a result of orchiectomy or medical treatments that acutely suppress testicular function (e.g., gonadotropin-releasing hormone [GnRH] antagonists, which act on the pituitary). Hot flashes and night sweats occur in more than 75% of women who are transitioning through menopause, and hot flashes and night sweats are commonly associated with sleep disturbances, mood changes, heart palpitations, facial skin flushing, and a reduced quality of life. Menopausal VMS are triggered by a loss of estrogenic signaling to the brain, following an age-dependent decline in ovarian function and incipient thermoregulatory instability. Estrogen therapy (ET) is effective in treating VMS; however, ET has significant attendant medical risks particularly for women with a uterus and taking estrogen plus progestin (EPT), including increased incidence of venous/thromboembolism, breast cancer, stroke, coronary artery and gall bladder disease. Many women find such risks unacceptable. Hence, there is a great need to develop better and safer alternatives to treat VMS and reduce their negative impact on patients' health and well-being.

SUMMARY OF THE INVENTION

In a first aspect, the present invention provides methods for treating or limiting development of vasomotor symptoms (VMS), comprising administering to a subject in need thereof an amount effective to treat or limit development of VMS of a compound that inhibits kisspeptin/neurokinin B/dynorphin (KNDy) neurons. In one embodiment, the compound is a kappa receptor agonist. In another embodiment, the compound comprises a neurokinin 3 receptor (NK3R) antagonist and/or a neurokinin 1 receptor (NK1R) antagonist.

In another aspect, the present invention provides methods for treating or limiting development of VMS, comprising administering to a subject in need thereof an amount effective to treat or limit development of VMS of a compound selected from the group consisting of a kappa agonist, an NK3R antagonist, an NK1R antagonist, combinations thereof, and pharmaceutically acceptable salts thereof.

In one embodiment of either aspect of the methods of the invention, the subject is a menopausal or perimenopausal woman; in another embodiment, the subject has surgical or medically-induced VMS. In various further embodiments, treating or limiting development of VMS comprises decreasing or limiting development of one or more of flushing of the skin, sweating, palpitations, racing heart rate, shivering, intermittent feeling of being too hot (hot flashes) or too cold (chills/shivering), irritability, anxiety, mood disorders, and depression, in the subject.

In another aspect, the invention provides pharmaceutical compositions, comprising:
  (1) two or more of a kappa agonist, an NK3R antagonist, an NK1R antagonist, or salts thereof; and
  (2) a pharmaceutically acceptable carrier.

DETAILED DESCRIPTION OF THE INVENTION

It must be noted that, as used in the specification, the singular forms "a," "an" and "the" include plural referents unless the context clearly dictates otherwise.

Any terms not directly defined herein shall be understood to have the meanings commonly associated with them as understood within the art of the present disclosure. Certain terms are discussed herein to provide additional guidance to the practitioner in describing the compositions, devices, methods, and the like, of embodiments of the present disclosure, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the present disclosure herein.

All embodiments disclosed herein can be used in combination, unless the context clearly indicates otherwise. Unless the context clearly requires otherwise, throughout the description and the claims, the words 'comprise', 'comprising', and the like are to be construed in an inclusive sense, as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. Persons skilled in the relevant art can appreciate that many modifications and variations are possible in light of the embodiment teachings. Accordingly, the disclosure is intended to be illustrative, but not limiting, of the scope of invention.

Figure 1:
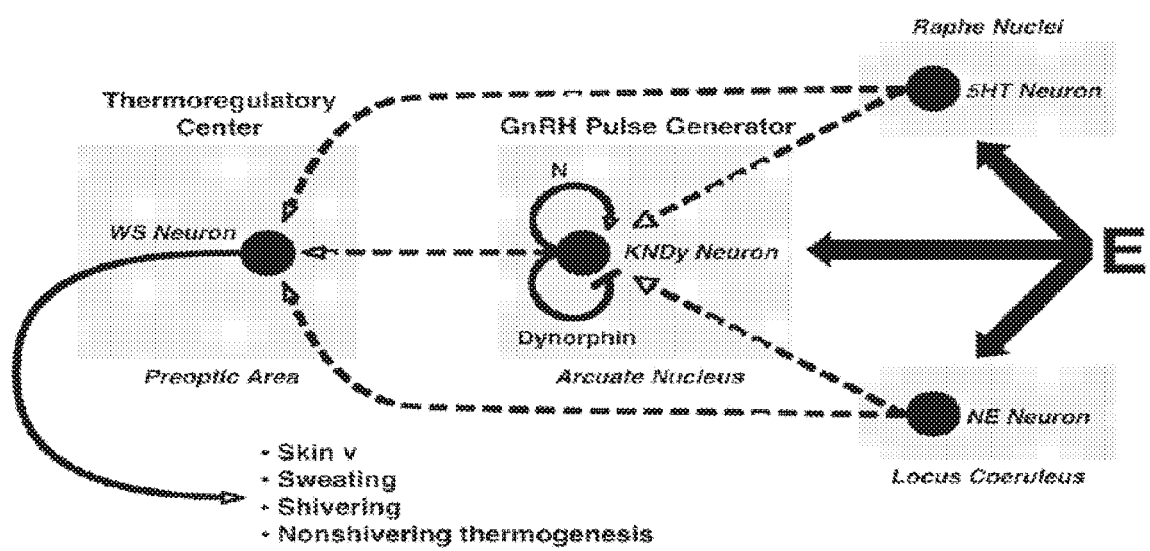
FIG. 1 is a graphical representation of the action of estrogen-sensitive kisspeptin/dynorphin/NKB (KNDy) neurons in the arcuate nucleus and the thermoregulatory centers (comprising "warm-sensing" (WS) neurons in the preoptic area (POA)), which control vasomotor function (and trigger hot flashes). Also shown is the modulatory input of estrogen-sensitive serotonergic (5HT) and noradrenergic neurons (NE), which send projections to the POA from the raphe nuclei and locus coeruleus, respectively.

In a first aspect the present invention provides methods for treating or limiting development of vasomotor symptoms (VMS), comprising administering to a subject in need thereof an amount effective to treat VMS of a compound that inhibits kisspeptin/neurokinin B/dynorphin (KNDy) neuronal activity. As disclosed herein, the inventors have discovered that blocking KNDy neuronal activity (either altering KNDy neuronal activity, or interfering with the ability of KNDy neurons to communicate with downstream target cells) serves to treat VMS. While not being bound by any specific mechanism of action, FIG. 1 illustrates a model of linkage of KNDy neurons in the arcuate nucleus to thermoregulatory centers located in the preoptic area (POA) of the hypothalamus. As illustrated in FIG. 1, the network of KNDy neurons influences the hypothalamic mechanisms that control thermoregulation. Accordingly, aspects of the present disclosure are directed to methods and compositions for the treatment of VMS-associated thermoregulatory instability.

The methods of the invention can be used to treat any suitable subject, such as a human subject (male or female) suffering from VMS or at risk of developing hot flashes. In one embodiment, the subject is a menopausal or perimenopausal woman. In another embodiment, the subject is a subject with medically- or surgically-induced VMS, or who is at risk of medically- or surgically-induced VMS (e.g., a subject who has undergone or will be undergoing a medical or surgical procedure that may cause VMS, including but not limited to medical or surgical oophorectomy, orchiectomy or medical treatments that acutely suppress testicular function (e.g., GnRH antagonists).

The methods of the invention serve to treat or limit development of one or more VMS associated with thermal instability which include, but are not limited to, flushing of the skin (blushing/reddening), sweating, palpitations, racing heart rate, heart palpitations, intermittent feeling of being too hot (hot flashes) or too cold (chills/shivering), sleep disturbances, irritability, anxiety, depression and mood disorders. VMS as used throughout this document refers to this definition with one or more of its concomitant associated symptoms.

As used herein, "treat" or "treating" means accomplishing one or more of the following in an individual that is suffering from VMS: (a) reducing the severity of one or more VMS; (b) limiting or preventing development of one or more VMS; (c) inhibiting worsening of one or more VMS; (d) limiting or preventing one or more VMS recurrence in subjects that have previously had the disorder(s); and (e) limiting or preventing recurrence of one or more VMS in patients that previously had VMS.

As used herein, "limiting" or "limiting development of" means accomplishing one or more of the following in an individual that has not yet experienced VMS: (a) limiting development of one or more VMS; (b) reducing the severity one or more VMS; and (c) limiting or preventing development of one or more VMS.

As used herein, an "amount effective" refers to an amount of the composition that is effective for treating and/or limiting the relevant one or more VMS. The effective amount may vary from subject to subject, depending upon the age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present disclosure, generally a therapeutic amount will be in the range of about 0.01 mg/kg to about 250 mg/kg body weight, more preferably about 0.1 mg/kg to about 10 mg/kg, in at least one dose. The subject can be administered as many doses as is required to treat or limit the hot flashes.

Any suitable compounds that can either block KNDy neuronal activity or interfere with the ability of KNDy neurons to communicate with other neurons can be used in the methods of the invention. In non-limiting embodiments, the compounds may be kappa agonists, including but not restricted to those whose action is predominantly "peripheral" or outside of the confines the blood-brain barrier, so-called peripherally-restricted agents, such as peripherally restricted kappa agonists (PRKAs), neurokinin type 3 receptor (NK3R) antagonists, or neurokinin type 1 receptors (NK1R) antagonists, combinations thereof, and salts thereof, all of which can act in the hypothalamus to inhibit KNDy neuron activity (and potentially VMS related to thermal instability). In a preferred embodiment, the compound's action is predominantly "peripheral" or outside of the confines the blood-brain barrier, and the compounds are referred to as peripherally-restricted agents.

Kappa agonists act in the hypothalamus (part of which is outside of the blood-brain barrier and therefore accessible to agents that are administered into the "periphery", i.e., by oral, peripheral intravenous, intraperitoneal, or subcutaneous routes of administration) to suppress GnRH secretion and inhibit KNDy neuronal activity (22, 25, 29-32). Accordingly, one embodiment of the present invention is directed to activating kappa receptor signaling pathways in the arcuate nucleus—which is outside of the blood-brain-barrier and accessible to systemically-delivered (even highly charged) compounds (33-35 and 40-41)—with a peripherally-restricted kappa agonist (PRKA), thereby reducing or blocking pulsatile KNDy neuronal activity and thereby ameliorating VMS. Likewise, other agents that suppress KNDy neuron activity (such as NK3R or NK1R antagonists, including but not limited to peripherally restricted antagonists) would inhibit KNDy neuronal activity and VMS.

The term "agonist" refers to a compound that can combine with a kappa receptor to produce or alter (i.e., modulate, inhibit, activate or induce) cellular activity, so as to mimic the action of the endogenous, naturally occurring ligand. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the kappa receptor. The term "activate", and variations thereof, refers to any measurable increase in cellular activity.

Another aspect of the present invention provides methods for treating VMS, comprising administering to a subject in need thereof an amount effective to treat VMS with a kappa agonist, an NK3R antagonist, an NK1R antagonist, combinations thereof, and pharmaceutically acceptable salts thereof.

Any suitable kappa agonists can be used in the methods of the present invention. In various non-limiting embodiments, the kappa agonist may comprise or consist of one or more of the following (or stereoisomers, mixture of stereoisomers, prodrugs, pharmaceutically acceptable salts, hydrates, salts, solvates, acid salt hydrates, N-oxides and isomorphic crystalline forms thereof):

(a) Dynorphin A: (Available from, for example, Tocris Bioscience);

(b) (−) U50,488—(Available from Sigma-Aldrich, for example)

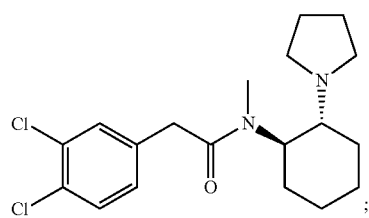 [SMILES: CN(C(=O)Cc1ccc(Cl)c(Cl)c1)[C@@H]1CCCC[C@H]1N1CCCC1]

(c) ICI 199,441 (Available from, for example, Tocris Bioscience) Chemical Name: 2-(3,4-Dichlorophenyl)-N-methyl-N-[(1S)-1-phenyl-2-(1-pyrrolidinyl)ethyl]acetamide hydrochloride (Cat. #0778)

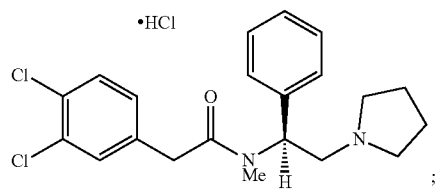

(d) ICI 204,448—(Available from, for example, Tocris Bioscience): Chemical Name: (RS)-[3-[1-[[(3,4-Dichlorophenyl)acetyl]methylamino]-2-(1-pyrrolidinyl)ethyl]phenoxy]acetic acid hydrochloride

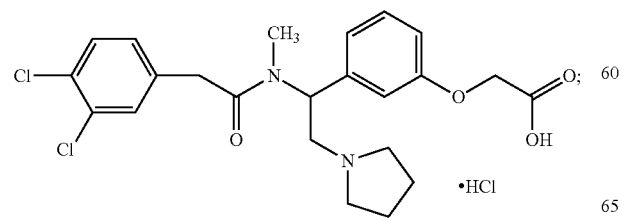

(e) Asimadoline (EMD-61753)—(Available from, for example, Tocris Bioscience): Chemical Name: N-[(1S)-2-[(3S)-3-hydroxypyrrolidin-1-yl]-1-phenylethyl]-N-methyl-2,2-diphenylacetamide

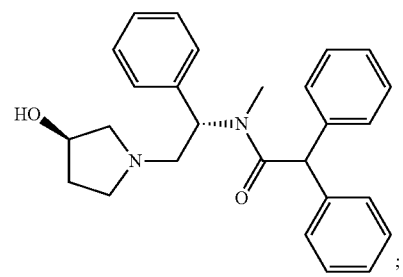 [SMILES: CN(C(=O)C(c1ccccc1)c1ccccc1)[C@H](CN1CC[C@@H](O)C1)c1ccccc1]

(f) Bremazocine—Chemical names: 6-ethyl-3-[(1-hydroxycyclopropyl)methyl]-11,11-dimethyl-1,2,3,4,5,6-hexahydro-2,6-methano-3-benzazocin-8-ol; also known as 2-(1-hydroxy-cyclopropylmethyl)-5-ethyl-9,9-dimethyl-2'-hydroxy-6,7-benzomorphan

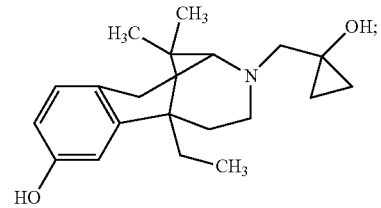 [SMILES: CCC12CCN(CC3(O)CC3)C3C(C)(C)C31Cc1ccc(O)cc12]

(g) BRL 52537—(Available from, for example, Tocris Bioscience): (±)-1-(3,4-Dichlorophenyl)acetyl-2-(1-pyrrolidinyl)methylpiperidine hydrochloride (Cat. #0699)

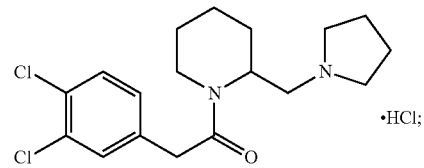 [SMILES: O=C(Cc1ccc(Cl)c(Cl)c1)N1CCCCC1CN1CCCC1]

(h) β-NNTA

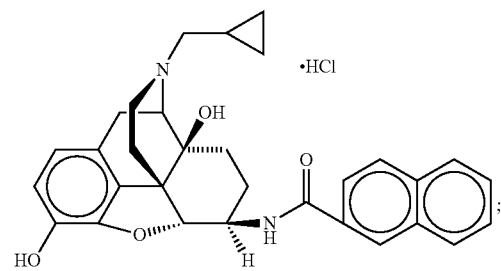

(i) Enadoline: Also known as Cam 569; PD 129289; 4-Benzofuranacetamide, N-methyl-N-(7-(1-pyrrolidinyl)-1-oxaspiro(4.5)dec-8-yl); N-Methyl-N-(7-(1-pyrrolidinyl)-1-oxaspiro(4,5)dec-8-yl)-4-benzofuranacetamide; SureCN2- 20054; AC1L334T; CAM-569; CAM-570; C24H32N2O3; LS-172051; PD-129289; PD-129290; L000184; 1-Oxaspiro (4.5)decane, 4-benzofuranacetamide deriv; 2-(1-benzofuran-4-yl)-N-methyl-N-(9-pyrrolidin-1-yl-4-oxaspiro[4.5] decan-8-yl)acetamide; 107431-28-7

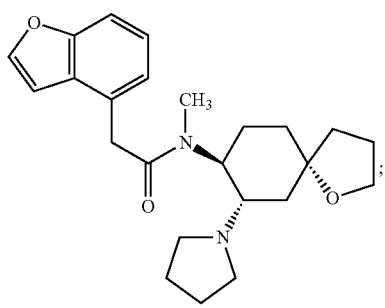 [SMILES: CN(C(=O)Cc1cccc2occc12)[C@H]1CC[C@@]2(CCCO2)C[C@@H]1N1CCCC1]

(j) FE 200665 (CR665)—(Available from, for example, Tocris Bioscience): (R)-2-((R)-2-((R)-2-amino-3-phenylpropanamido)-3-phenylpropanamido)-N-((R)-5-guanidino-1-oxo-1-((pyridin-4-ylmethyl)amino)pentan-2-yl)hexanamide; also known as H-D-Phe-D-Phe-D-Nle-D-Arg-NH-4-Picolyl

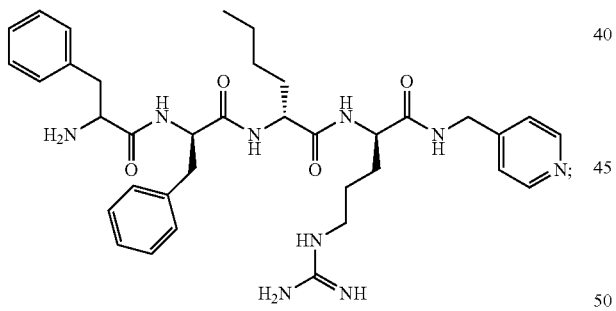

(k) Fedotozine—(2R)-N,N-dimethyl-2-phenyl-1-[(3,4,5-trimethoxybenzyl)oxy]-2-butanamine

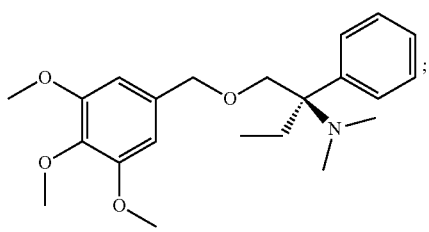 [SMILES: CC[C@](COCc1cc(OC)c(OC)c(OC)c1)(c1ccccc1)N(C)C]

(l) 6' GNTI—(Available from, for example, Tocris Bioscience): 5'-Guanidinyl-17-(cyclopropylmethyl)-6,7-dehydro-4,5α-epoxy-3,14-dihydroxy-6,7-2',3'-indolomorphinan dihydrochloride

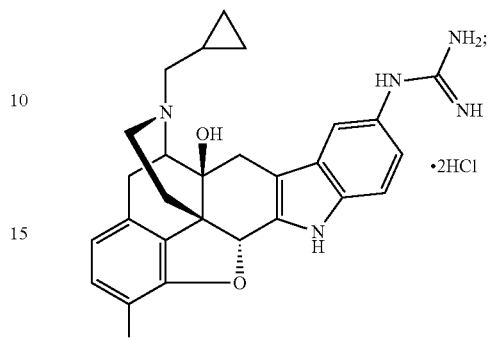

(m) GR89696—(Available from, for example, Tocris Bioscience): 4-[(3,4-Dichlorophenyl)acetyl]-3-(1-pyrrolidinylmethyl)-1-piperazinecarboxylic acid methyl ester fumarate (Cat. #1483)

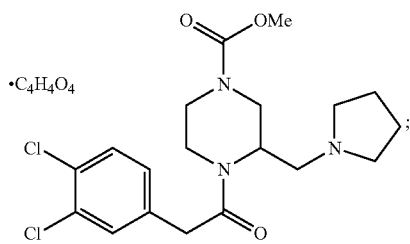 [SMILES: "·C4H4O4" ; COC(=O)N1CCN(C(=O)Cc2ccc(Cl)c(Cl)c2)C(CN2CCCC2)C1]

(n) HZ-2—Dimethyl 3,7-dimethyl-9-oxo-2,4-dipyridin-2-yl-3,7-diazabicyclo[3.3.1]nonane-1,5-dicarboxylate

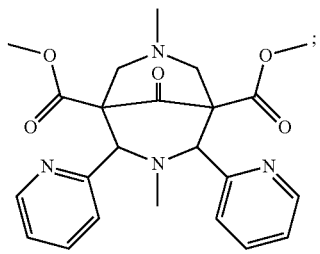

(o) Ketocyclazocine (Available from, for example, Toronto Research Chemicals) (2S,6R,11R)-3-(cyclopropylmethyl)-8-hydroxy-6,11-dimethyl-3,4,5,6-tetrahydro-2,6-methano-3-benzazocin-1(2H)-one; also known as (−)-Keto Cyclazocine and Ketazocine

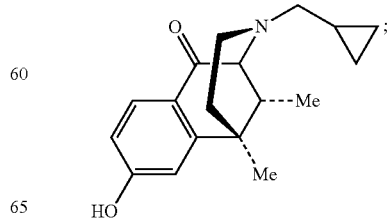

(p) Levallorphan—(Available from, for example, Sigma Aldrich): (−)-17-allylmorphinan-3-ol; also known as Lorfan, naloxiphan, and 17-(2-Propenyl)morphinan-3-ol tartrate

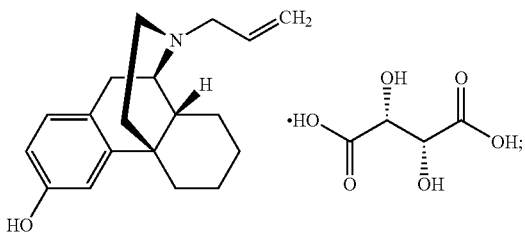

(q) LPK-26—(Available from, for example, Sigma Aldrich): 2-(3,4-dichlorophenyl)-N-[(2S)-1-(2,5-dihydropyrrol-1-yl)-3-methylbutan-2-yl]-N-methylacetamide; or 2-(3,4-Dichlorophenyl)-N-methyl-N-[(1S)-1-(2-isopropyl)-2-(1-(3-pyrrolinyl))ethyl]acetamide hydrochloride

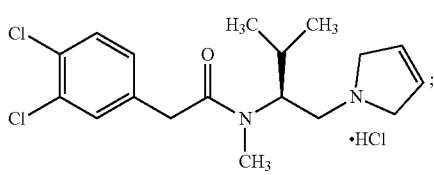 [SMILES: CC(C)[C@@H](CN1CC=CC1)N(C)C(=O)Cc1ccc(Cl)c(Cl)c1 ; Cl]

(r) Nalfurafine HCl: (2E)-N-[(5α,6β)-17-(cyclopropylmethyl)-3,14-dihydroxy-4,5-epoxymorphinan-6-yl]-3-(3-furyl)-N-methylacrylamide

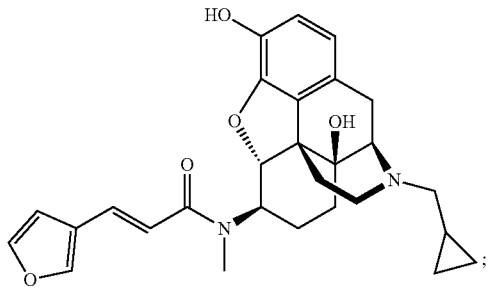

(s) N-Methyl-N-(7-(1-pyrolidinyl)-1-oxaspiro(4,5)dec-8-yl)-4-benzofuranacetamide (t) N-MPPP Hydrochloride (Available from, for example, Tocris Bioscience): N-Methyl-N-[(1S)-1-phenyl-2-(1-pyrrolidinyl)ethyl]phenylacetamide hydrochloride (Cat. #0783)

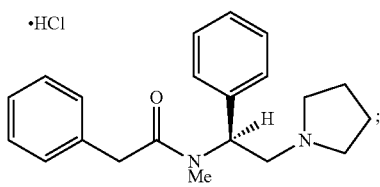 [SMILES: CN(C(=O)Cc1ccccc1)[C@H](CN1CCCC1)c1ccccc1 ; Cl]

(u) (−) Pentazocine—(Available from, for example, Sigma Aldrich)

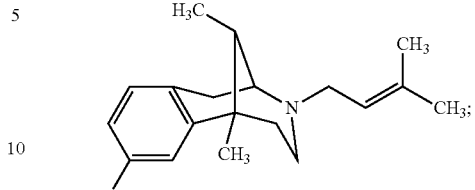

(v) (+) Pentazocine—(Available from, for example, Sigma Aldrich)

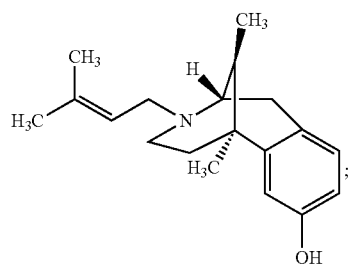 [SMILES: CC(C)=CCN1CC[C@]2(C)c3cc(O)ccc3C[C@H]1[C@H]2C]

Both versions of Pentazocine (u and v) are also known as: Pentazocaine, Liticon, Pentagin, Pentazocin, Soseton, Taiwan, Fortral, Fortalgesic, or Fortalin;

(w) Salvinorin A (Available from, for example, Tocris Bioscience): (2S,4aR,6aR,7R,9S,10aS,10bR)-9-(Acetyloxy)-2-(3-furanyl)dodecahydro-6a,10b-dimethyl-4,10-dioxo-2H-naphtho[2,1-c]pyran-7-carboxylic acid methyl ester

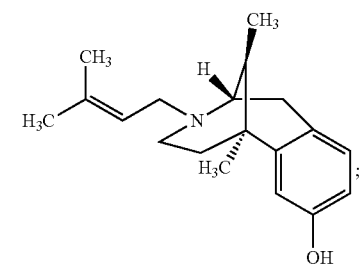

(x) Salvinorin B—(Available from, for example, Sigma-Aldrich): (2S,4aR,6aR,7R,9S,10aS,10bR)-2-(3-Furanyl)dodecahydro-9-hydroxy-6a,10b-dimethyl-4,10-dioxo 2H-naphtho[2,1-c]pyran-7-carboxylic acid methyl ester

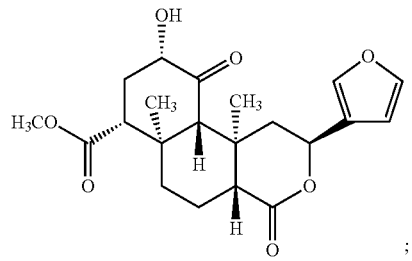

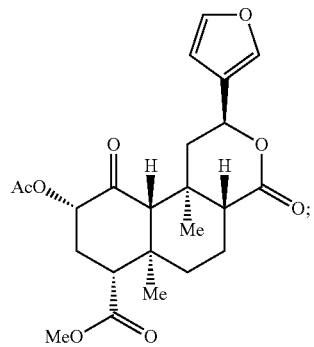

(y) Tifluadom (Available from, for example, Toronto research Chemicals): N-[(5-(2-fluorophenyl)-1-methyl-2,3-dihydro-1,4-benzodiazepin-2-yl)methyl]thiophene-3-carboxamide

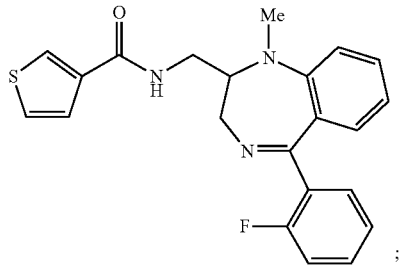 [SMILES: CN1c2ccccc2C(c2ccccc2F)=NCC1CNC(=O)c1ccsc1]

(z) Spiradoline (U-62066) (Available from, for example, Sigma Aldrich): 2-(3,4-dichlorophenyl)-N-methyl-N-[(5R,7S,8S)-7-pyrrolidin-1-yl-1-oxaspiro[4.5]decan-8-yl]

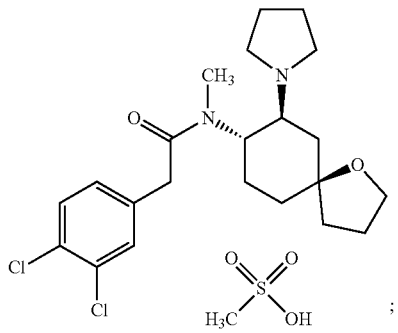

(aa) U-69593—(Available from, for example, Sigma Aldrich): (+)-(5α,7α,8β)-N-Methyl-N-[7-(1-pyrrolidinyl)-1-oxaspiro[4.5]dec-8-yl]-benzeneacetamide

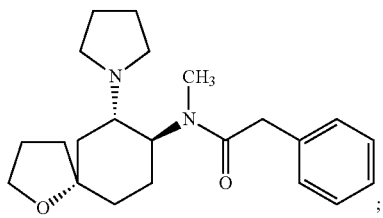 [SMILES: CN(C(=O)Cc1ccccc1)[C@H]1CC[C@@]2(CCCO2)C[C@@H]1N1CCCC1]

(bb) U62066—(Available from, for example, Sigma Aldrich): (±)-(5a,7a,8β)-3,4-Dichloro-N-methyl-N-[7-(1-pyrrolidinyl)-1-oxaspiro[4.5]dec-8-yl]benze

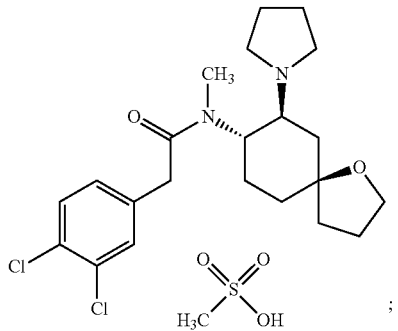

(cc) One or more peptides as disclosed in U.S. Pat. No. 5,965,701 that exhibit high selectivity for the kappa receptor, long duration of in vivo action, and do not exhibit any significant brain penetration (e.g., peripherally restricted). These peptides comprise a sequence of four D-isomer amino acids having a C-terminus that is either mono- or di-substituted amide, and have the following general formula:

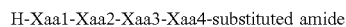

H-Xaa1-Xaa2-Xaa3-Xaa4-substituted amide wherein Xaa1 is (A)D-Phe, (C$^\alpha$Me)D-Phe, D-Tyr, D-Tic or D-Ala(cyclopentyl or thienyl), with A being H, $NO_2$, F, Cl or $CH_3$; Xaa2 is (A')D-Phe, D-1Nal, D-2Nal, D-Tyr or D-Trp, with A' being A or 3,4$Cl_2$; Xaa3 is D-Nle, (B)D-Leu, D-Hle, D-Met, D-Val, D-Phe or D-Ala(cyclopentyl) with B being H or CaMe; Xaa4 is D-Arg, D-Har, D-nArg, D-Lys, D-Lys(Ipr), D-Arg($Et_2$), D-Har($Et_2$), D-Amf(G), D-Dbu, (B)D-Orn or D-Orn(Ipr), with G being H or amidino; and Q is $NR_1R_2$, morpholinyl, thiomorpholinyl, (C)piperidinyl, piperazinyl, 4-mono- or 4,4-di-substituted piperazinyl or δ-ornithinyl, with $R_1$ being lower alkyl, substituted lower alkyl, benzyl, substituted benzyl, aminocyclohexyl, 2-thiazolyl, 2-picolyl, 3-picolyl or 4-picolyl, $R_2$ being H or lower alkyl; and C being H, 4-hydroxy or 4-oxo.

For purposes of the compounds of (cc), as disclosed in U.S. Pat. No. 5,965,701, by D-Nle is meant D-norleucine, and D-Hle represents D-homoleucine. D-Har represents D-homoarginine, and D-nArg represents D-norarginine, which is one carbon shorter than D-Arg. By D-Nal is meant the D-isomer of alanine that is substituted by naphthyl on the 3-carbon. Preferably, D-2Nal is employed, ie the attachment to naphthalene is at the 2-position on the ring structure; however, D-1Nal may also be used. The abbreviations D-Cpa and D-Fpa are used to represent, respectively, chloro D-Phe and fluoro-D-Phe, With D-4Cpa, D-2Fpa, D-3Fpa and D-4Fpa being preferred. D-Npa means nitro-D-Phe, and D-Mpa is used to represent methyl D-Phe. D-3,4Cpa means 3,4-dichloro-D-Phe. D-Acp represents D-Ala(cyclopentyl). D-Orn represents D-ornithine, and D-Dbu represents alpha, gamma-diamino butyric acid. CML represents C$^\alpha$methyl Leu, and CMP and CMO represent C$^\alpha$Me Phe and C$^\alpha$Me Orn. By D-4Amf is meant D-4(NH2CH2)Phe, and by D-Gmf is meant Amf(amidino) Which represents D-Phe Where the 4-position is substituted With CH2NHC(NH)NH2. Amd represents amidino, and the symbol D-Amf (Amd) is also used. By D-Tic is meant D-1,2,3,4-tetrahydroisoquinoline-3 carboxylic acid. In Ala(Thi), Thi represents the thienyl group, Which is preferably linked at its 2-position to alanine, although 3-thienyl is an equivalent. By Ily and Ior are respectively meant isopropyl Lys and isopropyl Orn where the side chain amino group is alkylated with isopropy.

(dd) One or more compounds as disclosed in U.S. Pat. No. 7,713,937, synthetic peptide amides that exhibit strong kappa agonist activity and low penetration into the brain (e.g.: they are peripherally restricted), having the formula:

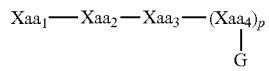

and stereoisomers, mixture of stereoisomers, prodrugs, pharmaceutically acceptable salts, hydrates, solvates, acid salt hydrates, N-oxides and isomorphic crystalline forms thereof, wherein each Xaa1 is independently chosen from (A)(A')D-phenylalanine, (A)(A')(α-Me)D-phenylalanine, D-tyrosine, D-1,2,3,4-tetrahydroisoquinoline-3 carboxylic acid, D-phenylglycine, D-neopentylglycine, D-homophenylalanine, β-(E)D-Ala and D-tert-butyl-Gly, wherein (A) and (A') are each phenyl ring substituents independently chosen from —H, —F, —Cl, —NO2, —CH3, —CF3, —CN, —CONH2, and wherein each (E) is independently chosen from tert-butyl, cyclopropyl, cyclobutyl, cyclopentyl, cyclohexyl, furyl, pyridyl, thienyl, thiazolyl and benzothienyl. Each Xaa2 is independently chosen from (A)(A')D-phenylalanine, (A)(A')(α-Me)D-phenyl-alanine, naphthyl-1-D-alanine, naphthyl-2-D-alanine, D-tyrosine, (E)D-alanine, and D-tryptophan. Each Xaa3 is independently chosen from D-norleucine, D-phenylalanine, (E)D-alanine, D-leucine, (α-Me)D-leucine, D-homoleucine, D-valine, and D-methionine. Each Xaa4 is independently chosen from (B)2D-arginine, (B)2D-norarginine, (B)2D-homoarginine, ζ-(B)D-homolysine, D-2,3-diaminopropionic acid, ε-(B)D-lysine, ε-(B)2-D-lysine, D-(NH2CH2-)phenylalanine, amidino-D-(NH2CH2-) phenylalanine, γ-(B)2D-diamino butyric acid, δ-(B)2α-(B')D-ornithine, D-2-amino-3(4-piperidyl)propionic acid, D-2-amino-3(2-aminopyrrolidyl)propionic acid, D-α-amino-β-amidino-propionic acid, α-amino-4-piperidineacetic acid, cis-α,4-diaminocyclohexane acetic acid, trans-α,4-diaminocyclohexaneacetic acid, cis-α-amino-4-methyl-aminocyclo-hexane acetic acid, trans-α-amino-4-methylaminocyclohexane acetic acid, α-amino-1-amidino-4-piperidineacetic acid, cis-α-amino-4-guanidino-cyclohexane acetic acid, and trans-α-amino-4-guanidinocyclohexane acetic acid, wherein each (B) is independently chosen from —H and C1-C4 alkyl, and (B') is —H or (α-Me); and p is zero or 1.

In another embodiment G is selected from one of the following three moieties:

(i) G is

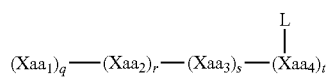

wherein p, q, r, s and t are each independently zero or 1, provided that at least one of s and t are 1; and L is a linker chosen from ε-D-lysine, ε-lysine, δ-D-ornithine, ε-ornithine, γ-amino-butyric acid, 8-aminooctanoic acid, 11-amino-undecanoic acid, 8-amino-3,6-dioxa-octanoic acid, 4-amino-4-carboxylic piperidine and bis(D-Lys-Gly)Lactam. The synthetic peptide amides of this embodiment are also herein interchangeably referred to as 'dimers,' dimeric structures' or 'synthetic peptide amide dimers' since they include two synthetic peptide amide components joined by the linking moiety, L.

(ii) G is

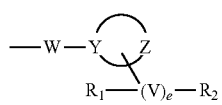

and p is 1; and the moiety

is an optionally substituted 4 to 8-membered heterocyclic ring moiety wherein Y is C or N and Z is a carbon atom, a nitrogen atom, an oxygen atom, a sulfur atom, a sulfoxide group, or a sulfonyl group; provided that when such ring moiety is a 6-, 7- or 8-membered ring, Y and Z are separated by at least two ring atoms; and provided further that when such ring moiety is aromatic, then Y is a carbon atom; and (iii) G is

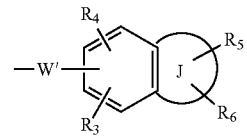

wherein J is a 5-, 6-, or 7-membered heterocyclic ring moiety comprising 1, 2, or 3 heteroatoms in the ring, wherein R3 and R4 are each independently selected from H, C1-C3 alkyl, halo, —OH, —CF3, —NH2, —COOH and amidino; and R5 and R6 are each independently chosen from H, C1-C3 alkyl, oxo, halo, —OH, —CF3, —NH2, —COOH and amidino; wherein W' is chosen from: the moiety —NH—(CH2)b- with b equal to zero, 1, 2, 3, 4, 5, or 6; and the moiety —NH—(CH2)c-O— with c equal to 2 or 3.

In another embodiment, V is C1-C6 alkyl, and e is zero or 1, wherein when e is zero, then V is null and, R1 and R2 are directly bonded to the same or different ring atoms; wherein (a) R1 is —H, —OH, halo, CF3, —NH2, —COOH, C1-C6 alkyl, C1-C6 alkoxy, amidino, C1-C6 alkyl-substituted amidino, aryl, optionally substituted heterocyclyl, Pro-amide, Pro, Gly, Ala, Val, Leu, Ile, Lys, Arg, Orn, Ser, Thr, CN, CONH2, COR', SO2R', CONR'R", NHCOR', OR', or SO2NR'R"; wherein said optionally substituted heterocyclyl is optionally singly or doubly substituted with substituents independently selected from the group consisting of C1-C6 alkyl, —C1-C6 alkoxy, oxo, —OH, —Cl, —F, —NH2, —NO2, —CN, —COOH, and amidino; wherein R' and R" are each independently —H, C1-C8 alkyl, aryl, or heterocyclyl or R' and R" are combined to form a 4-, 5-, 6-, 7-, or 8-membered ring, which ring is optionally substituted singly or doubly with substituents independently selected from the group consisting of C1-C6 alkyl, —C1-C6 alkoxy, —OH, —Cl, —F, —NH2, —NO2, —CN, and —COOH, amidino; and R2 is H, amidino, singly or doubly C1-C6 alkyl-substituted amidino, —CN, —CONH2, —CONR'R", —NHCOR', —SO2NR'R", or —COOH; or (b) R1 and R2 taken together can form an optionally substituted 4-, 5-, 6-, 7-, 8- or 9-membered heterocyclic monocyclic or bicyclic ring moiety which is bonded to a single ring atom of the Y and Z-containing ring moiety; or (c) R1 and R2 taken together with a single ring atom of the Y and Z-containing ring moiety can form an optionally substituted 4-, 5-, 6-, 7-, or 8-membered heterocyclic ring moiety to form a Spiro structure; or (d) R1 and R2 taken together with two or more adjacent ring atoms of the Y and Z-containing ring moiety can form an optionally substituted 4-, 5-, 6-, 7-, 8- or 9-membered heterocyclic monocyclic or bicyclic ring moiety fused to the Y and Z-containing ring moiety; and wherein each of said optionally substituted 4-, 5-, 6-, 7-, 8- or 9-membered heterocyclic ring moieties comprising R1 and R2 is optionally singly or doubly substituted with substituents independently selected from the group consisting of C1-C6 alkyl, —C1-C6 alkoxy, optionally substituted phenyl, oxo, —OH, —Cl, —F, —NH2, —NO2, —CN, —COOH, and amidino; provided that when the Y and Z-containing ring moiety is a six or seven-membered ring having a single ring heteroatom and such heteroatom is N, and e is zero, then R1 is not —OH, and R1 and R2 are not both —H; provided further that when the Y and Z-containing ring moiety is a non-aromatic six membered ring comprising two ring heteroatoms, both Y and Z are N, W is null, and -Ve(R1)(R2) is attached to Z, then Ve(R1)(R2) is selected from the group consisting of amidino, C1-C6 alkyl-substituted amidino, dihydroimidazole, —CH2COOH, and —CH2C(O)NH2; and lastly, provided that if the Y and Z-containing ring moiety is a six membered ring comprising an S or O ring heteroatom, or if the Y and Z-containing ring moiety is a six membered ring comprising two ring heteroatoms, wherein both Y and Z are N and W is null, or if the Y and Z-containing ring moiety is a six membered aromatic ring comprising a single ring heteroatom, which heteroatom is N, then, when e is zero, R1 and R2 are not both —H.

In one embodiment the synthetic peptide amides of formula:

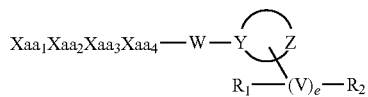

and stereoisomers, mixtures of stereoisomers, racemates, prodrugs, pharmaceutically acceptable salts, hydrates, solvates, acid salt hydrates, N-oxides and isomorphic crystalline forms thereof; wherein Xaa1 is chosen from (A)(A')D-Phe, (α-Me)D-Phe, D-Tyr, D-Tic, D-phenylglycine, D homophenylalanine, β-(E)D-Ala and D-tert-butyl-Gly, wherein (A) and (A') are each phenyl ring substituents independently chosen from —H, —F, —Cl, —NO2, —CH3, —CF3, —CN, and CONH2, and (E) is chosen from tert-butyl, cyclopropyl, cyclobutyl, cyclopentyl, cyclohexyl, furyl, pyridyl, thienyl, thiazolyl and benzothienyl. Xaa2 is chosen from (A)(A')D-Phe, (α-Me)D-Phe, D-1Nal, D-2Nal, D-Tyr, (E)D-Ala and D-Trp; and Xaa3-Xaa4-is chosen from f D-Nle-(B)2D-Arg-, D-Leu-δ-(B)2α-(B')D-Orn-, and (α-Me)D-Leu-δ(B)2-α(B')D-Orn-; wherein each (B) is independently chosen from —H and C1-C4 alkyl, and (B') is —H or (α-Me). W in the above formula is chosen from one of the following three options:

(i) Null, provided that when W is null, Y is N; or
(ii) —N—(CH2)b with b equal to zero, 1, 2, 3, 4, 5, or 6; or
(iii) —N—(CH2)n-O— with c equal to 2, or 3, provided that Y is a carbon atom.

In one embodiment the Y- and Z-containing moiety in the above formula is an optionally substituted 4-8 membered saturated mono- or dinitrogen heterocyclic ring moiety, in which no ring atom other than Y and Z is a heteroatom, Y is C or N, Z is C or N, and at least one of Y and Z is N, and provided that in the case of a 4 or 5 membered heterocyclic ring, either Y or Z is C, and in the case of a dinitrogen heterocycle, Y and Z are separated by two or more ring carbon atoms.

In another embodiment, when the Y- and Z-containing ring moiety is a saturated six-membered ring that includes only two ring heteroatoms which are both N and W is null, then Z is not N.

In another embodiment the moiety V is C1-C6 alkyl, and e is zero or 1, wherein when e is zero, then V is null, R1 and R2 are directly bonded to the same or different ring atoms. R1 is H, OH, —NH2, —COOH, C1-C6 alkyl, C1-C6 alkoxy, amidino, C1-C6 alkyl-substituted amidino, dihydroimidazole, Pro-amide, Pro, Gly, Ala, Val, Leu, Ile, Lys, Arg, Orn, Ser, Thr, CN, CONH2, CONR'R", NHCOR', or SO2NR'R", wherein R' and R" are each independently H, or C1-C8 alkyl, or R' and R" are combined to form a 4-, 5-, 6-, 7-, or 8-membered ring which ring is optionally substituted singly or doubly with substituents independently chosen from C1-C6 alkyl, —OH, —Cl, —F, —NH2, —NO2, —CN, and —COOH, amidino; and R1 is H, amidino, singly or doubly C1-C6 alkyl-substituted amidino, —CN, —CONH2, —CONR'R", —NHCOR', —SO2NR'R", or —COOH.

In one embodiment, formula I is subject to two provisos: (i) when the Y and Z-containing ring moiety is a six or seven membered ring and when one of Y and Z is C and e is zero, then R1 is not OH, and R1 and R2 are not both H; and (ii) when the Y and Z-containing ring moiety is a six membered ring, both Y and Z are N and W is null, then -(V)eR1R2 is attached to a ring atom other than Z; and if e is zero, then R1 and R2 are not both —H.

In certain embodiments the synthetic peptide amides have the formula:

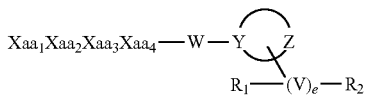

wherein Xaa1 is chosen from (A)(A')D-Phe, (α-Me)D-Phe, D-Tyr, D-Tic, (E)D-Ala and D-tert-butyl-Gly, wherein (A) and (A') are each phenyl ring substituents independently chosen from —H, —F, —Cl, —NO2, —CH3, —CF3, —CN, —CON—H2, and wherein (E) is selected from the group consisting of tert-butyl, cyclopropyl, cyclobutyl, cyclopentyl, cyclohexyl, furyl, pyridyl, thienyl, thiazolyl and benzothienyl. Xaa2 is chosen from (A)(A')D-Phe, (α-Me)D-Phe, D-1Nal, D-2Nal, D-Tyr, (E)D-Ala and D-Trp. Xaa3 is chosen from D-Nle, D-Phe, cyclopentyl-D-Ala, D-Leu, (α-Me)D-Leu, D-Hle, D-Val, and D-Met. Xaa4 is chosen from (B)2D-Arg, (B)2D-nArg, (B)2D-Har, ζ-(B)D-Hlys, D-Dap, ε-(B)D-Lys, ε-(B)2-D-Lys, D-Amf, amidino-D-Amf, γ-(B)2D-Dbu, δ-(B)2α-(B')D-Orn, D-2-amino-3(4-piperidyl)propionic acid, D-2-amino-3(2-aminopyrrolidyl)propionic acid, D-α-amino-β-amidinopropionic acid, (R)-α-amino-4-piperidineacetic acid, cis-α,4-diaminocyclohexane acetic acid, trans-α,4-diaminocyclohexaneacetic acid, cis-α-amino-4-methylamino-cyclohexane acetic acid, trans-α-amino-4-methylamino-cyclohexane acetic acid, α-amino-1-amidino-4-piperidineacetic acid, cis-α-amino-4-guanidinocyclohexane acetic acid, and trans-α-amino-4-guanidinocyclohexane acetic acid, wherein each (B) is independently selected from the group consisting of H and C1-C4 alkyl, and (B') is H or (α-Me). The moiety W is chosen from one of the following three options: (i) null; (ii) —N—(CH2)b with b equal to zero, 1 2, 3, 4, 5, or 6; and (iii) —N—(CH2)c-O— with c equal to 2 or 3 provided Y is a carbon atom.

In this embodiment, the Y- and Z-containing ring moiety,

is an optionally substituted 6-8 membered saturated heterocyclic ring moiety, wherein no ring atom other than Y and Z is a heteroatom, Y and Z are separated by at least two carbon ring atoms, Y is C or N, and Z is S, O or N.

The moiety V is C1-C6 alkyl, and e is zero or 1, wherein when e is zero, then V is null and, R1 and R2 are directly bonded to the same or different ring atoms; R1 is H, OH, —NH2, —COOH, C1-C6 alkyl, amidino, C1-C6 alkyl-substituted amidino, dihydroimidazole, D-Pro, Gly, D-Ala, D-Val, D-Leu, D-Ile, D-Lys, D-Arg, D-Orn, D-Ser, D-Thr, —CN, —CONH2, —CONR'R", —NHCOR', or —SO2NR'R", wherein R' and R" are each independently —H, or C1-C8 alkyl, or R' and R" are combined to form a 4-, 5-, 6-, 7-, or 8-membered ring which ring is optionally substituted singly or doubly with substituents independently chosen from C1-C8 alkyl, —OH, —Cl, —F, —NH2, —NO2, —CN, and —COOH, amidino; and R2 is —H, amidino, C1-C6 alkyl-substituted amidino, —CN, —CONH2, —CONR'R", —NHCOR', —SO2NR'R", or —COOH.

In certain embodiments one of the following three provisos apply: when e is zero, then R1 and R2 are not both H; when W is —N—(CH2)c-O—, then Y is C and c is 2 or 3; or (iii) if Z is N, then Y is N, W is null, the Y and Z-containing ring moiety is a non aromatic six membered ring, and -Ve(R1)(R2) is attached to Z, and -Ve(R1)(R2) is chosen from amidino, C1-C6 alkyl-substituted amidino, dihydroimidazole, —CH2COOH, and —CH2C(O)NH2.

In certain other embodiments the synthetic peptide amides are dimers that include two synthetic peptide amide components joined by a linking moiety, L. In one aspect the synthetic peptide amides have the formula:

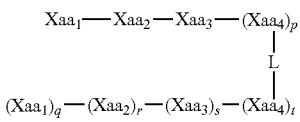

In the above formula, each Xaa1 is independently chosen from (A)(A')D-Phe, (α-Me)D-Phe, D-Tyr, D-Tic, (E)D-Ala and D-tert-butyl-Gly, wherein (A) and (A') are each phenyl ring substituents independently chosen from —H, —F, —Cl, —NO2, —CH3, —CF3, —CN, —CONH2, and wherein (E) is chosen from tert-butyl, cyclopropyl, cyclobutyl, cyclopentyl, cyclohexyl, furyl, pyridyl, thienyl, thiazolyl and benzothienyl. Each Xaa9 is independently chosen from (A)(A')D-Phe, (α-Me)D-Phe, D-1Nal, D-2Nal, D-Tyr, and D-Trp; and r is zero or 1. Each Xaa3 is independently chosen from D-Nle, D-Phe, cyclopentyl-D-Ala, D-Leu, (α-Me)D-Leu, D-Hle, D-Val, and D-Met; and s is zero or 1. Each Xaa4 is independently chosen from (B)2D-Arg, (B)2D-nArg, (B)2D-Har, ε-(B)D-Hlys, D-2,3-diaminopropionic acid, ε-(B)D-Lys, ε-(B)-2-D-Lys, D-Amf, amidino-D-Amf, (B)2D-Dbu, δ-(B)2α-(B')D-Orn, D-2-amino-3(4-piperidyl)propionic acid, D-2-amino-3(2-aminopyrrolidyl)propionic acid, D-α-amino-β-amidinopropionic acid, wherein each (B) is independently selected from the group consisting of H and C1-C4 alkyl, and (B') is H or (α-Me); and p, q, r, s and t are each independently zero or 1, provided that at least one of q, r, s and t are 1. In certain aspects of the invention, at least one of s and t is 1.

The moiety L is a linker chosen from ε-D-Lys, ε-Lys, δ-D-Orn, δ-Orn, γ-aminobutyric acid, 8-aminooctanoic acid, 11-aminoundecanoic acid, 8-amino-3,6-dioxaoctanoic acid, amidino-4-amino-4-carboxylic piperidine and bis(D-Lys-Gly)Lactam.

Stereoisomers, mixtures of stereoisomers, prodrugs, pharmaceutically acceptable salts, hydrates, solvates, acid salt hydrates, N-oxides and isomorphic crystalline forms of these synthetic peptide amides are also contemplated within the scope of the present invention.

In another embodiment, the synthetic peptide amide has the formula:

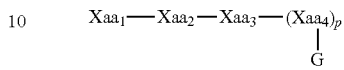

wherein G is

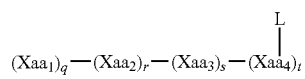

and q is 0 or 1; r is 0 or 1; s is 0 or 1; p and t are each independently 0 or 1, provided that at least one of q, r, s and t are 1; and L is a linker chosen from ε-D-Lys, ε-Lys, δ-D-Orn, δ-Orn, γ-aminobutyric acid, 8-amino-octanoic acid, 11-amino-undecanoic acid, 8-amino-3,6-dioxaoctanoic acid, 4-amino-4-carboxylic piperidine and bis(D-Lys-Gly) Lactam.

In another embodiment, the synthetic peptide amides have the formula:

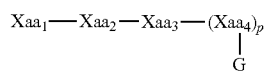

wherein G is

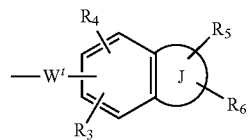

and J is a 5-, 6-, or 7-membered heterocyclic ring moiety having 1, 2, or 3 heteroatoms in the ring, wherein R3 and R4 are each independently chosen from —H, C1-C3 alkyl, halo, —OH, —CF3, —NH2, —COOH and amidino; and R5 and R6 are each independently chosen from —H, C1-C3 alkyl, oxo, halo, —OH, —CF3, —NH2, —COOH and amidino.

In another embodiment, the synthetic peptide amide has the formula:

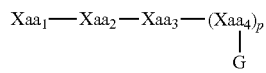

wherein G is

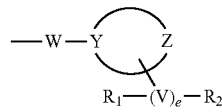

and W is null, Y is N and Z is C. In one aspect, the Y and Z-containing ring moiety is a six-membered saturated ring comprising a single ring heteroatom.

In another embodiment, G is

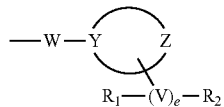

and Y and Z are both N and are the only ring heteroatoms in the Y and Z-containing ring moiety. In another embodiment, e is, zero, and substituents R1 and R2 taken together with zero, one or two ring atoms of the Y and Z-containing ring moiety comprise a monocyclic or bicyclic 4-9 membered heterocyclic ring moiety. In one aspect of this embodiment, R1 and R2 taken together with one ring atom of the Y and Z-containing ring moiety comprise a 4-, 5-, 6-, 7-, or 8-membered heterocyclic ring moiety which with the Y and Z-containing ring moiety forms a spiro structure and W is null.

In another embodiment, G is

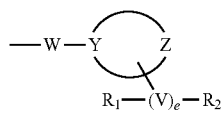

and e is zero and R1 and R2 are bonded directly to the same ring atom. Alternatively, in another embodiment, R1 is H, OH, —NH2, —COOH, —CH2COOH, C1-C3 alkyl, amidino, C1-C3 alkyl-substituted amidino, dihydroimidazole, D-Pro, D-Pro amide, or CONH2 and wherein R2 is H, —COOH, or C1-C3 alkyl.

In another embodiment, G is chosen from the following groups:

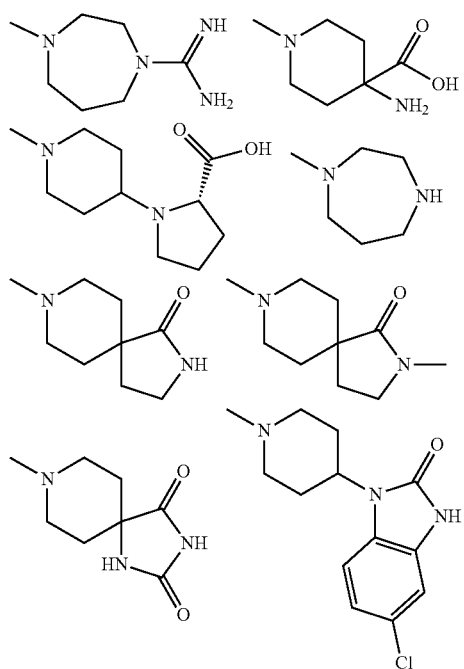

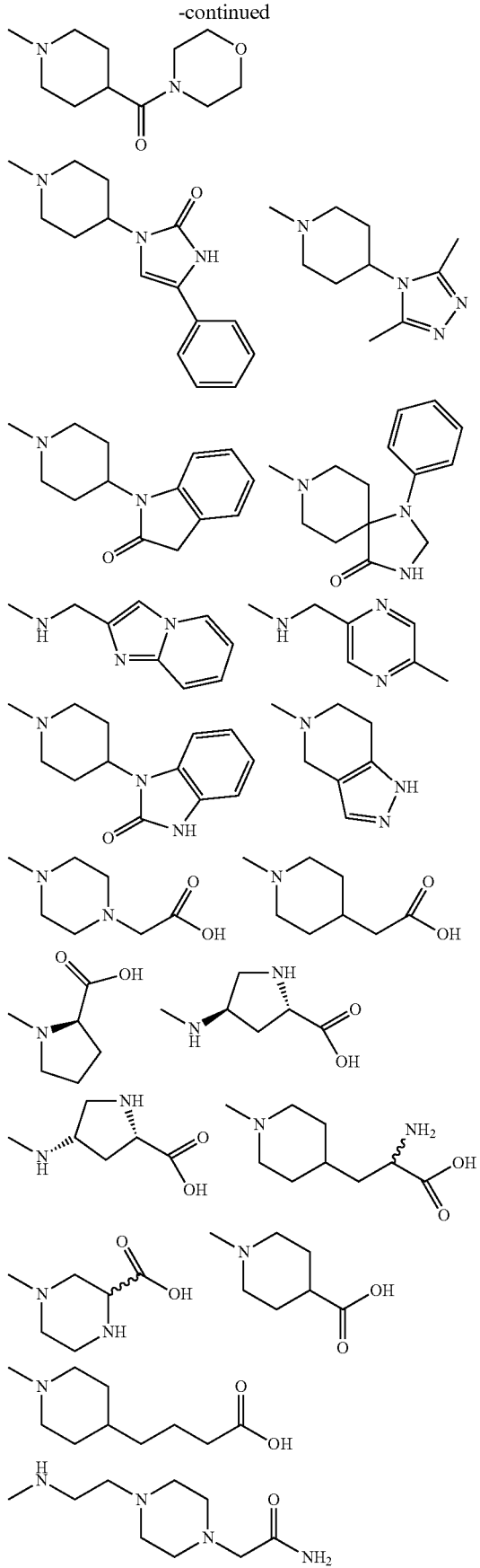

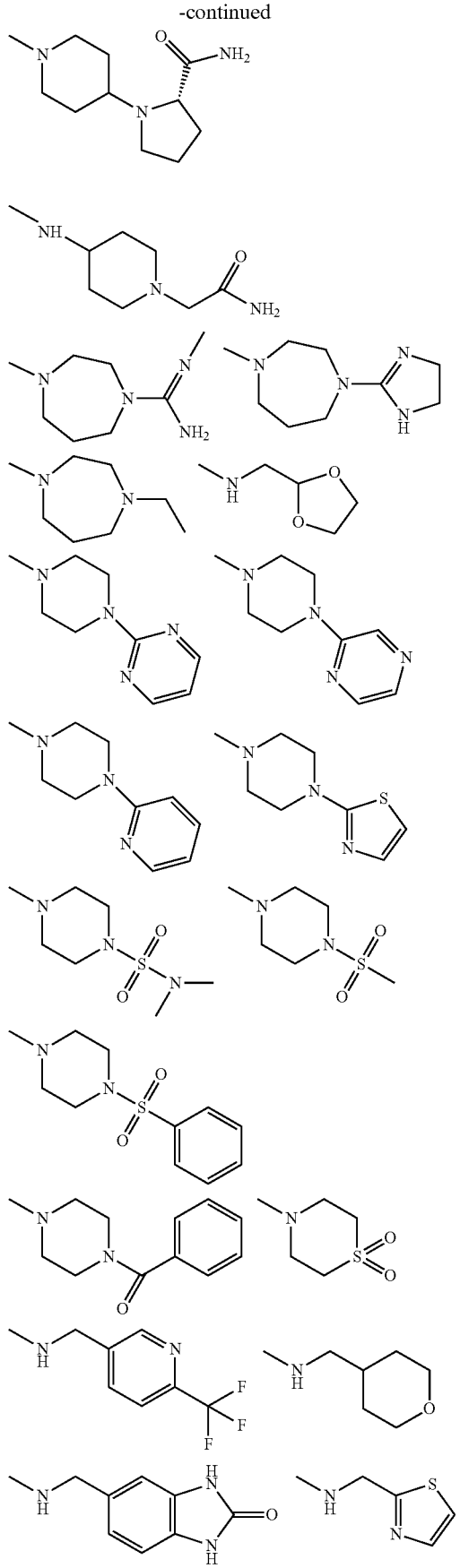

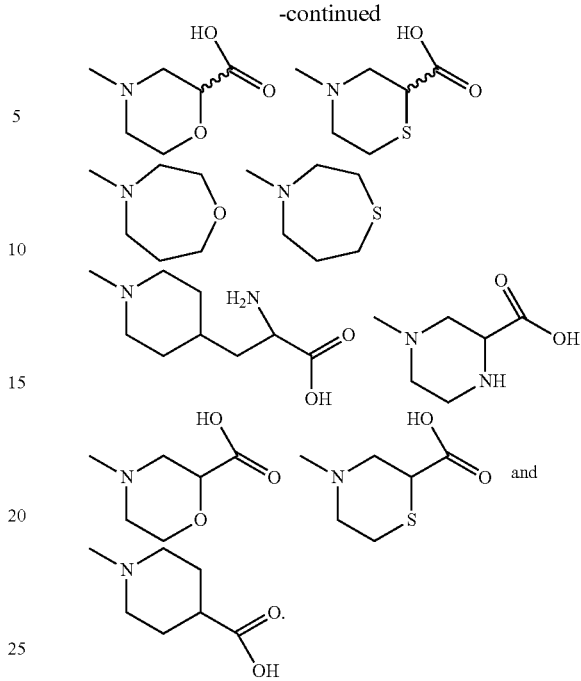

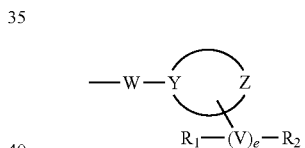

In one embodiment, each Xaa1 is D-Phe, each Xaa2 is D-Phe, each Xaa3 is D-Leu and each Xaa4 is D-Lys. In another embodiment, each Xaa1 is D-Ala(2-thienyl), each Xaa2 is D-Phe, each Xaa3 is D-Nle, and each Xaa4 is D-Arg.

In another embodiment, G is

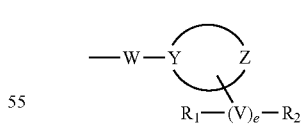

and the dipeptide Xaa3-Xaa4 is chosen from D-Leu-D-Orn and D-Nle-D-Arg. In another embodiment Xaa1Xaa2 is D-Phe-D-Phe. In another embodiment Xaa1 is D-(4-F)Phe, and Xaa2 is D-(4-Cl)Phe.

In another embodiment each Xaa1 is D-Phe or D-Ala(2-thienyl) and each Xaa2 is D-(4-Cl)Phe. In another embodiment, each Xaa3 is D-Leu or D-Nle.

In another embodiment G is and Xaa1 is chosen from D-Phe, D-(4-F)Phe, D-(2-F)Phe, cyclopentyl D-Ala, 2-thienyl D-Ala, Xaa2 is chosen from D-Phe, D-(4-F)Phe, D-(4-Cl)Phe, D-1Nal, D-2Nal, and D-Trp, and Xaa3-Xaa4 is chosen from D-Nle-D-Arg, D-Leu-D-Lys and D-Leu-D-Orn.

In one embodiment Xaa1 is (A)(A')D-Phe, and in one aspect, each Xaa1 is D-Phe. In another embodiment each Xaa2 is D-Phe. In another embodiment, each Xaa3 is chosen from D-Nle, and D-Leu, In another embodiment each Xaa4 is chosen from δ(B)2D-Orn, D-Lys and D-Arg. In one aspect, each Xaa4 is δ(B)2D-Orn and each (B) chosen from —H, methyl and isopropyl. In another aspect each Xaa4 is (B)2D-Orn, wherein one (B) is H, and the other (B) selected from the group consisting of methyl and isopropyl. In another particular aspect each Xaa4 is D-Orn.

In another embodiment each Xaa4 is chosen from ε(B) 2D-Lys, (B)2D-Arg, and δ-(B)2D-Orn. In another particular aspect each Xaa4 is chosen from D-Arg, (Et)2D-Arg, and δ-(B)D-Orn, and (B) is H, Me, iPr, or Bu.

In another embodiment G is

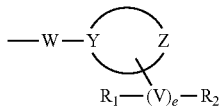

and W is null.

In another embodiment G is

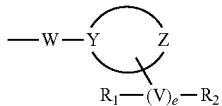

and W is —N—(CH2)b with b equal to 0, 1, 2, 3, or 4. In one aspect b is zero and Y is a carbon atom. In another aspect b is 1 or 2 and Y is a nitrogen atom. In another embodiment W is —N—(CH2)c—O—. In one particular aspect c is 1 or 2. In another aspect the Y and Z-containing ring moiety is a four or five membered ring and Y is a nitrogen atom. In another embodiment the Y and Z-containing ring moiety is a four or five membered ring and Y is a carbon atom.

In another embodiment the Y and Z-containing ring moiety is a six or seven membered ring, Y is nitrogen and Z is a carbon atom. In another alternative, the Y and Z-containing ring moiety is a six membered ring. In one aspect the Y and Z-containing ring moiety is a seven membered ring. In still another aspect the Y and Z-containing ring moiety is a six or seven membered ring and both Y and Z are nitrogen atoms.

In another embodiment e is zero and R1 and R2 are bonded directly to the same ring atom. In one aspect e is zero, R2 is —H and R1 is bonded directly to a carbon ring atom adjacent to Z. In another aspect R1 is H, amidino, C1-C3 alkyl substituted amidino, C1-C3 alkyl, dihydroimidazole, D-Pro, D-Pro amide, or —CONH2 and wherein e is zero and R2 is —H. In another aspect R1 is —H, amidino, or methyl amidino. In one aspect the Y and Z-containing ring moiety is a five membered ring, e is zero and R1 is —COOH.

In another embodiment G is

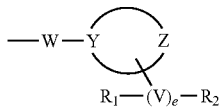

and Xaa1 is D-Phe, Xaa2 is D-Phe, Xaa3 is D-Leu, Xaa4 is ε(B)2D-Lys, or δ-(B)2D-Orn, wherein (B) is —H, methyl, or isopropyl; further wherein W is null, the Y and Z-containing ring moiety is a six or seven membered ring, Y is a nitrogen atom, e is zero, R1 is —NH2, amidino, C1-C3 alkyl, C1-C3 alkyl-substituted amidino, dihydroimidazole, D-Pro, or D-Pro amide, and R2 is H or —COOH.

In certain embodiments, there are two independent occurrences of the residues Xaa1, Xaa2, Xaa3 and Xaa4. For instance, in embodiments having the formula:

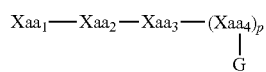

wherein G is:

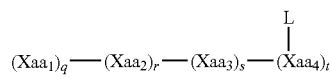

and one or more of q, r, and s is 1 or both p and t are 1, then there are two occurrences of Xaa1, Xaa2, Xaa3 and Xaa4 respectively. In such embodiments, each instance of each of the residues Xaa1, Xaa2, Xaa3 and Xaa4 can be identical.

Alternatively, and in other embodiments, each instance of one or more of the pairs of residues Xaa1, Xaa2, Xaa3 or Xaa4 can be different. For example, one instance of Xaa1 can be D-phenylalanine, while the second instance of Xaa1 in the same molecule can be a different Xaa1 residue, such as D-(4-F)phenylalanine. Similarly, one instance of Xaa2 can be D-phenylalanine, while the second instance of Xaa2 in the same molecule can be D-Ala(2-thienyl). Likewise, one instance of Xaa3 can be D-norleucine, while the second instance of Xaa3 in the same molecule can be D-leucine. In the same manner, one instance of Xaa4 can be D-ornithine, while the second instance of Xaa4 in the same molecule can be D-arginine, and so on.

In one embodiment, Xaa1 is D-Ala(2-thienyl). In another embodiment Xaa1 is D-(4-F)phenylalanine and Xaa2 is D-(4-Cl)phenylalanine. In another embodiment each Xaa1 is D-phenylalanine or D-Ala(2-thienyl) and each Xaa2 is D-(4-Cl)phenylalanine. In another embodiment Xaa1-Xaa2 is D-phenylalanine-D-phenylalanine.

In one embodiment each Xaa3 is chosen from D-norleucine and D-leucine. In another embodiment each Xaa2 is D-phenylalanine, each Xaa3 is D-norleucine, and each Xaa4 is D-arginine. In another embodiment each Xaa3 can be D-leucine or D-norleucine.

In another embodiment Xaa4 is chosen from δ(B)2D-ornithine and D-arginine. Alternatively, each Xaa4 is δ(B) 2D-ornithine and each (B) is chosen from —H, methyl and isopropyl. In still another embodiment, each Xaa4 is (B)2D-ornithine, wherein one (B) is —H, and the other (B) chosen from methyl and isopropyl. In one aspect, each Xaa4 is (B)2D-arginine, or δ-(B)2D-ornithine. In another embodiment each Xaa4 can be a residue chosen from D-arginine, (Et)2D-arginine, and δ-(B)D-ornithine, and wherein (B) is —H, methyl, isopropyl, or butyl. In one embodiment the dipeptide Xaa3-Xaa4 is chosen from D-leucine-D-ornithine and D-norleucine-D-arginine.

In one particular embodiment the synthetic peptide amide has the formula

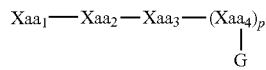

wherein G is:

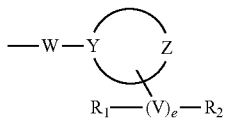

and b is zero and Y is a carbon atom. In another embodiment, b is 1 or 2 and Y is a nitrogen atom. In a particular aspect of the invention, b is 2.

In another embodiment G is

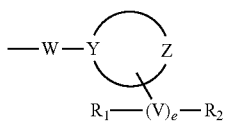

and the Y- and Z-containing moiety is [ω(4-aminopiperidine-4-carboxylic acid)]-OH. In one particular embodiment Xaa1 is chosen from D-Phe, D-(4-F)Phe, D-(2-F)Phe, cyclopentyl D-Ala, 2-thienyl D-Ala, Xaa2 is chosen from D-(4-F)Phe, D-(4-Cl)Phe, D-1Nal, D-2Nal, and D-Trp, and Xaa3-Xaa4 is chosen from D-Nle-D-Arg and D-Leu-D-Orn.

In another embodiment W is an N-alkoxyl linker of the formula: —N—(CH2)2-O—. In an alternative embodiment W is null and Xaa1Xaa2Xaa3Xaa4 is directly bonded to Y. In a second alternative embodiment, W is —NH—(CH2)2-.

In another particular embodiment, the Y and Z-containing ring moiety is a four or five membered ring and Y is a nitrogen atom. Alternatively, the Y- and Z-containing ring moiety can be a four or five membered ring wherein Y is a carbon atom. In a different embodiment, the Y and Z-containing ring moiety is a 6- or 7-membered ring, Y is a nitrogen atom and Z is a carbon atom. In one aspect of this embodiment, the Y and Z-containing ring moiety is a 6-membered ring. Alternatively, the Y and Z-containing ring moiety can be a seven membered ring. In one aspect of this embodiment, the Y and Z-containing ring moiety is a 6- or 7-membered ring and both Y and Z are nitrogen atoms.

In another particular embodiment the Y- and Z-containing ring moiety is a six or seven membered ring, or an eight-membered ring, Y is a carbon atom, and Z is a nitrogen atom. In one aspect, Y is a nitrogen atom and Z is a carbon atom. In an alternative embodiment Y and Z are each nitrogen atoms.

In another particular embodiment the Y- and Z-containing ring moiety is an optionally substituted 4-, 5-, 6-, 7-, or 8-membered heterocyclic ring moiety wherein Y is a carbon or a nitrogen atom and Z is carbon, nitrogen, oxygen, sulfur, sulfoxide, or sulfonyl; and the 4-, 5-, 6-, 7-, or 8-membered heterocyclic ring moiety is optionally singly or doubly substituted with substituents independently chosen from C1-C6 alkyl, —C1-C6 alkoxy, oxo, —OH, —Cl, —F, —NH2, —NO2, —CN, —COOH, and amidino. In one aspect when the Y- and Z-containing ring moiety is a six, seven or eight-membered ring, then Y and Z are separated by at least two ring atoms. In another aspect, when the Y- and Z-containing ring moiety is non-aromatic and Z is a carbon or a nitrogen atom, then such ring moiety includes at least one sulfur or oxygen ring heteroatom. In a particular aspect, when the Y- and Z-containing ring moiety is aromatic, then Y is a carbon atom.

In one embodiment, R1 is —H, —OH, —NH2, —COOH, C1-C3 alkyl, amidino, C1-C3 alkyl-substituted amidino, dihydroimidazole, D-Pro, D-Pro amide, or —CONH2. In another particular embodiment R2 is —H, —COOH, or C1-C3 alkyl. In one aspect, only one of R1 and R2 is a hydrogen atom. In a particular embodiment R1 is —H, D-Pro, D-Pro amide, or —NH2 and R2 is H or —COOH. In one aspect of this embodiment, R1 is —NH2 and 2 is —COOH.

In one embodiment, the operator, e is zero and R1 and R2 are bonded directly to the same ring atom. In a particular embodiment, e is zero, R2 is —H and R1 is bonded directly to a carbon ring atom adjacent to Z. In another particular embodiment, R1 is —H, amidino, C1-C3 alkyl substituted amidino, C1-C3 alkyl, dihydroimidazole, D-Pro, D-Pro amide, or —CONH2 and e is zero and R2 is —H.

In one embodiment, Xaa1 is D-Phe, Xaa2 is D-Phe, Xaa3 is D-Leu, Xaa4 is δ-(B)2D-Orn, wherein (B) is —H, methyl, or isopropyl; such that wherein W is null, the Y and Z-containing ring moiety is a six or seven membered ring, Y is a nitrogen atom, e is zero, R1 is —NH2, amidino, C1-C3 alkyl, C1-C3 alkyl-substituted amidino, dihydroimidazole, D-Pro, or D-Pro amide, and R2 is H or —COOH.

In one embodiment: Xaa1 is chosen from (A) D-Phe, (α-Me)D-Phe, D-Tyr, D-Tic, (tert-butyl)D-Gly, and β-(E)D-Ala, wherein (A) is chosen from —H, —F, —Cl, —NO2, and —CH3, and (E) is chosen from tert-butyl, cyclopentyl and thienyl; Xaa2 is chosen from (A)(A')D-Phe, D-1Nal, D-2Nal, D-Tyr, and D-Trp, wherein (A') is H or Cl; Xaa3 is chosen from D-Nle, D-Phe, (cyclopentyl) D-Ala, D-Leu, (α-Me)D-Leu, D-Hle, D-Val, and D-Met; and Xaa4 is chosen from D-Arg, (ethyl)2D-Arg, D-Nar, D-Har, (ethyl)2D-Har, F-(isopropyl)D-Lys, D-Lys, D-Amf, amidino-D-Amf, β-amidino-D-Dap, D-Dbu, D-Orn, α-(methyl)D-Orn and δ-(isopropyl)D-Orn.

In another embodiment, Xaa1 Xaa2 is D-Phe-D-Phe, Xaa3 is D-Leu or D-Nle and Xaa4 is chosen from (B)2D-Arg, D-Lys, (B)2D-Nar, (B)2D-Har, D-Dap, amidino-D-Dap, ε-(B)D-Lys, ε-(B)2-D-Lys, D-Amf, amidino-D-Amf, γ-(B)2D-Dbu and δ-(B)2α-(B')D-Orn.

In another embodiment, Xaa4 is chosen from D)-Lys, (B)2D-Har, ε(B)-D-Lys, δ(B)2-α(B')D-Orn and ε(B)2-D-Lys.

In another embodiment, G is

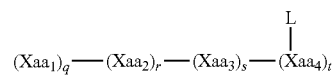

In another embodiment, the integers p, q, r, s and t are each 1.

In another embodiment, Xaa1 is chosen from (A) D-Phe, (α-Me)D-Phe, D-Tyr, D-Tic, (tert-butyl)D-Gly, and β-(E)D-Ala, wherein A is selected from the group consisting of —H, —F, —Cl, —NO2, and —CH3, and (E) is selected from the group consisting of tert-butyl, cyclopentyl and thienyl; Xaa2 is selected from the group consisting of (A)(A')D-Phe, D-1Nal, D-2Nal, D-Tyr, and D-Trp, wherein (A') is H or Cl; Xaa3 is selected from the group consisting of D-Nle, D-Phe, (cyclopentyl)D-Ala, D-Leu, (α-Me)D-Leu, D-Hle, D-Val, and D-Met; and Xaa4 is selected from the group consisting of D-Arg, (ethyl)2D-Arg, D-Nar, D-Har, (ethyl)2D-Har, ε-(isopropyl)D-Lys, D-Lys, D-Amf, amidino-D-Amf, β-amidino-D-Dap, D-Dbu, D-Orn, α-(methyl)D-Orn and δ-(isopropyl)D-Orn.

In another embodiment of the synthetic peptide amide of the invention: Xaa1 is D-Phe; Xaa2 is D-Phe; Xaa3 is D-Leu and Xaa4 is chosen from D-Nar, D-Orn, and (isopropyl)D-Orn.

In another embodiment, L is a linker chosen from ε-D-Lys, ε-Lys, δ-D-Orn, δ-Orn, 4-amino-4-carboxylic piperidine and bis(D-Lys-Gly)Lactam.

In another embodiment, G is

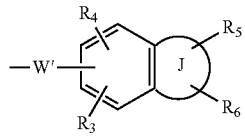

In another embodiment of the synthetic peptide amide, J is a five-membered heterocyclic ring moiety. In an alternative embodiment, J is a five-membered heterocyclic ring moiety that includes two heteroatoms, which two heteroatoms are both N.

In another embodiment of the synthetic peptide amide, G is

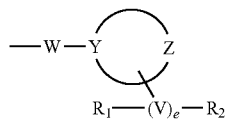

In a particular aspect of this embodiment, W is null, and Y is nitrogen. In another particular aspect of this embodiment, the Y and Z-containing ring moiety is a five-membered saturated ring.

In another embodiment of the synthetic peptide amide, G is an optionally substituted proline radical.

In another embodiment of the synthetic peptide amide, the Y and Z-containing ring moiety is a six-membered saturated ring. In a particular aspect of this embodiment, the Y and Z-containing ring moiety comprises a single heteroatom and e is zero, and R1 and R2 taken together or with one or two ring atoms of the Y and Z-containing ring moiety comprise an optionally substituted monocyclic or bicyclic 4-, 5,6-, 7,8- or 9-membered heterocyclic ring moiety. In a particular aspect of this embodiment, R1 and R2 taken together with one ring atom of the Y and Z-containing ring moiety comprises a five-membered heterocyclic ring moiety having only heteroatoms chosen from N and O, which heterocyclic ring moiety with the Y and Z-containing ring moiety forms a spiro structure.

In another embodiment of the synthetic peptide amide, the Y and Z-containing ring moiety includes two heteroatoms. In a particular aspect of this embodiment, the two heteroatoms of the Y and Z-containing ring moiety are both nitrogen. In another particular aspect of this embodiment, the integer e is zero, R2 is hydrogen and the Y- and Z-containing ring moiety is 3-substituted with R1. In still another particular aspect of this embodiment, the two heteroatoms of the Y- and Z-containing ring moiety are nitrogen and oxygen. In one particular aspect the Y- and Z-containing ring moiety is 3-substituted with R1, the integer e is zero and R2 is hydrogen. In another particular aspect the two heteroatoms of the Y- and Z-containing ring moiety are nitrogen and sulfur. In still another particular aspect the Y- and Z-containing ring moiety is 3-substituted with R1, e is zero and R2 is H.

In another embodiment of the synthetic peptide amide, G is

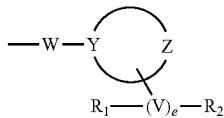

W is null, and Y is nitrogen and the Y and Z-containing ring moiety is a seven-membered saturated ring comprising two heteroatoms. In a particular aspect of this embodiment, Y and Z are both nitrogen atoms and the moiety VeR1R2 is bonded to Z. In an alternative aspect of this embodiment, Y is nitrogen and the second heteroatom of the Y and Z-containing ring moiety is chosen from S and O. In another alternative aspect of this embodiment, W is—NH2-(CH2)b- and b is zero, 1, 2, or 3. In a particular aspect the Y- and Z-containing ring moiety is a five-membered saturated ring such as for instance, an optionally substituted proline radical. Alternatively, the Y- and Z-containing ring moiety can be a six-membered saturated ring, wherein for example, Y can be carbon and Z can be nitrogen; alternatively, Y and Z can both be nitrogen atoms.

In another embodiment of the synthetic peptide amide, G is chosen from substituted piperidinyl, piperidinyl forming a spiro structure with an optionally substituted heterocycle, piperidinyl fused with an optionally substituted heterocycle, substituted piperazinyl, 4-sulfonamidyl piperazinyl, 3-substituted piperazinyl, substituted homopiperazinyl, optionally substituted homomorpholinyl, optionally substituted homothiomorpholinyl, 3-substituted morpholinyl, 3-substituted thiomorpholinyl, 4-4 dioxo thiomorpholinyl, and optionally substituted proline, and W is null; or

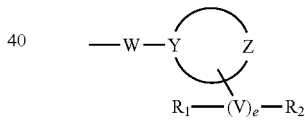

G is
wherein the moiety

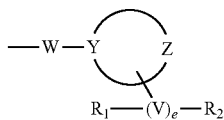

is chosen from substituted pyrazinyl, substituted pyridinyl, substituted piperazinyl, optionally substituted pyrimidinyl, substituted "reverse" piperidinyl (i.e. not bonded to W through the ring nitrogen), optionally substituted heterocyclic bicycle, optionally substituted proline, optionally substituted thiazolyl, optionally substituted dioxolanyl, and optionally substituted tetrahydropyranyl, and W is—NH2-(CH2)b- and b is zero, 1, 2, or 3.

In another embodiment of the synthetic peptide amide, G is chosen from substituted piperidinyl, piperidinyl forming a Spiro structure with an optionally substituted heterocycle, and piperidinyl fused with an optionally substituted heterocycle. In a particular aspect of this embodiment, G is chosen from substituted piperazinyl, 4-sulfonamidyl piperazinyl, 3-substituted piperazinyl, and substituted homopiperazinyl. In another alternative aspect, G is chosen from optionally substituted homomorpholinyl, optionally substituted homothiomorpholinyl, 3-substituted morpholinyl, 3-substituted thiomorpholinyl, and 4-4 dioxothiomorpholinyl. In still another alternative aspect, G is an optionally substituted proline.

In another embodiment of the synthetic peptide amide, W is —NH2-(CH2)b-, b is zero, 1, 2, or 3 and the moiety

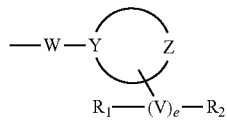

is chosen from optionally substituted thiazolyl, optionally substituted dioxolanyl, and optionally substituted tetrahydropyranyl. Alternatively, W is —NH2-(CH2)b-, b is zero, 1, 2, or 3 and the moiety

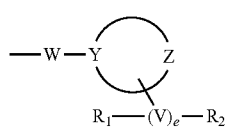

is chosen from substituted pyrazinyl, substituted pyridinyl, optionally substituted pyrimidinyl, and optionally substituted heterocyclic bicycle. In another alternative, W is —NH2-(CH2)b-, b is zero, 1, 2, or 3 and the moiety

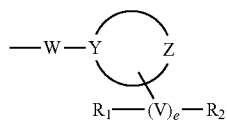

is chosen from substituted piperazinyl and 4-substituted piperidinyl.

In another embodiment of the synthetic peptide amide, W is —NH2-(CH2)b-, b is zero, 1, 2, or 3 and the moiety

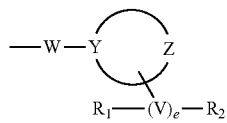

is an optionally substituted proline moiety.

In another embodiment of the synthetic peptide amide, e is zero and R1 and R2 are bonded directly to the same ring atom.

In yet another alternative embodiment of the synthetic peptide amide, R1 is chosen from H, OH, —NH2, —COOH, —CH2COOH, C1-C3 alkyl, amidino, C1-C3 alkyl-substituted amidino, dihydroimidazole, D-Pro, D-Pro amide, and CONH2 and R2 is H, —COOH, or C1-C3 alkyl.

Specific compounds of group (dd), as disclosed in U.S. Pat. No. 7,713,937, include compounds 1-103 shown below:

Compound (1): D-Phe-D-Phe-D-Leu-(ε-Me)D-Lys-[4-amidinohomopiperazine amide]:

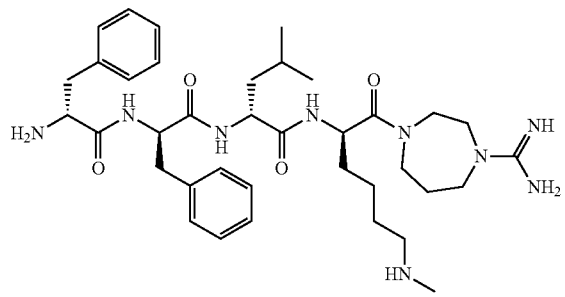 [SMILES: CNCCCC[C@@H](NC(=O)[C@@H](CC(C)C)NC(=O)[C@@H](Cc1ccccc1)NC(=O)[C@H](N)Cc1ccccc1)C(=O)N1CCCN(C(=N)N)CC1]

Compound (2): D-Phe-D-Phe-D-Leu-D-Lys-[ω(4-aminopiperidine-4-carboxylic acid)]-OH:

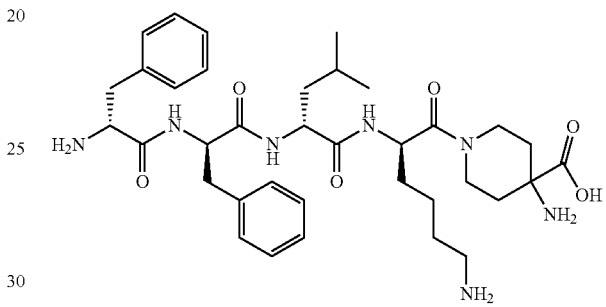

Compound (3): D-Phe-D-Phe-D-Leu-(α-Me)D-Lys-[ω(4-aminopiperidine-4-carboxylic acid)]-OH:

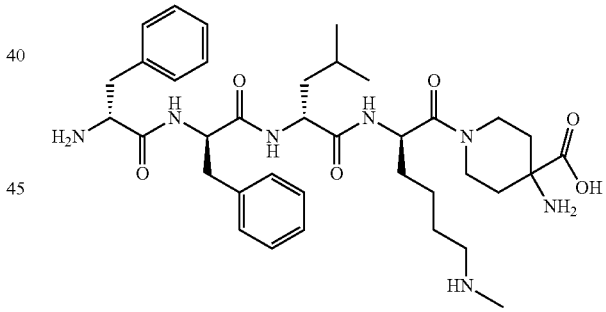

Compound (4): D-Phe-D-Phe-D-Leu-D-Lys-[N-(4-piperidinyl)-L-proline]-OH:

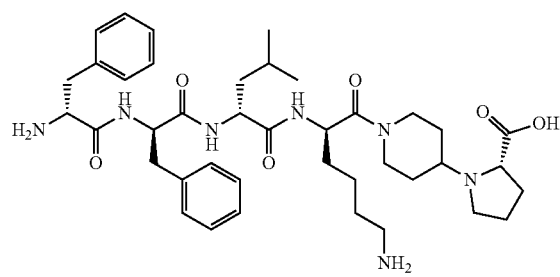 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC(N2CCC[C@H]2C(=O)O)CC1]

Compound (5): D-Phe-D-Phe-D-Leu-D-Har-[N-(4-piperidinyl)-L-proline]-OH:

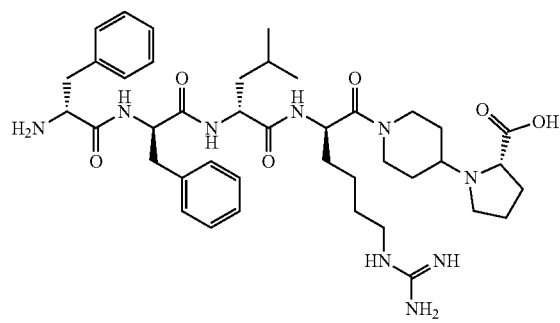 [SMILES: CC(C)C[C@@H](NC(=O)[C@@H](Cc1ccccc1)NC(=O)[C@H](N)Cc1ccccc1)C(=O)N[C@H](CCCCNC(=N)N)C(=O)N1CCC(N2CCC[C@H]2C(=O)O)CC1]

Compound (6): D-Phe-D-Phe-D-Leu-(ε-Me)D-Lys-[N-(4-piperidinyl)-L-proline]-OH:

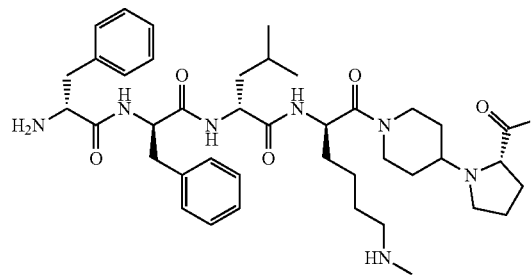

Compound (7): D-Phe-D-Phe-D-Leu-D-Arg-[homopiperazine amide]:

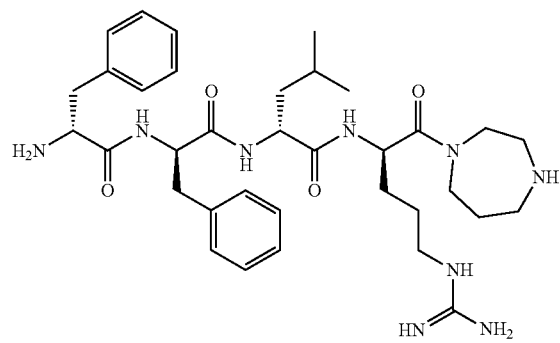 [SMILES: CC(C)C[C@@H](NC(=O)[C@@H](Cc1ccccc1)NC(=O)[C@H](N)Cc1ccccc1)C(=O)N[C@H](CCCNC(=N)N)C(=O)N1CCCNCC1]

Compound (8): D-Phe-D-Phe-D-Leu-D-Har-[ω(4-aminopiperidine-4-carboxylic acid)]-OH:

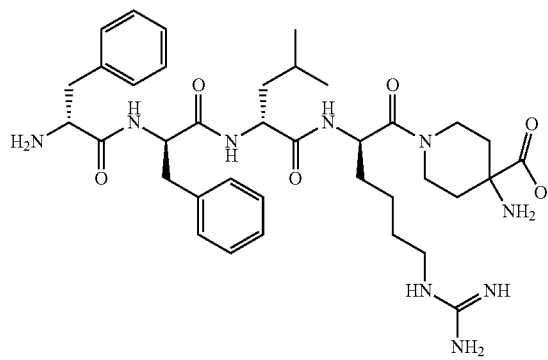

Compound (9): D-Phe-D-Phe-D-Leu-(ε-iPr)D-Lys-[ω(4-aminopiperidine-4-carboxylic acid)]-OH:

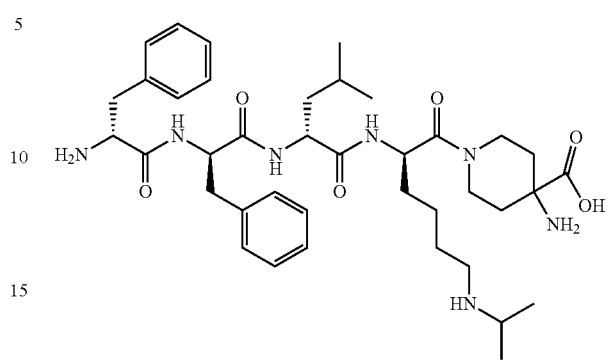

Compound (10): D-Phe-D-Phe-D-Leu-(β-amidino)D-Dap-[ω(4-aminopiperidine-4-carboxylic acid)]-OH:

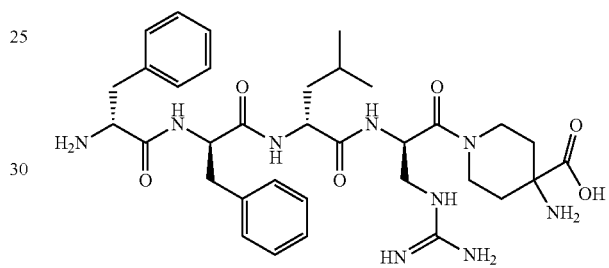

Compound (11): D-Phe-D-Phe-D-Leu-D-Nar-[ω(4-aminopiperidine-4-carboxylic acid)]-OH:

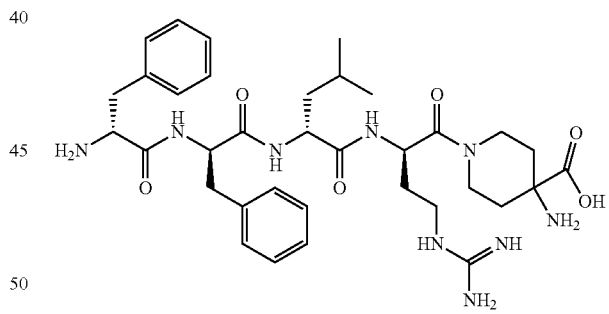

Compound (12): D-Phe-D-Phe-D-Leu-D-Dbu-[N-(4-piperidinyl)-L-proline]-OH:

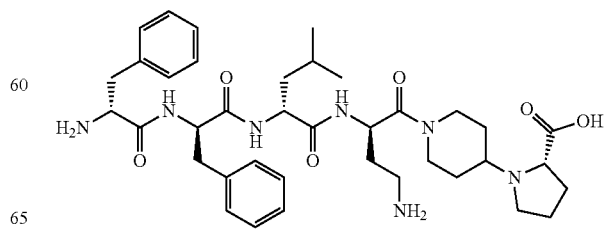

Compound (13): D-Phe-D-Phe-D-Leu-D-Nar-[N-(4-piperidinyl)-L-proline]-OH:

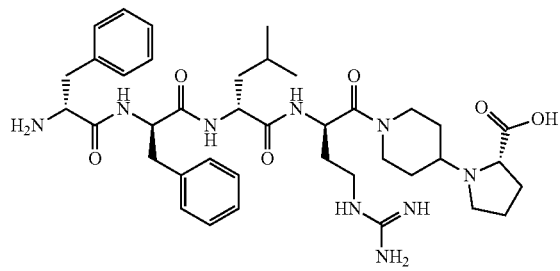 [SMILES: CC(C)C[C@@H](NC(=O)[C@@H](Cc1ccccc1)NC(=O)[C@H](N)Cc1ccccc1)C(=O)N[C@H](CCNC(=N)N)C(=O)N1CCC(N2CCC[C@H]2C(=O)O)CC1]

Compound (14): D-Phe-D-Phe-D-Leu-D-Dap(amidino)-[N-(4-piperidinyl)-L-proline]-OH:

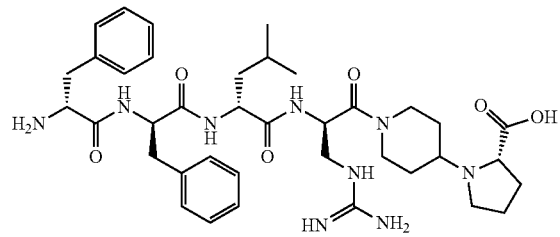 [SMILES: CC(C)C[C@@H](NC(=O)[C@@H](Cc1ccccc1)NC(=O)[C@H](N)Cc1ccccc1)C(=O)N[C@H](CNC(=N)N)C(=O)N1CCC(N2CCC[C@H]2C(=O)O)CC1]

Compound (15): D-Phe-D-Phe-D-Leu-D-Lys-[4-amidino-homopiperazine amide]:

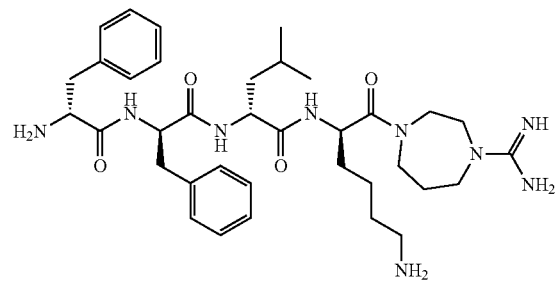 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCCN(C(=N)N)CC1]

Compound (16): D-Phe-D-Phe-D-Leu-D-Har-[4-amidino-homopiperazine amide]:

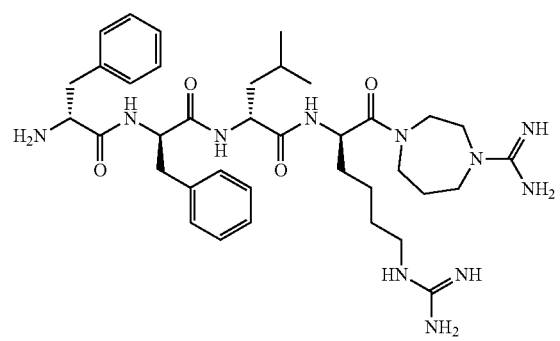 [SMILES: CC(C)C[C@@H](NC(=O)[C@@H](Cc1ccccc1)NC(=O)[C@H](N)Cc1ccccc1)C(=O)N[C@H](CCCCNC(=N)N)C(=O)N1CCCN(C(=N)N)CC1]

Compound (17): D-Phe-D-Phe-D-Leu-(ε-iPr)D-Lys-[4-amidinohomo-piperazine amide]:

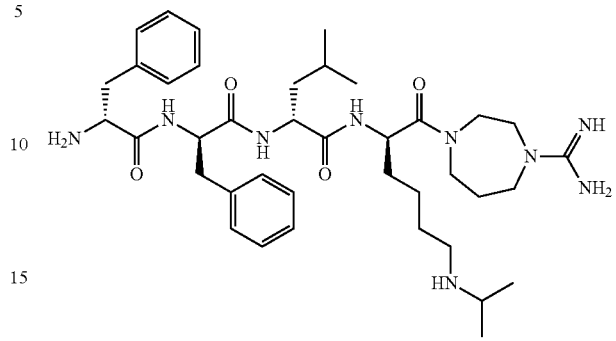

Compound (18): D-Phe-D-Phe-D-Leu-(β-amidino)D-Dap-[4-amidinohomopiperazine amide]:

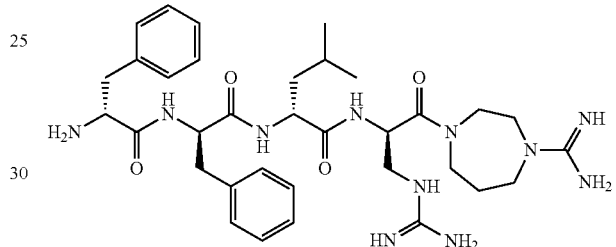

Compound (19): D-Phe-D-Phe-D-Nle-(β-amidino)D-Dap-[4-amidinohomopiperazine amide]:

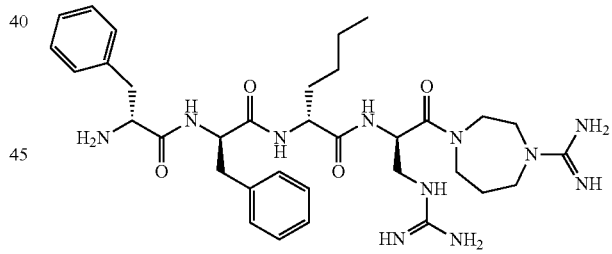

Compound (20): D-Phe-D-Phe-D-Leu-(β-amidino)D-Dap-[homopiperazine amide]:

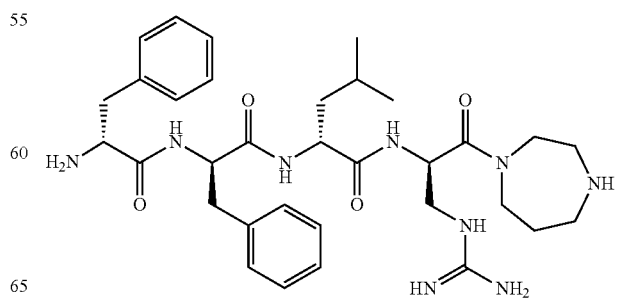

Compound (21): D-Phe-D-Phe-D-Nle-(β-amidino)D-Dap-[homopiperazine amide]:

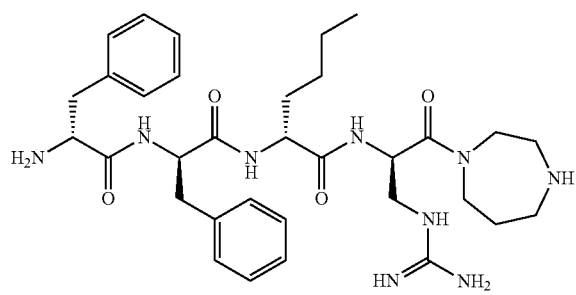 [SMILES: CCCC[C@@H](NC(=O)[C@@H](Cc1ccccc1)NC(=O)[C@H](N)Cc1ccccc1)C(=O)N[C@H](CNC(=N)N)C(=O)N1CCCNCC1]

Compound (22): D-Phe-D-Phe-D-Leu-D-Dbu-[4-amidino-homopiperazine amide]:

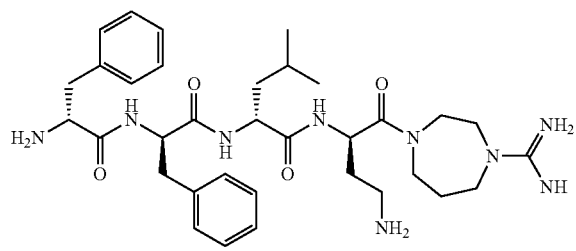 [SMILES: CC(C)C[C@@H](NC(=O)[C@@H](Cc1ccccc1)NC(=O)[C@H](N)Cc1ccccc1)C(=O)N[C@H](CCN)C(=O)N1CCCN(C(=N)N)CC1]

Compound (23): D-Phe-D-Phe-D-Leu-D-Nar-[4-amidino-homopiperazine amide]:

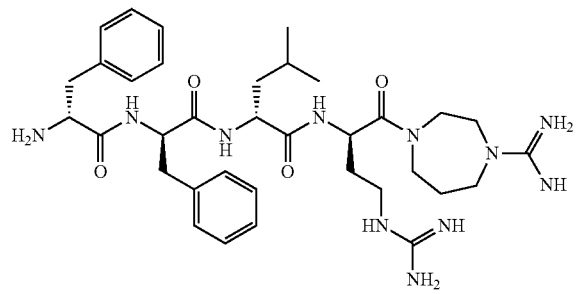 [SMILES: CC(C)C[C@@H](NC(=O)[C@@H](Cc1ccccc1)NC(=O)[C@H](N)Cc1ccccc1)C(=O)N[C@H](CCNC(=N)N)C(=O)N1CCCN(C(=N)N)CC1]

Compound (24): D-Phe-D-Phe-D-Leu-D-Arg-[4-amidino-homopiperazine amide]:

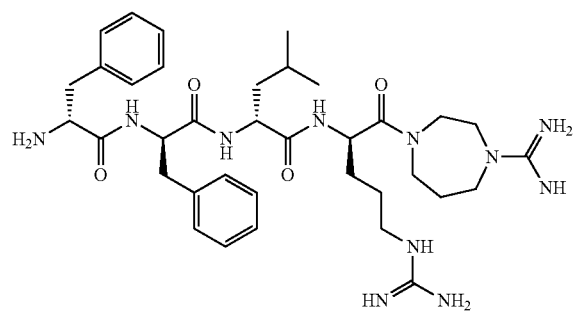 [SMILES: CC(C)C[C@@H](NC(=O)[C@@H](Cc1ccccc1)NC(=O)[C@H](N)Cc1ccccc1)C(=O)N[C@H](CCCNC(=N)N)C(=O)N1CCCN(C(=N)N)CC1]

Compound (25): D-Phe-D-Phe-D-Leu-D-Lys-[2,8-diazaspiro[4,5]decan-1one amide]:

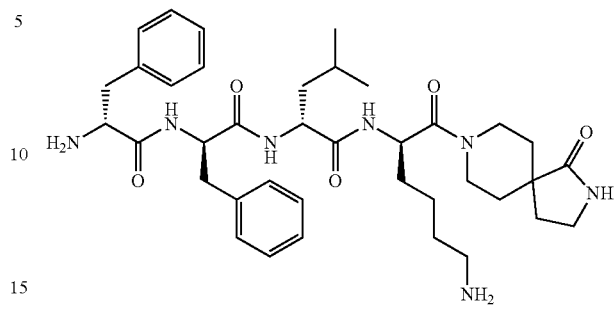

Compound (26): D-Phe-D-Phe-D-Leu-D-Lys-[2-methyl-2,8-diazaspiro[4,5]decan-1-one amide]:

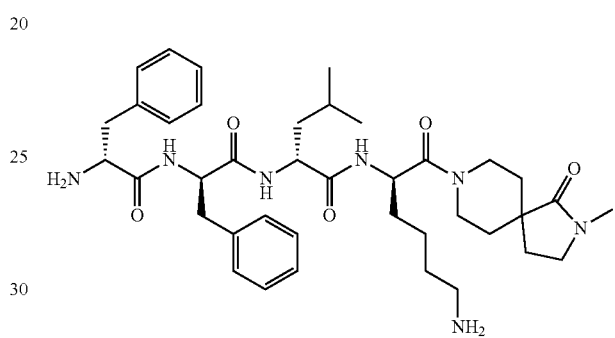

Compound (27): D-Phe-D-Phe-D-Leu-D-Lys-[1,3,8-triazaspiro[4,5]decane-2,4-dione amide]:

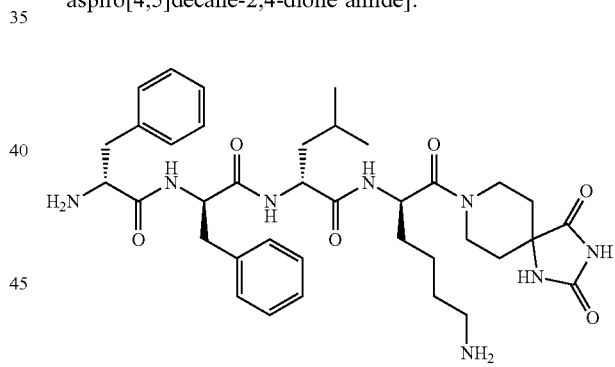

Compound (28): D-Phe-D-Phe-D-Leu-D-Lys-[5-chloro-1-(piperidin-4-yl)-1H-benzo[d]imidazol-2(3)H-one amide]:

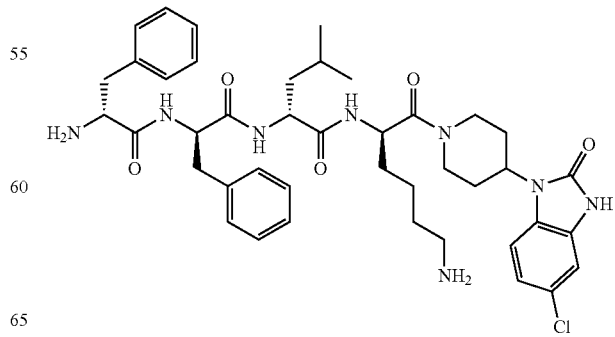

Compound (29): D-Phe-D-Phe-D-Leu-D-Lys-[morpholino (piperidin-4-yl)methanone amide]:

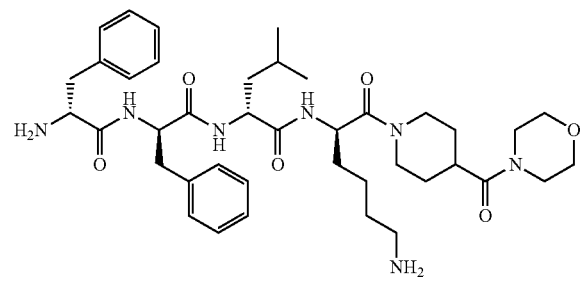 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC(C(=O)N2CCOCC2)CC1]

Compound (30): D-Phe-D-Phe-D-Leu-D-Lys-[4-phenyl-1-(piperidin-yl-1H-imidazol-2(3H)-one amide]:

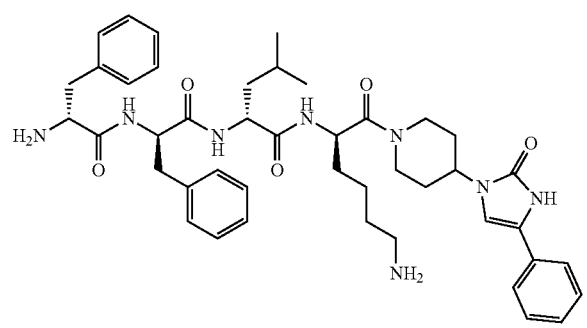 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC(n2cc(-c3ccccc3)[nH]c2=O)CC1]

Compound (31): D-Phe-D-Phe-D-Leu-D-Lys-[4-(3,5-dimethyl-4H-1,2,4-triazol-4-yl)piperidine amide]:

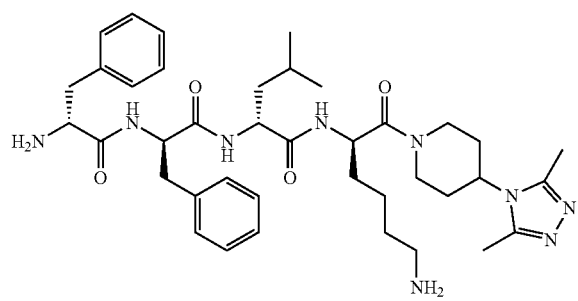 [SMILES: Cc1nnc(C)n1C1CCN(C(=O)[C@@H](CCCCN)NC(=O)[C@@H](CC(C)C)NC(=O)[C@@H](Cc2ccccc2)NC(=O)[C@H](N)Cc2ccccc2)CC1]

Compound (32): D-Phe-D-Phe-D-Leu-D-Lys-[1-(piperidin-4-yl)indolin-2-one amide]:

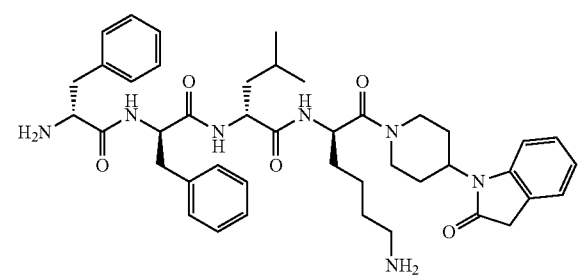 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC(N2C(=O)Cc3ccccc32)CC1]

Compound (33): D-Phe-D-Phe-D-Leu-D-Lys-[1-phenyl-1,3,8-triazaspiro[4.5]decan-4-one amide]:

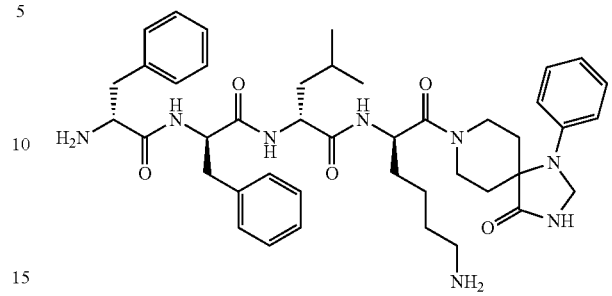

Compound (34): D-Phe-D-Phe-D-Leu-D-Lys-[imidazo[1,2-a]pyridine-2-ylmethyl amide]:

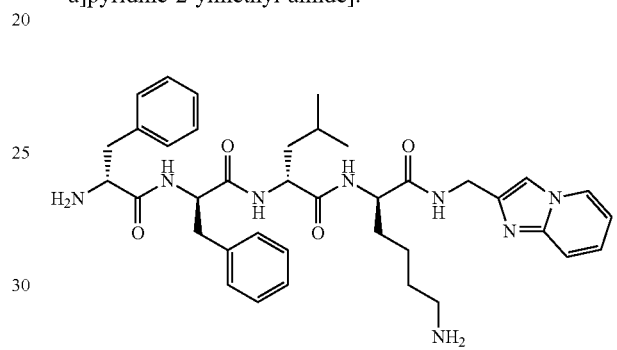

Compound (35) D-Phe-D-Phe-D-Leu-D-Lys-[(5-methylpyrazin-2-yl)methyl amide]:

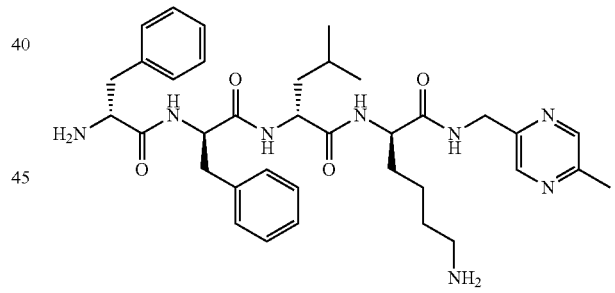

Compound (36): D-Phe-D-Phe-D-Leu-D-Lys-[1-(piperidin-4-yl)-1H-benzo[d]imidazol-2(3H)-one amide]:

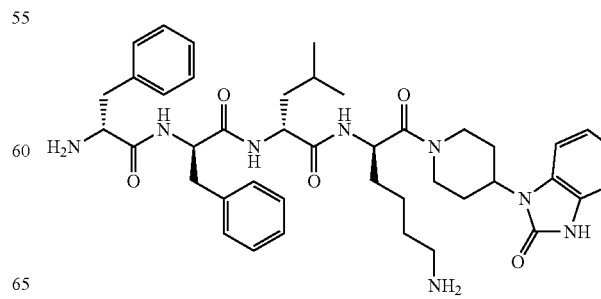

Compound (37): D-Phe-D-Phe-D-Leu-D-Lys-[4,5,6,7-tetra-hydro-1H-pyrazolo[4,3-c]pyridine amide]:

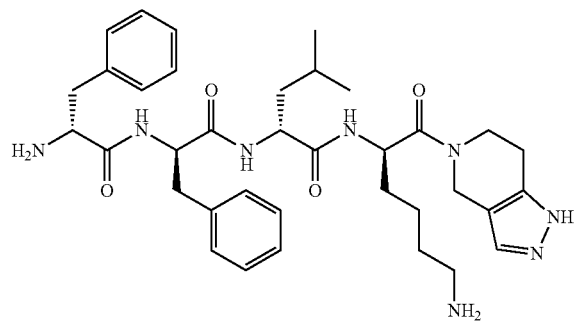 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCc2[nH]ncc2C1]

Compound (38): D-Phe-D-Phe-D-Leu-D-Orn-[4-(2-amino-ethyl)-1-carboxymethyl-piperazine]-OH:

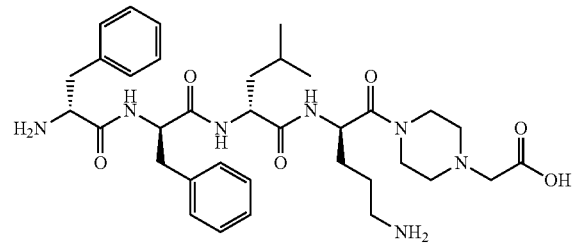 [SMILES: CC(C)C[C@@H](NC(=O)[C@@H](Cc1ccccc1)NC(=O)[C@H](N)Cc1ccccc1)C(=O)N[C@H](CCCN)C(=O)N1CCN(CC(=O)O)CC1]

Compound (39) D-Phe-D-Phe-D-Leu-D-Orn-[4-carboxym-ethyl-piperidine]-OH:

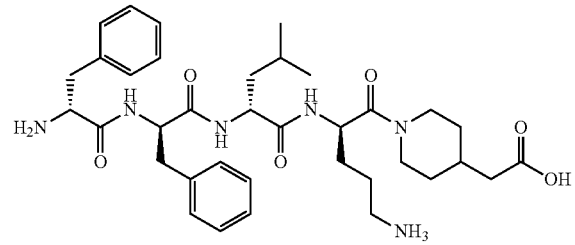 [SMILES: CC(C)C[C@@H](NC(=O)[C@@H](Cc1ccccc1)NC(=O)[C@H](N)Cc1ccccc1)C(=O)N[C@H](CCCN)C(=O)N1CCC(CC(=O)O)CC1]

Compound (40) D-Phe-D-Phe-D-Nle-D-Arg-D-Pro-OH:

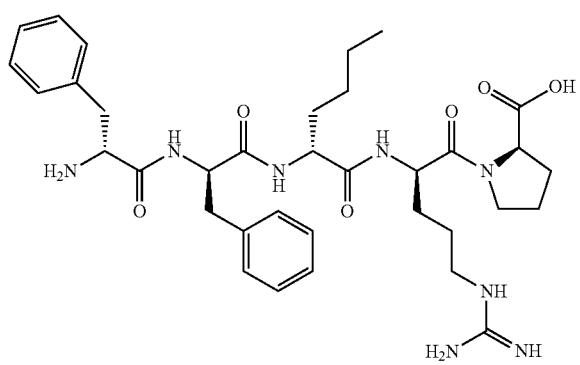 [SMILES: CCCC[C@@H](NC(=O)[C@@H](Cc1ccccc1)NC(=O)[C@H](N)Cc1ccccc1)C(=O)N[C@H](CCCNC(=N)N)C(=O)N1CCC[C@@H]1C(=O)O]

Compound (41) D-Phe-D-Phe-D-Leu-D-Orn-[(2S,4-R)-4-amino-pyrrolidine-2-carboxylic acid]-OH:

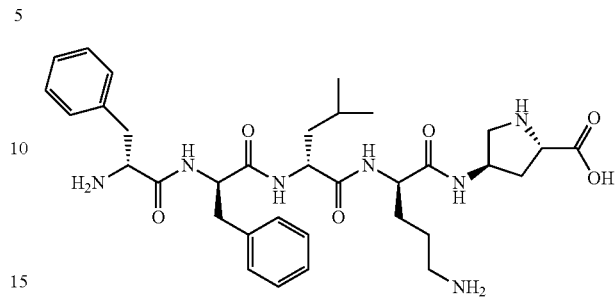

Compound (42) D-Phe-D-Phe-D-Leu-D-Orn-[(2S,4S)-4-amino-pyrrolidine-2-carboxylic acid]-OH:

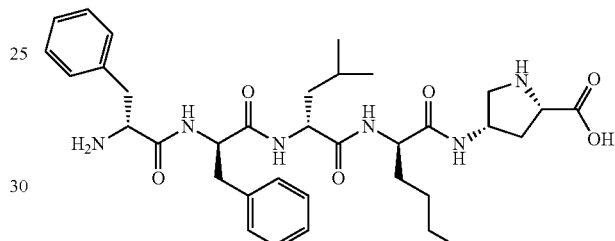

Compound (43) D-Phe-D-Phe-D-Leu-D-Orn-[ω(4-aminopi-peridine-4-carboxylic acid)]-OH:

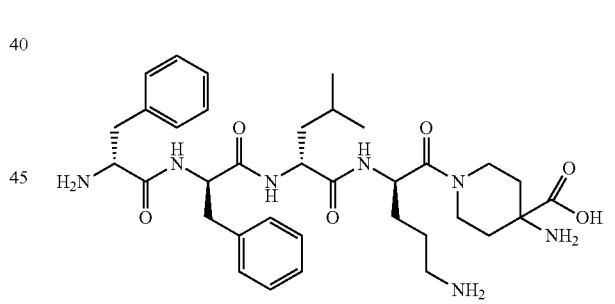

Compound (44) D-Phe-D-Phe-D-Leu-D-Orn-[ω(D/L-2-amino-3-(4-N-piperidinyl)propionic acid)]-OH:

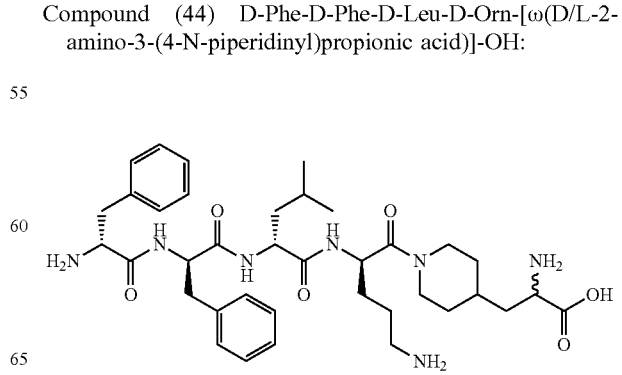

Compound (45) D-Phe-D-Phe-D-Leu-D-Orn-[ω(D/L-4-piperazine-2-carboxylic acid)]-OH:
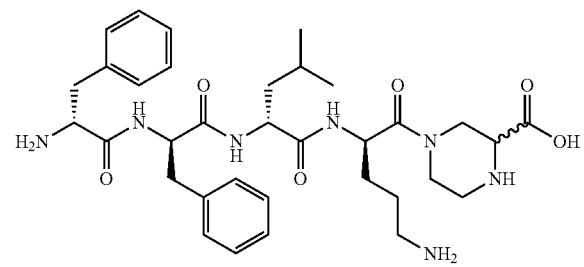 [SMILES: CC(C)C[C@@H](NC(=O)[C@@H](Cc1ccccc1)NC(=O)[C@H](N)Cc1ccccc1)C(=O)N[C@H](CCCN)C(=O)N1CCNC(C(=O)O)C1]
Compound (46) D-Phe-D-Phe-D-Leu-D-Orn-[Isonipecotic acid]-OH:
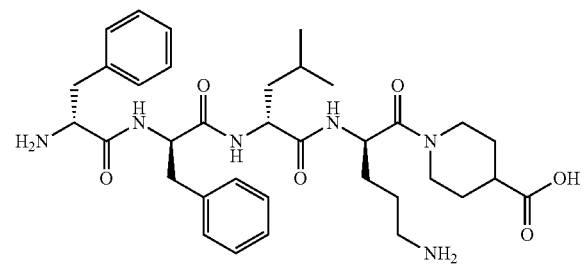 [SMILES: CC(C)C[C@@H](NC(=O)[C@@H](Cc1ccccc1)NC(=O)[C@H](N)Cc1ccccc1)C(=O)N[C@H](CCCN)C(=O)N1CCC(C(=O)O)CC1]
Compound (47) D-Phe-D-Phe-D-Leu-D-Orn-[N-(4-piperidinyl)-L-proline]-OH:
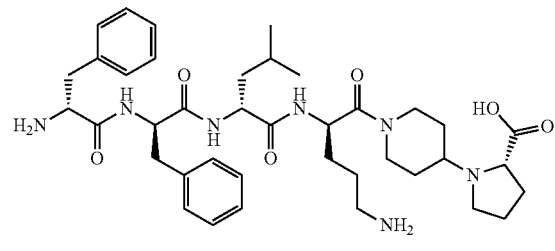 [SMILES: CC(C)C[C@@H](NC(=O)[C@@H](Cc1ccccc1)NC(=O)[C@H](N)Cc1ccccc1)C(=O)N[C@H](CCCN)C(=O)N1CCC(N2CCC[C@H]2C(=O)O)CC1]
Compound (48) D-Phe-D-Phe-D-Leu-D-Orn-[4-(4-piperidinyl)-butanoic acid]-OH:
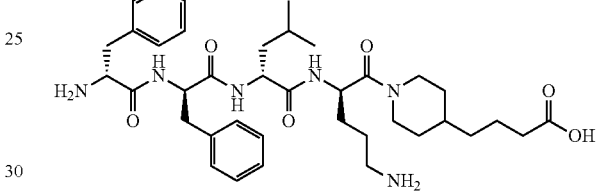
Compound (49) D-Phe-D-Phe-D-Leu-D-Orn-[4-(2-aminoethyl)-1-carboxymethyl-piperazine]-NH2:
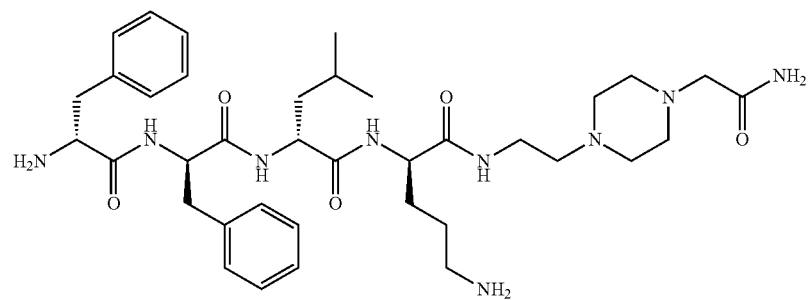 [SMILES: CC(C)C[C@@H](NC(=O)[C@@H](Cc1ccccc1)NC(=O)[C@H](N)Cc1ccccc1)C(=O)N[C@H](CCCN)C(=O)NCCN1CCN(CC(N)=O)CC1]
Compound (50) D-Phe-D-Phe-D-Leu-D-Orn-[N-(4-piperidinyl)-L-proline]-NH2:
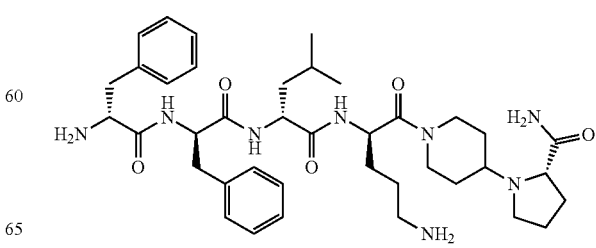

Compound (51) D-Phe-D-Phe-D-Leu-D-Orn-[4-amino-1-carboxymethyl-piperidine]-NH2:

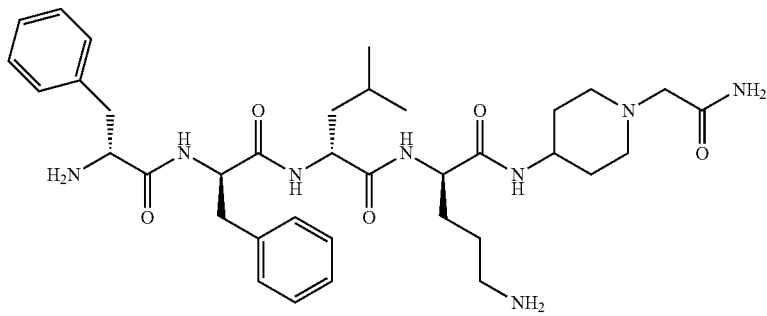 [SMILES: CC(C)C[C@@H](NC(=O)[C@@H](Cc1ccccc1)NC(=O)[C@H](N)Cc1ccccc1)C(=O)N[C@H](CCCN)C(=O)NC1CCN(CC(N)=O)CC1]

Compound (52) D-Phe-D-Phe-D-Leu-D-Orn-[4-(N-methyl)amidino-homopiperazine amide]:

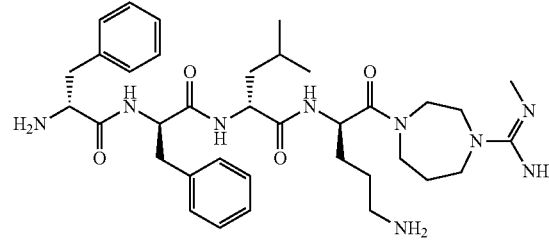

Compound (53) D-Phe-D-Phe-D-Leu-D-Orn[4-amidinohomopiperazine amide]:

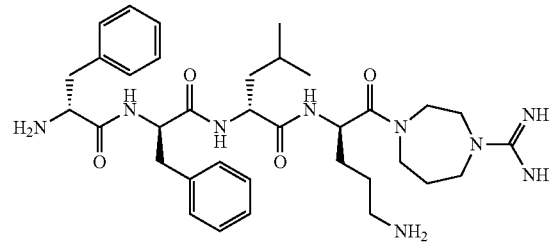 [SMILES: CC(C)C[C@@H](NC(=O)[C@@H](Cc1ccccc1)NC(=O)[C@H](N)Cc1ccccc1)C(=O)N[C@H](CCCN)C(=O)N1CCCN(C(=N)N)CC1]

Compound (54) D-Phe-D-Phe-D-Leu-D-Orn-[4-(4,5-dihydro-1H-imidazol-2-yl)homopiperazine amide]:

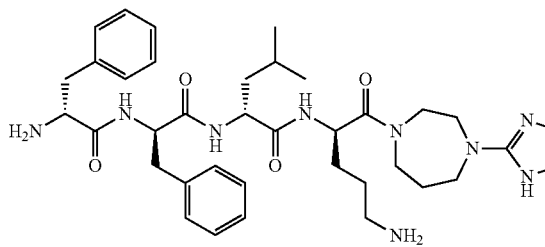

Compound (55) D-Phe-D-Phe-D-Leu-D-Orn-[4-ethylhomopiperazine amide]:

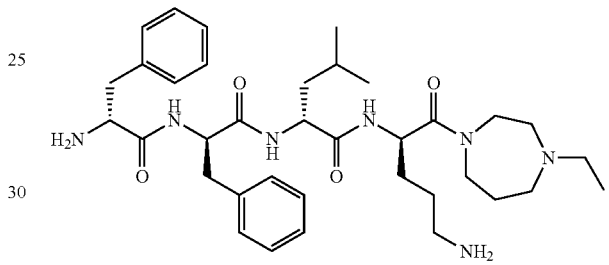

Compound (56) D-Phe-D-Phe-D-Leu-D-Orn-[homopiperazine amide]:

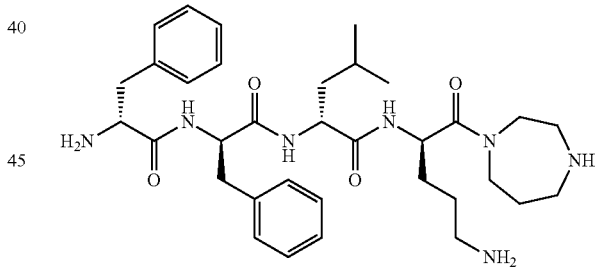

Compound (57) D-Phe-D-Phe-D-Leu-(8-Me)D-Orn-[4-amidinohomopiperazine amide]:

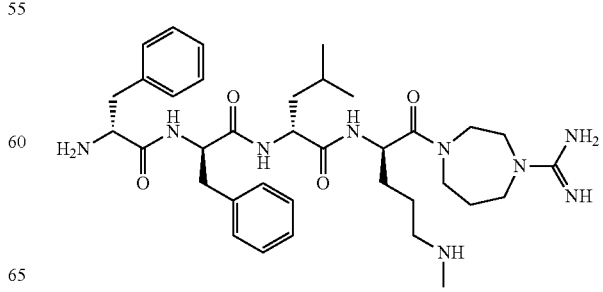

Compound (58) D-Phe-D-Phe-D-Leu-(δ-iPr)D-Orn-[ω(4-aminopipeidine-4-carboxylic acid)]-OH:

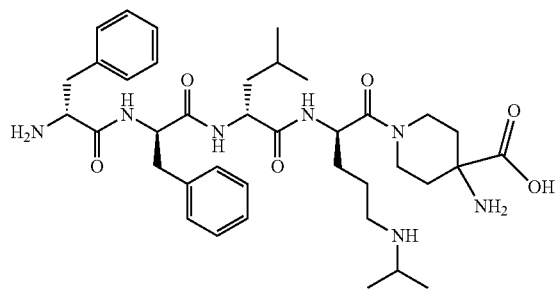 [SMILES: CC(C)C[C@@H](NC(=O)[C@@H](Cc1ccccc1)NC(=O)[C@H](N)Cc1ccccc1)C(=O)N[C@H](CCCNC(C)C)C(=O)N1CCC(N)(C(=O)O)CC1]

Compound (59) D-Phe-D-Phe-D-Leu-(δ-iPr)D-Orn-[4-amidinohomopiperazine amide]:

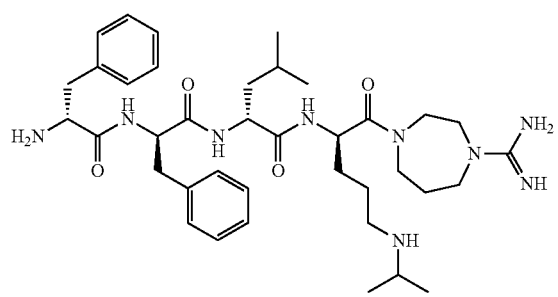 [SMILES: CC(C)C[C@@H](NC(=O)[C@@H](Cc1ccccc1)NC(=O)[C@H](N)Cc1ccccc1)C(=O)N[C@H](CCCNC(C)C)C(=O)N1CCCN(C(=N)N)CC1]

Compound (60) D-Phe-D-Phe-D-Leu-(δ-Me)D-Orn-[homopiperazine amide]:

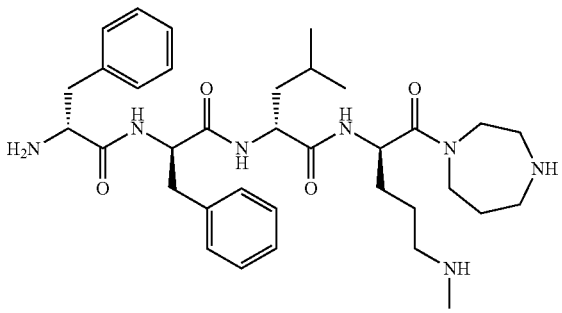 [SMILES: CNCCC[C@@H](NC(=O)[C@@H](CC(C)C)NC(=O)[C@@H](Cc1ccccc1)NC(=O)[C@H](N)Cc1ccccc1)C(=O)N1CCCNCC1]

Compound (61) D-Phe-D-Phe-D-Leu-(δ-iPr)D-Orn-[homopiperazine amide]:

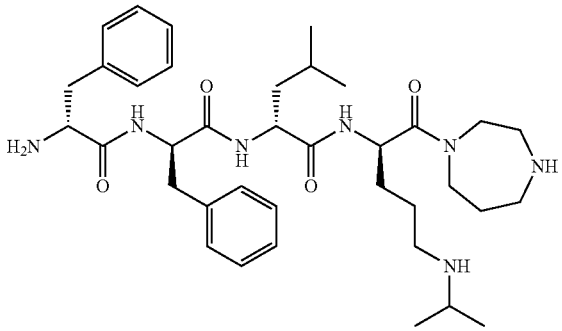 [SMILES: CC(C)C[C@@H](NC(=O)[C@@H](Cc1ccccc1)NC(=O)[C@H](N)Cc1ccccc1)C(=O)N[C@H](CCCNC(C)C)C(=O)N1CCCNCC1]

Compound (62): D-Phe-D-Phe-D-Leu-D-Lys-[1,3-dioxolan-2-yl)methanamine amide]:

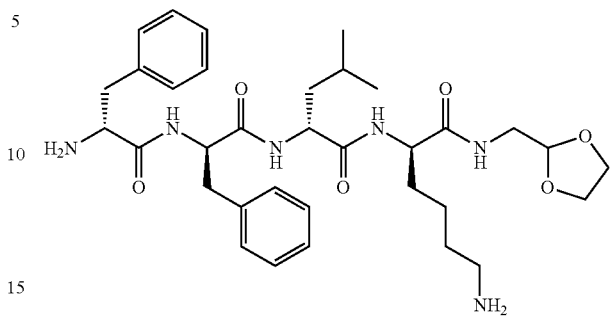

Compound (63): D-Phe-D-Phe-D-Leu-D-Lys-[2-(piperazin-1-yl)pyrimidine amide]:

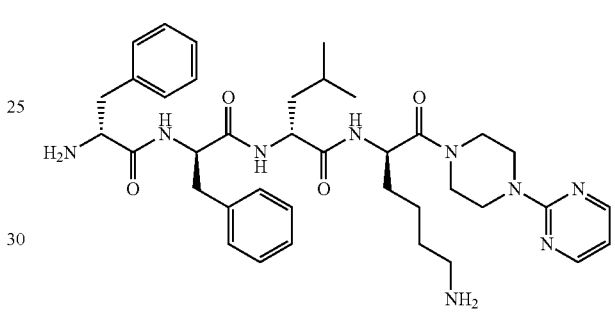

Compound (64): D-Phe-D-Phe-D-Leu-D-Lys-[2-(piperazin-1-yl)pyrazine amide]:

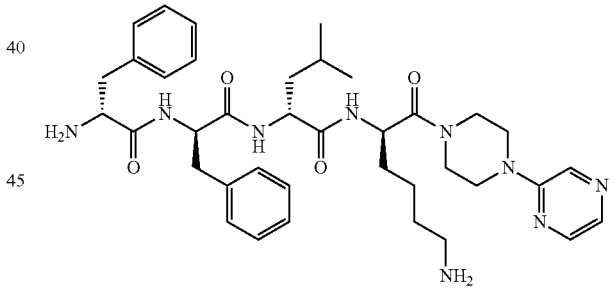

Compound (65): D-Phe-D-Phe-D-Leu-D-Lys-[1-(pyridin-2-yl)piperazine amide]:

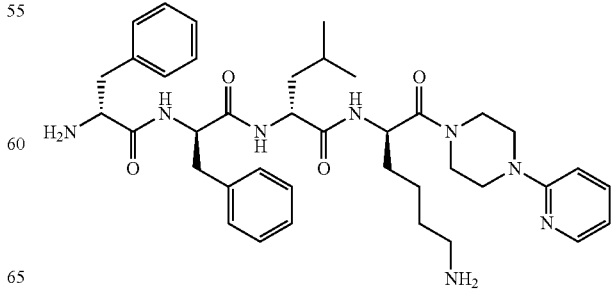

Compound (66): D-Phe-D-Phe-D-Leu-D-Lys-[2-(piperazin-1-yl)thiazole amide]:

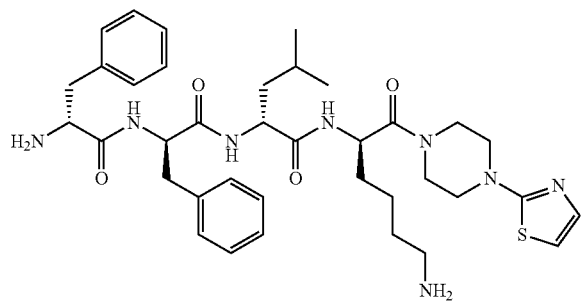 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCN(c2nccs2)CC1]

Compound (67): D-Phe-D-Phe-D-Leu-D-Lys-[N,N-dimethylpiperazine-1-sulfonamide amide]:

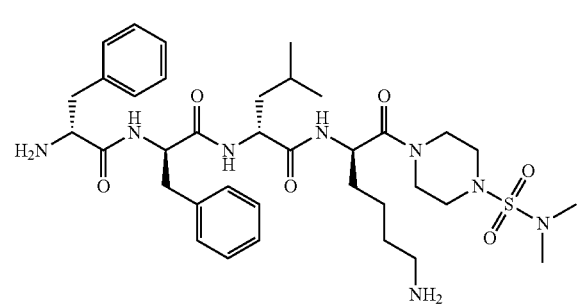 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCN(S(=O)(=O)N(C)C)CC1]

Compound (68): D-Phe-D-Phe-D-Leu-D-Lys-[1-(methylsulfonyl)piperazine amide]:

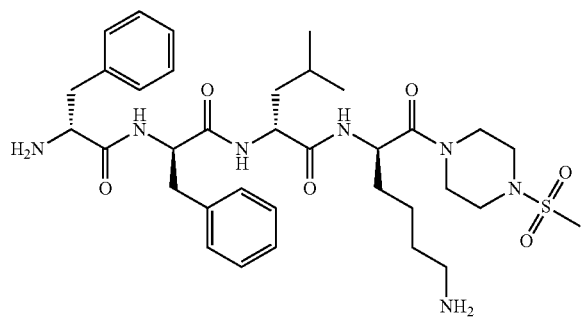 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCN(S(C)(=O)=O)CC1]

Compound (69): D-Phe-D-Phe-D-Leu-D-Lys-[1-(phenylsulfonyl)piperazine amide]:

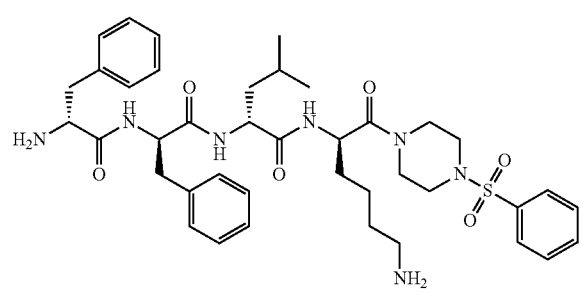 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCN(S(=O)(=O)c2ccccc2)CC1]

Compound (70): D-Phe-D-Phe-D-Leu-D-Lys-[phenyl(piperazin-1-yl)methanone amide]:

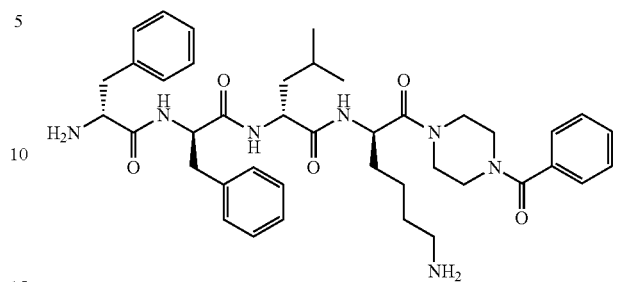

Compound (71): D-Phe-D-Phe-D-Leu-D-Lys-[thiolmorpholine-1,1-dioxide amide]:

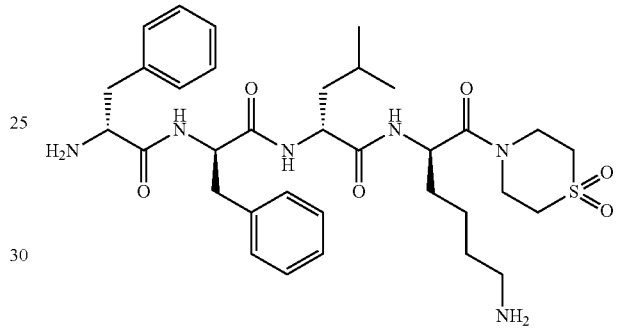

Compound (72): D-Phe-D-Phe-D-Leu-D-Lys[6-trifluoromethyl-3-aminomethyl pyridine amide]:

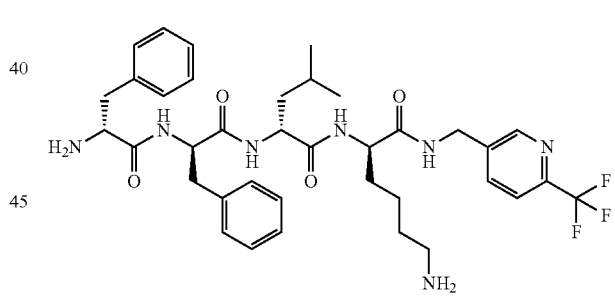

Compound (73): D-Phe-D-Phe-D-Leu-D-Lys-N-methyl-1-(tetrahydro-2H-pyran-4-yl)methanamine amide:

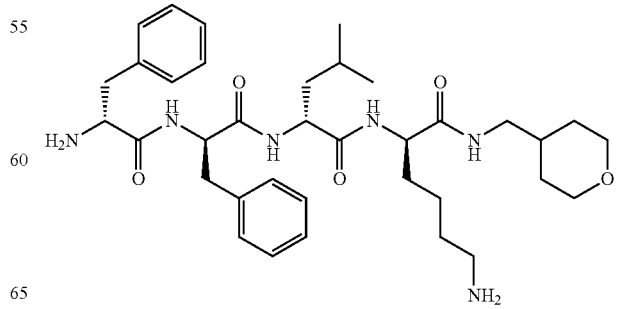

Compound (74): D-Phe-D-Phe-D-Leu-D-Lys-[5-(aminomethyl)-1H-benzo[d]imidazol-2(3H)-one amide]:
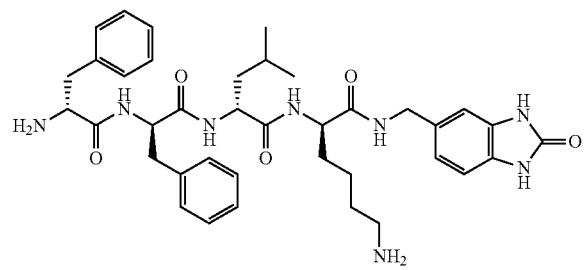 [SMILES: CC(C)C[C@@H](NC(=O)[C@@H](Cc1ccccc1)NC(=O)[C@H](N)Cc1ccccc1)C(=O)N[C@H](CCCCN)C(=O)NCc1ccc2[nH]c(=O)[nH]c2c1]
Compound (75): D-Phe-D-Phe-D-Leu-D-Lys-N-(thiazol-2-ylmethyl)amide:
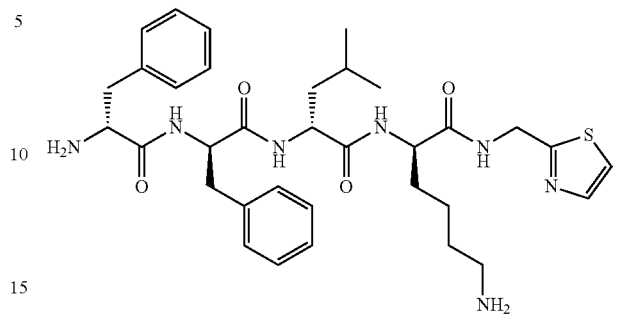
Compound (76):
D-Phe-D-Phe-D-Leu-D-Orn-εLys-OH
|
D-Phe-D-Phe-D-Leu-D-Orn
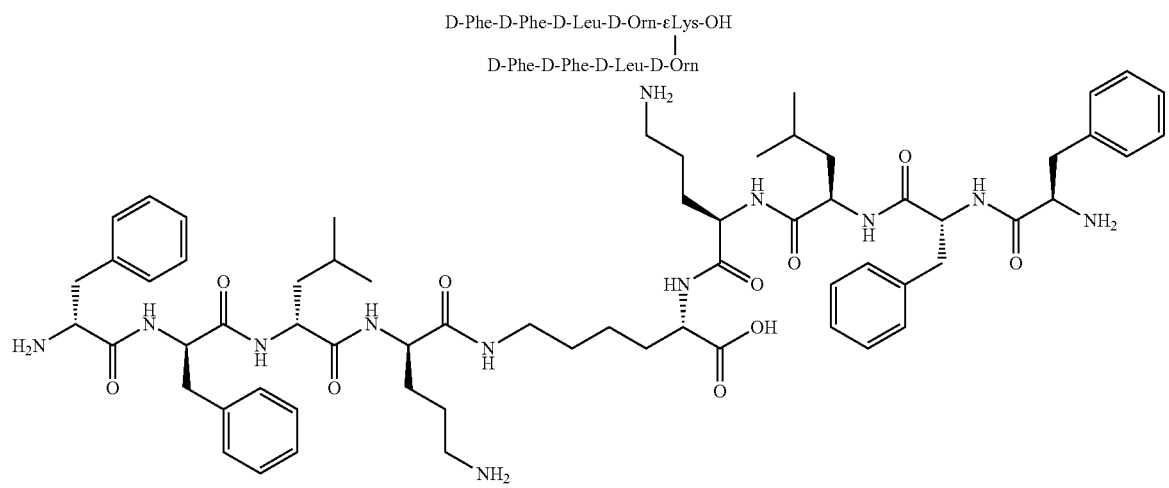
Compound (77):
D-Phe-D-Phe-D-Leu-D-Orn-εLys-OH
|
D-Leu-D-Orn
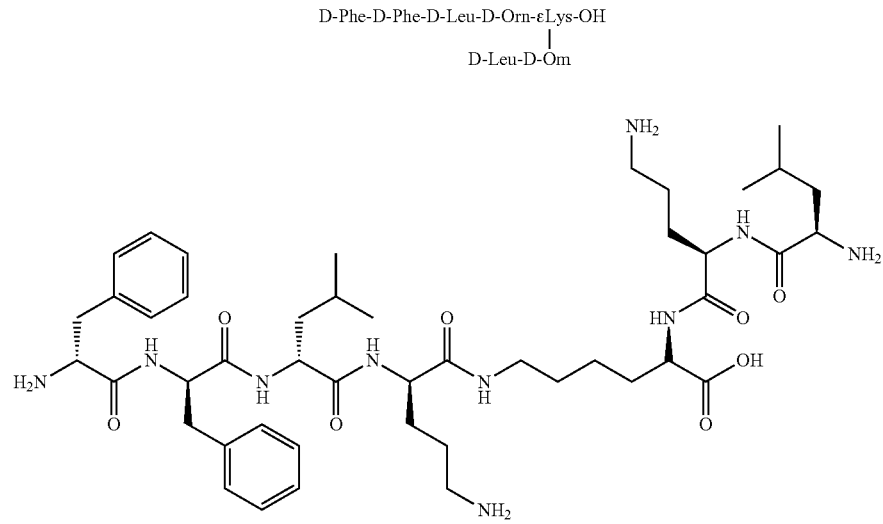

Compound (78):
D-Phe-D-Phe-D-Leu-D-Orn-εLys-OH
            |
     D-Phe-D-Leu-D-Orn
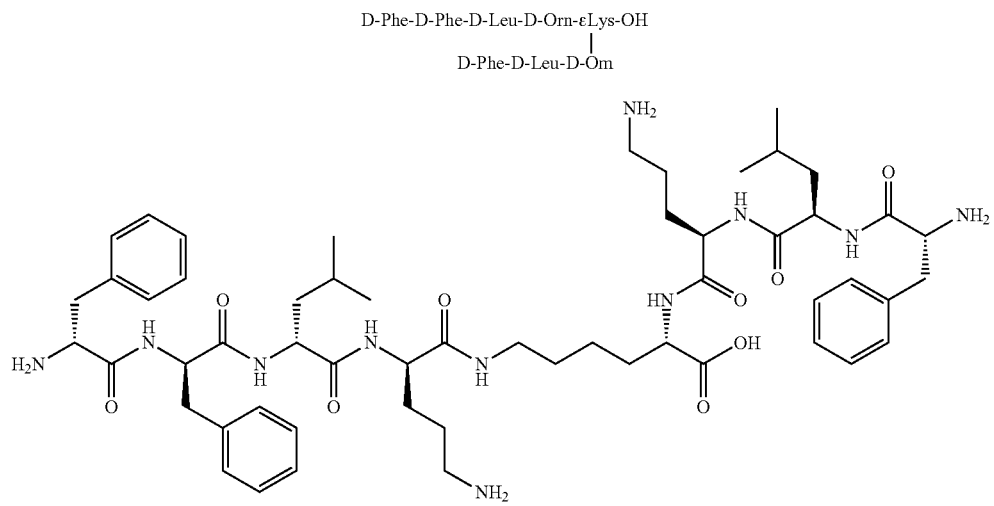
Compound (79):
D-Phe-D-Phe-D-Leu-D-Orn-εLys-OH
            |
          D-Orn
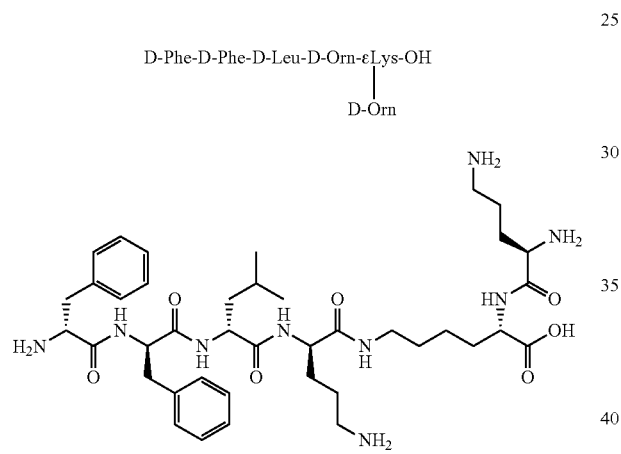
Compound (80):
D-Phe-D-Phe-D-Leu-D-Orn-εLys-NH$_2$
            |
     D-Phe-D-Phe-D-Leu-D-Orn
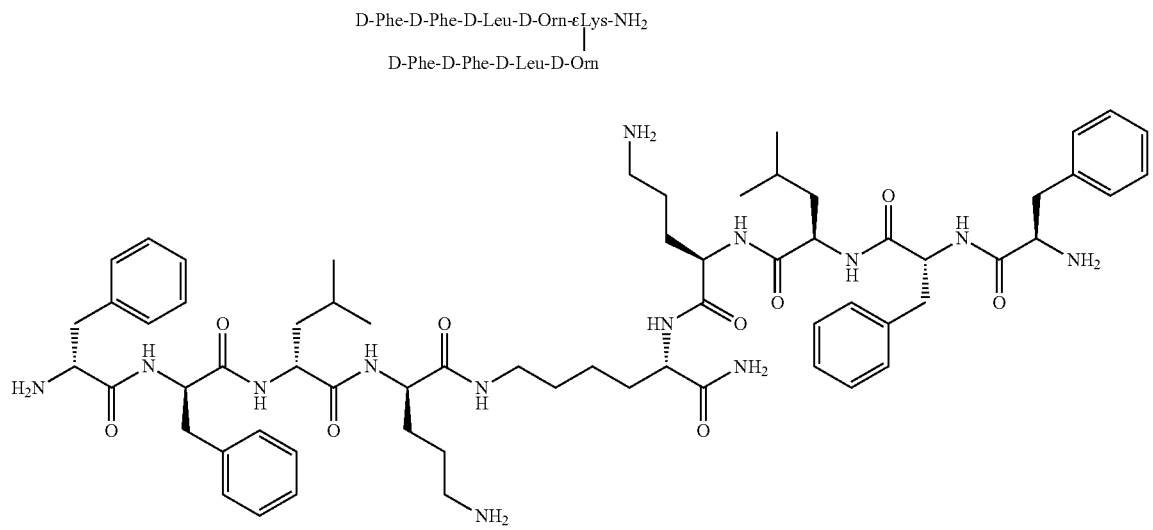 [SMILES: "eLys-NH2" ; "D-Phe-D-Phe-D-Leu-D-Orn" ; CC(C)C[C@@H](NC(=O)[C@@H](Cc1ccccc1)NC(=O)[C@H](N)Cc1ccccc1)C(=O)N[C@H](CCCN)C(=O)NCCCC[C@H](NC(=O)[C@@H](CCCN)NC(=O)[C@@H](CC(C)C)NC(=O)[C@@H](Cc1ccccc1)NC(=O)[C@H](N)Cc1ccccc1)C(N)=O]

Compound (81):
D-Phe-D-Phe-D-Leu-D-Orn-eLys-N(—CH₂CH₂—NH—CH₂CH₂—)₅
              |
            D-Orn
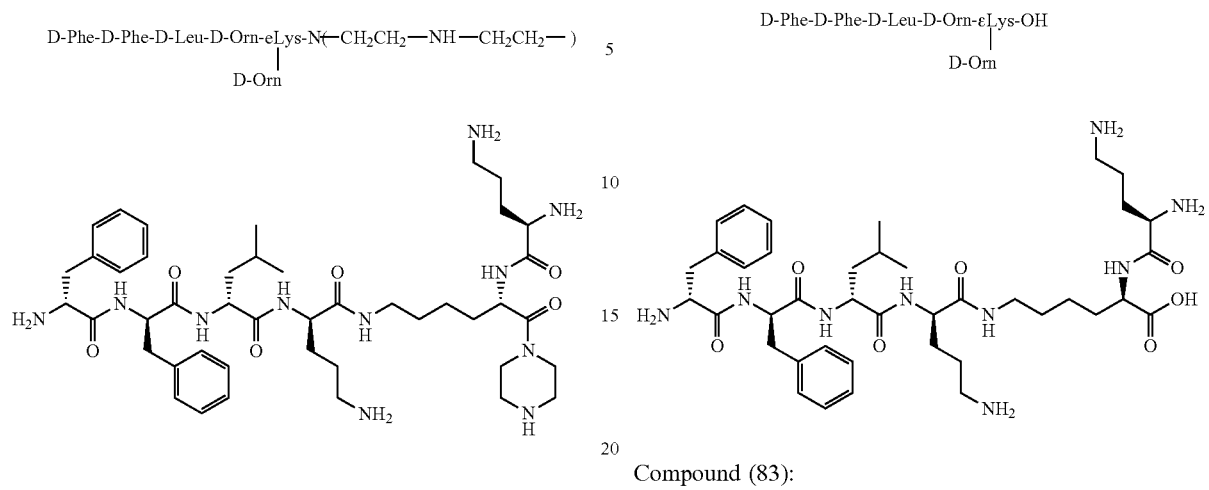
Compound (82):
D-Phe-D-Phe-D-Leu-D-Orn-εLys-OH
                         |
                       D-Orn
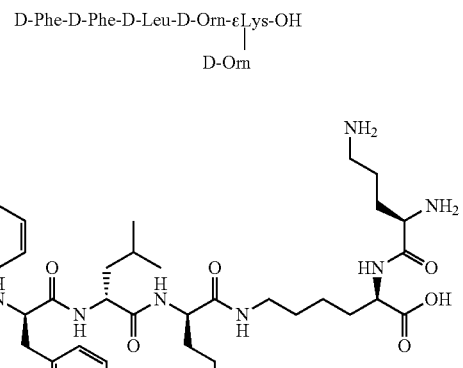
Compound (83):
D-Phe-D-Phe-D-Leu-D-Orn-εLys-OH
                         |
                    D-Leu-D-Orn
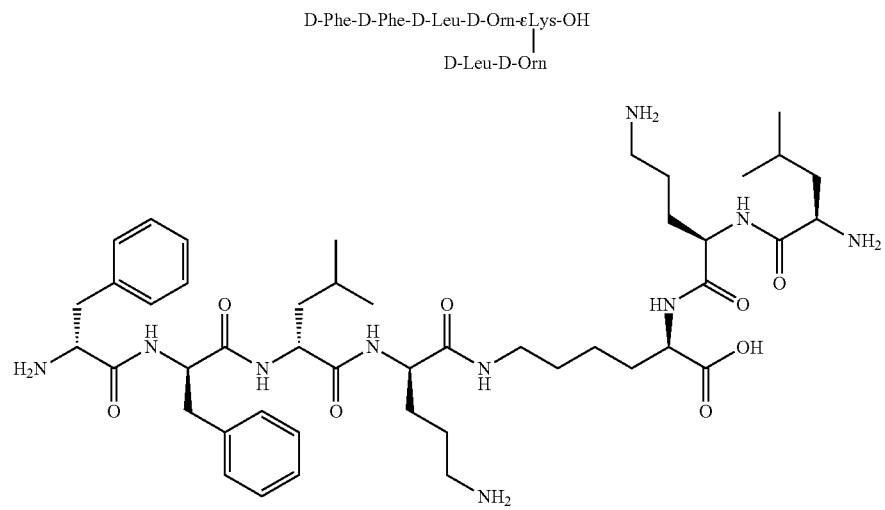 [SMILES: "eLys-OH" ; "D-Leu-D-Orn" ; CC(C)C[C@@H](N)C(=O)N[C@H](CCCN)C(=O)N[C@H](CCCCNC(=O)[C@@H](CCCN)NC(=O)[C@@H](CC(C)C)NC(=O)[C@@H](Cc1ccccc1)NC(=O)[C@H](N)Cc1ccccc1)C(=O)O]
Compound (84):
D-Phe-D-Phe-D-Leu-D-Orn-εLys-OH
                         |
                 D-Phe-D-Leu-D-Orn
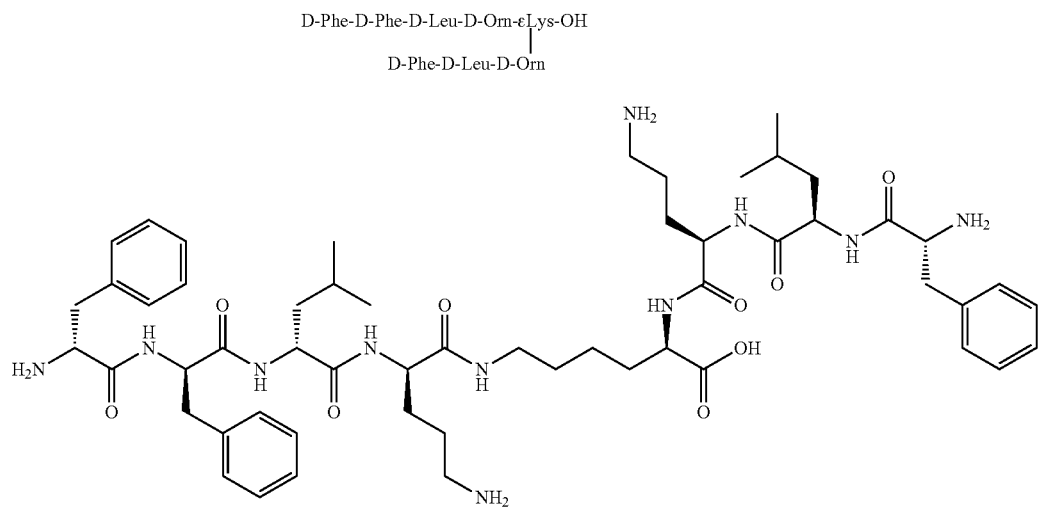 [SMILES: "eLys-OH" ; "D-Phe-D-Leu-D-Orn" ; CC(C)C[C@@H](NC(=O)[C@H](N)Cc1ccccc1)C(=O)N[C@H](CCCN)C(=O)N[C@H](CCCCNC(=O)[C@@H](CCCN)NC(=O)[C@@H](CC(C)C)NC(=O)[C@@H](Cc1ccccc1)NC(=O)[C@H](N)Cc1ccccc1)C(=O)O]

Compound (85):
D-Phe-D-Phe-D-Leu-D-Orn-εLys-OH
D-Phe-D-Phe-D-Leu-D-Orn
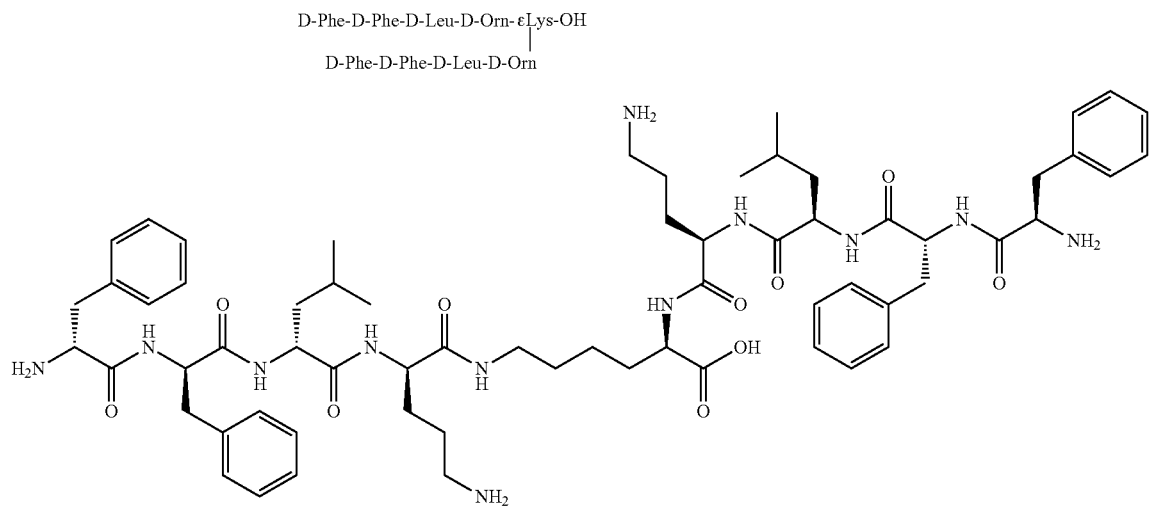 [SMILES: "eLys-OH" ; "D-Phe-D-Phe-D-Leu-D-Orn" ; CC(C)C[C@@H](NC(=O)[C@@H](Cc1ccccc1)NC(=O)[C@H](N)Cc1ccccc1)C(=O)N[C@H](CCCN)C(=O)NCCCC[C@@H](NC(=O)[C@@H](CCCN)NC(=O)[C@@H](CC(C)C)NC(=O)[C@@H](Cc1ccccc1)NC(=O)[C@H](N)Cc1ccccc1)C(=O)O]
Compound (86): 1N,4N-bis-[D-Phe-D-Phe-D-Leu-(iPr)D-Orn]-4-amino-4-carboxylic-piperidine
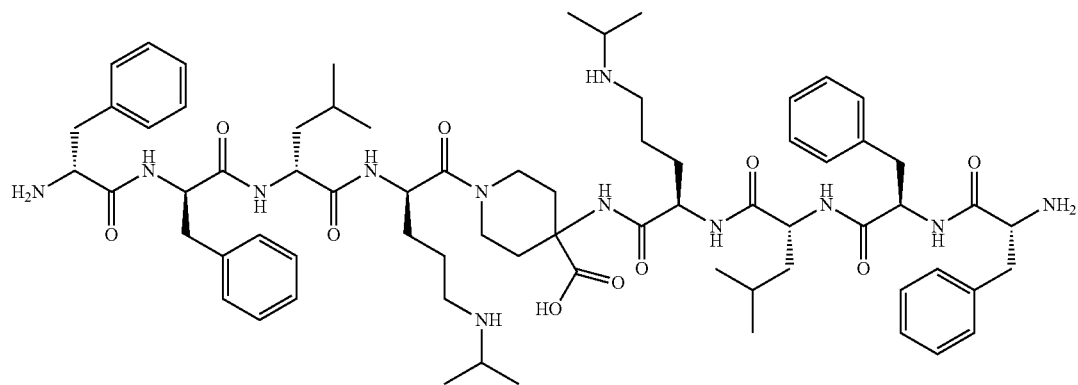 [SMILES: CC(C)C[C@@H](NC(=O)[C@@H](Cc1ccccc1)NC(=O)[C@H](N)Cc1ccccc1)C(=O)N[C@H](CCCNC(C)C)C(=O)NC1(C(=O)O)CCN(C(=O)[C@@H](CCCNC(C)C)NC(=O)[C@@H](CC(C)C)NC(=O)[C@@H](Cc2ccccc2)NC(=O)[C@H](N)Cc2ccccc2)CC1]
Compound (87): 1N,4N-bis-[D-Phe-D-Phe-D-Leu-D-Dap(amidino)]-4-amino-4-carboxylic piperidine
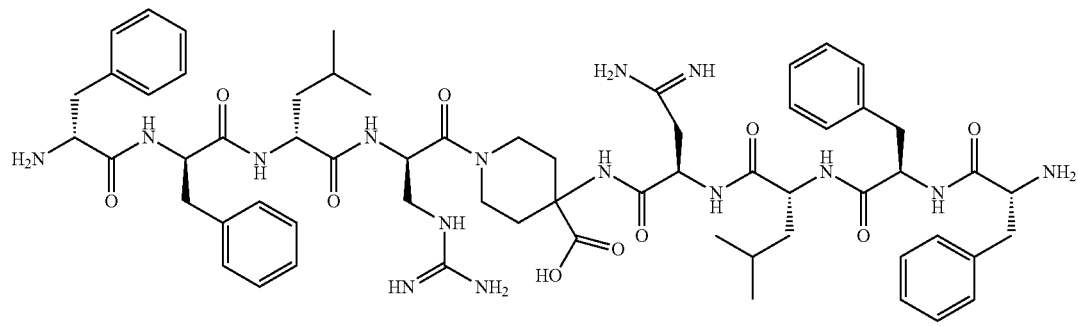 [SMILES: CC(C)C[C@@H](NC(=O)[C@@H](Cc1ccccc1)NC(=O)[C@H](N)Cc1ccccc1)C(=O)N[C@H](CC(=N)N)C(=O)NC1(C(=O)O)CCN(C(=O)[C@@H](CNC(=N)N)NC(=O)[C@@H](CC(C)C)NC(=O)[C@@H](Cc2ccccc2)NC(=O)[C@H](N)Cc2ccccc2)CC1]

Compound (88): 1N,4N-bis-(D-Phe-D-Phe-D-Leu-D-Nar)-4-amino-4-carboxylic piperidine
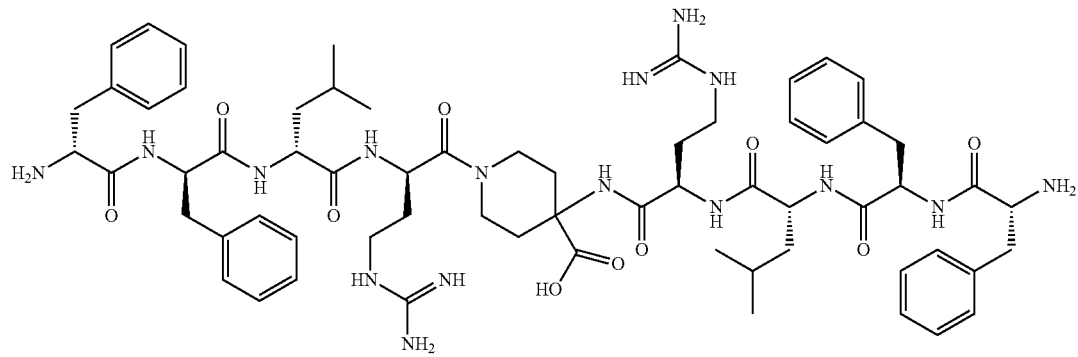 [SMILES: CC(C)C[C@@H](NC(=O)[C@@H](Cc1ccccc1)NC(=O)[C@H](N)Cc1ccccc1)C(=O)N[C@H](CCNC(=N)N)C(=O)NC1(C(=O)O)CCN(C(=O)[C@@H](CCNC(=N)N)NC(=O)[C@@H](CC(C)C)NC(=O)[C@@H](Cc2ccccc2)NC(=O)[C@H](N)Cc2ccccc2)CC1]
Compound (89):
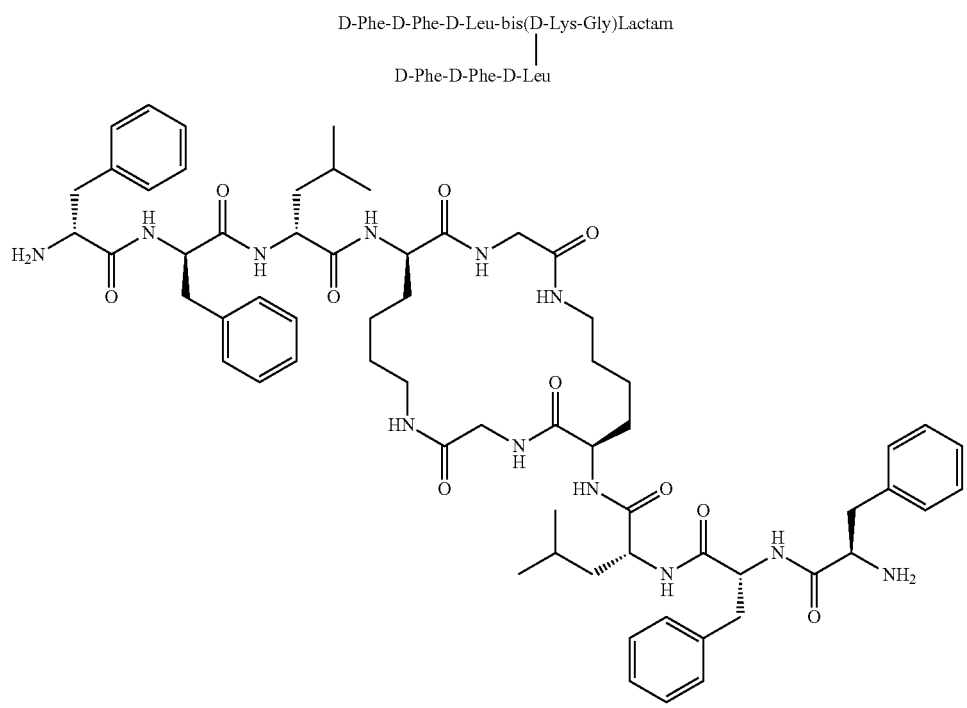 [SMILES: CC(C)C[C@@H](NC(=O)[C@@H](Cc1ccccc1)NC(=O)[C@H](N)Cc1ccccc1)C(=O)N[C@@H]1CCCCNC(=O)CNC(=O)[C@H](NC(=O)[C@@H](CC(C)C)NC(=O)[C@@H](Cc2ccccc2)NC(=O)[C@H](N)Cc2ccccc2)CCCCNC(=O)CNC1=O]
Compound (90) D-Phe-D-Phe-D-Leu-D-Orn-[R/S-2-carboxymorpholine]-OH:
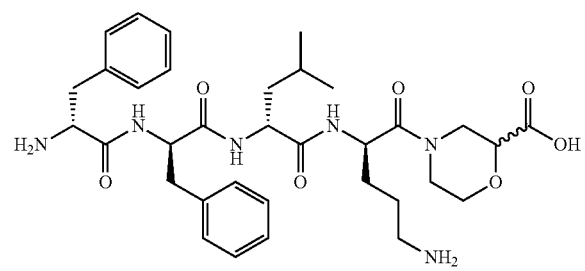 [SMILES: CC(C)C[C@@H](NC(=O)[C@@H](Cc1ccccc1)NC(=O)[C@H](N)Cc1ccccc1)C(=O)N[C@H](CCCN)C(=O)N1CCSC(C(=O)O)C1]
Compound (91) D-Phe-D-Phe-D-Leu-D-Orn-[R/S-2-carboxythiomorpholine]-OH:
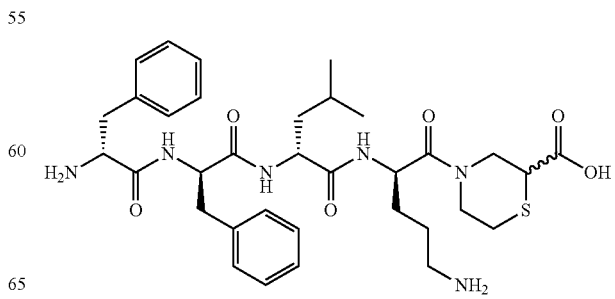

Compound (92) D-Phe-D-Phe-D-Leu-D-Orn-N(homomorpholine):

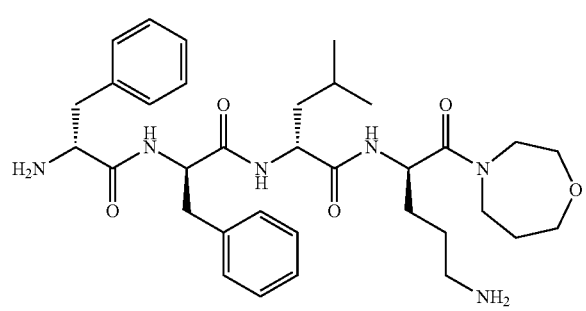

Compound (93) D-Phe-D-Phe-D-Leu-D-Orn-N(homothiomorpholine):

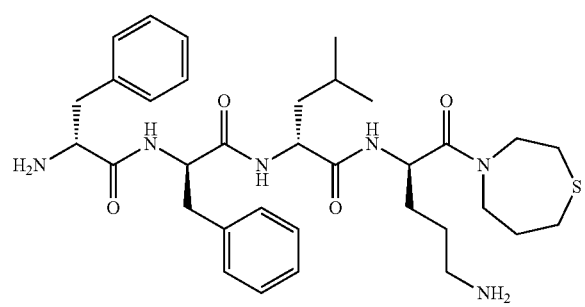 [SMILES: CC(C)C[C@@H](NC(=O)[C@@H](Cc1ccccc1)NC(=O)[C@H](N)Cc1ccccc1)C(=O)N[C@H](CCCN)C(=O)N1CCCOCC1]

Compound (94) D-Phe-D-Phe-D-Leu-D-Dap(amidino)-[homomorpholine amide]:

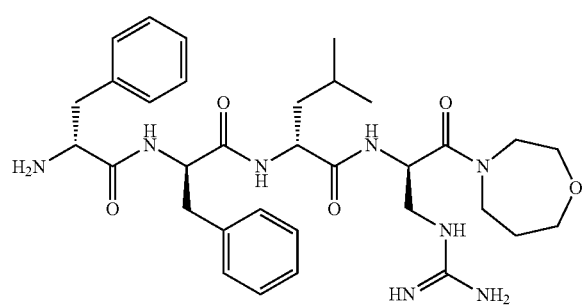 [SMILES: CC(C)C[C@@H](NC(=O)[C@@H](Cc1ccccc1)NC(=O)[C@H](N)Cc1ccccc1)C(=O)N[C@H](CNC(=N)N)C(=O)N1CCCOCC1]

Compound (95) D-Phe-D-Phe-D-Leu-D-Dap(amidino)-[homothiomorpholine amide]:

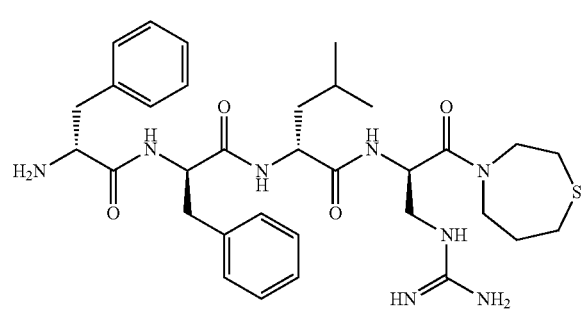 [SMILES: CC(C)C[C@@H](NC(=O)[C@@H](Cc1ccccc1)NC(=O)[C@H](N)Cc1ccccc1)C(=O)N[C@H](CNC(=N)N)C(=O)N1CCCSCC1]

Compound (96) D-Phe-D-Phe-D-Me-D-Dap(amidino)-[homomorpholine amide]:

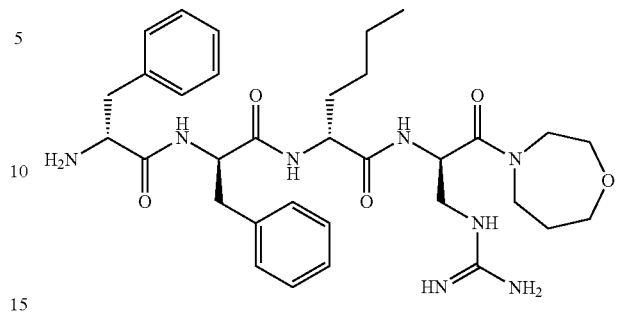

Compound (97) D-Phe-D-Phe-D-Nle-D-Dap(amidino)-[homothiomorpholine amide]:

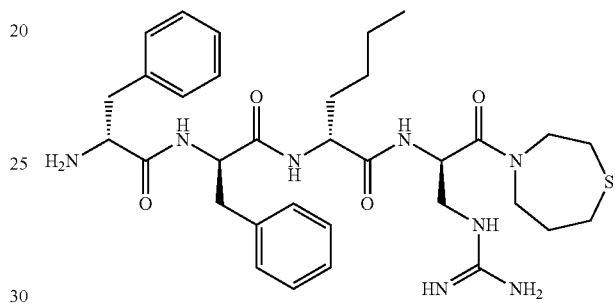

Compound (98) D-Phe-D-Phe-D-Leu-D-Arg-[homomorpholine amide]:

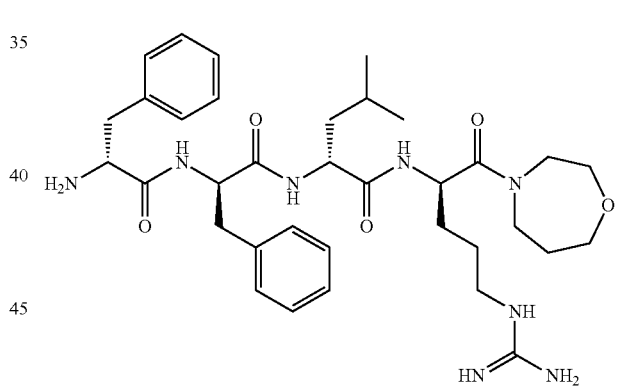

Compound (99) D-Phe-D-Phe-D-Leu-D-Arg-[homothiopiperazine amide]:

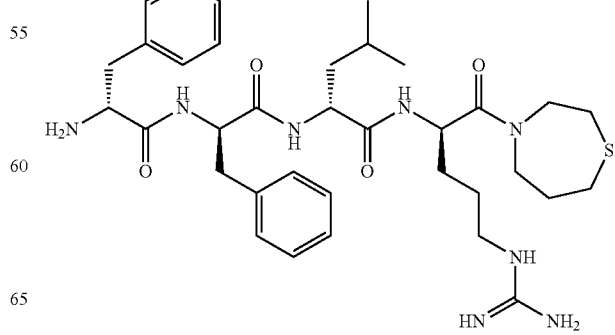

Compound (100) D-Phe-D-Phe-D-Leu-D-Orn(Me)-[homomorpholine amide]:

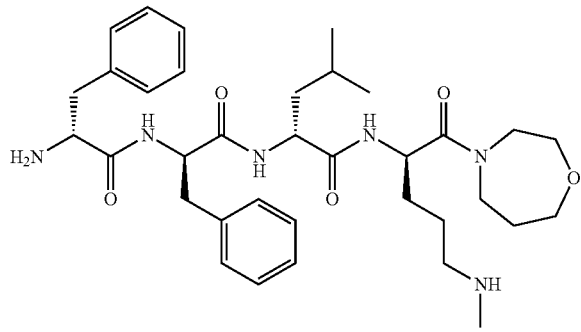 [SMILES: CNCCC[C@@H](NC(=O)[C@@H](CC(C)C)NC(=O)[C@@H](Cc1ccccc1)NC(=O)[C@H](N)Cc1ccccc1)C(=O)N1CCCOCC1]

Compound (101) D-Phe-D-Phe-D-Leu-D-Orn(Me)-[homothiomorpholine amide]:

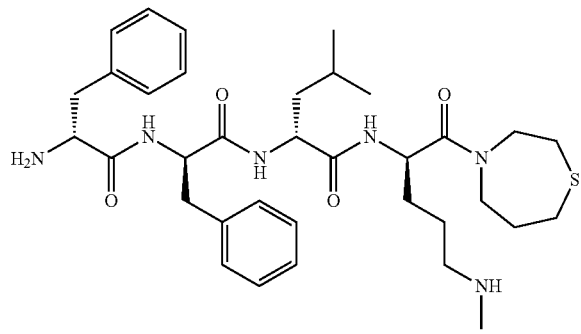

Compound (102) D-Phe-D-Phe-D-Leu-D-Orn(iPr)-[homomorpholine amide]:

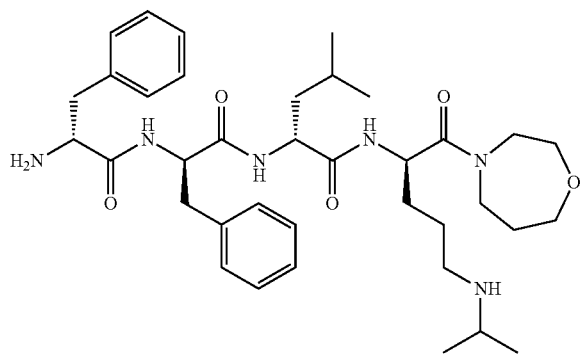 [SMILES: CC(C)C[C@@H](NC(=O)[C@@H](Cc1ccccc1)NC(=O)[C@H](N)Cc1ccccc1)C(=O)N[C@H](CCCNC(C)C)C(=O)N1CCCOCC1]

Compound (103) D-Phe-D-Phe-D-Leu-D-Orn(iPr)-[homothiomorpholine amide]:

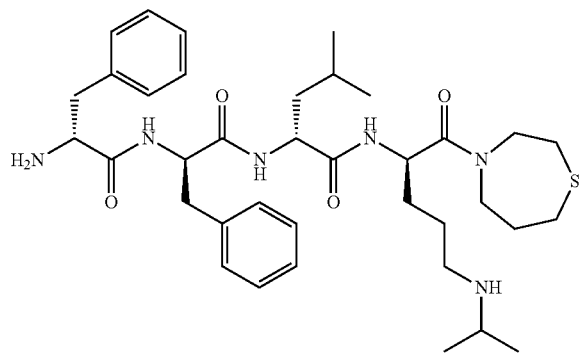

Compound (104): β-tert-Bu-D-Ala-D-Phe-D-Leu-D-Lys-[ω(4-aminopiperidine-4-carboxylic acid)]-OH:

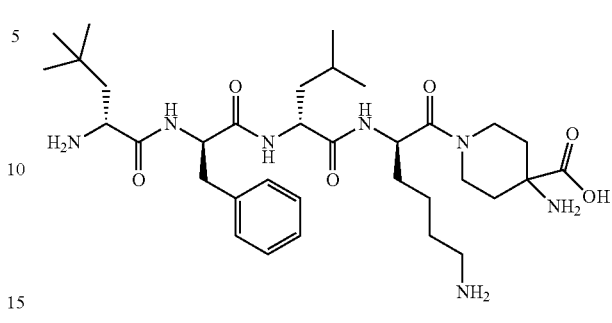

Compound (105): D-tert-Leu-D-Phe-D-Leu-D-Lys-[ω(4-aminopiperidine-4-carboxylic acid)]-OH:

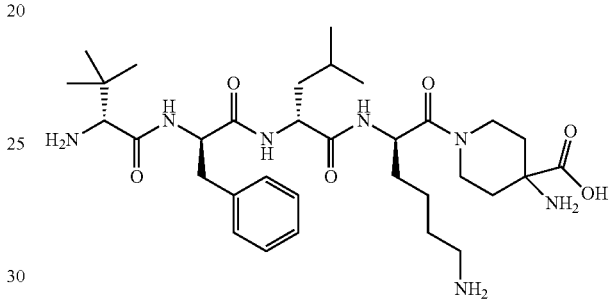

For purposes of the compounds falling under group (dd), as disclosed in U.S. Pat. No. 7,713,937, the term "synthetic peptide amide" means a compound conforming to formula I, or a stereoisomer, mixture of stereoisomers, prodrug, pharmaceutically acceptable salt, hydrate, solvate, acid salt hydrate, N-oxide or isomorphic crystalline form thereof. The designations $Xaa_1$, $Xaa_2$, $Xaa_3$, and $Xaa_4$ represent D-amino acids in the synthetic peptide amides of the invention. Stereoisomers of the synthetic peptide amides conforming to formula I are limited to those compounds having amino acids in the D-configuration where so specified in Formula I. Stereoisomers of the synthetic peptide amides include compounds having either a D- or L-configuration at chiral centers other than the alpha carbons of the four amino acids at $Xaa_1$, $Xaa_2$, $Xaa_3$, and $Xaa_4$. The term 'mixtures of stereoisomers' refer to mixtures of such stereoisomers. As used herein 'racemates' refers to mixtures of stereoisomers having equal proportions of compounds with D- and L-configuration at one or more of the chiral centers other than the alpha carbons of $Xaa_1$, $Xaa_2$, $Xaa_3$, and $Xaa_4$ without varying the chirality of the alpha carbons of $Xaa_1$, $Xaa_2$, $Xaa_3$, and $Xaa_4$.

The nomenclature used to define peptides of compounds (dd) is specified by Schroder & Lubke, *The Peptides*, Academic Press, 1965, wherein, in accordance with conventional representation, the N-terminus appears to the left and the C-terminus to the right. Where an amino acid residue has isomeric forms, both the L-isomer form and the D-isomer form of the amino acid are intended to be covered unless otherwise indicated. Amino acids are commonly identified herein by the standard three-letter code. The D-isomer of an amino acid is specified by the prefix "D-" as in "D-Phe" which represents D-phenylalanine, the D-isomer of phenylalanine. Similarly, the L-isomer is specified by the prefix "L-" as in "L-Phe." Peptides are represented herein according to the usual convention as amino acid sequences from left to right: N-terminus to C-terminus, unless otherwise specified.

As used herein, D-Arg represents D-arginine, D-Har represents D-homoarginine, which has a side chain one methylene group longer than D-Arg, and D-Nar represents D-norarginine, which has a side chain one methylene group shorter than D-Arg. Similarly, D-Leu means D-leucine, D-Nle means D-norleucine, and D-Hle represents D-homoleucine. D-Ala means D-alanine, D-Tyr means D-tyrosine, D-Trp means D-tryptophan, and D-Tic means D-1,2,3,4-tetrahydroisoquinoline-3-carboxylic acid. D-Val means D-valine and D-Met means D-methionine. D-Pro means D-proline, Pro-amide means the D- or L-form of proline amide. D-Pro amide represents D-proline with an amide formed at its carboxy moiety wherein the amide nitrogen may be alkyl substituted, as in —$NR_aR_b$, wherein $R_a$ and $R_b$ are each independently a $C_1$-$C_6$ alkyl group, or one of $R_a$ and $R_b$ is —H. Gly means glycine, D-Ile means D-isoleucine, D-Ser means D-serine, and D-Thr means D-threonine. (E)D-Ala means the D-isomer of alanine which is substituted by the substituent (E) on the β-carbon. Examples of such substituent (E) groups include tert-butyl, cyclopropyl, cyclobutyl, cyclopentyl, cyclohexyl, furyl, pyridyl, thienyl, thiazolyl and benzothienyl. Thus, cyclopentyl-D-Ala means the D-isomer of alanine which is substituted by cyclopentyl on the β-carbon. Similarly, D-Ala(2-thienyl) and (2-thienyl)D-Ala are interchangeable and both mean the D-isomer of alanine substituted at the β-carbon with thienyl that is attached at the 2-ring position.

As used for the compounds of (dd), D-Nal means the D-isomer of alanine substituted by naphthyl on the β-carbon. D-2Nal means naphthyl substituted D-alanine wherein the attachment to naphthalene is at the 2-position on the ring structure and D-1Nal means naphthyl-substituted D-alanine wherein the attachment to naphthalene is at the 1-position on the ring structure. By (A)(A')D-Phe is meant D-phenylalanine substituted on the phenyl ring with one or two substituents independently chosen from halo, nitro, methyl, halomethyl (such as, for example, trifluoromethyl), perhalomethyl, cyano and carboxamide. By D-(4-F)Phe is meant D-phenylalanine which is fluoro-substituted in the 4-position of the phenyl ring. By D-(2-F)Phe is meant D-phenylalanine which is fluoro-substituted in the 2-position of the phenyl ring. By D-(4-Cl)Phe is meant D-phenylalanine which is chloro substituted in the 4-phenyl ring position. By (α-Me)D-Phe is meant D-phenylalanine which is methyl substituted at the alpha carbon. By (α-Me)D-Leu is meant D-leucine which is methyl substituted at the alpha carbon. The designations $(B)_2$D-Arg, $(B)_2$D-Nar, and $(B)_2$D-Har represent D-arginine, D-norarginine and D-homoarginine, respectively, each having two substituent (B) groups on the side chain. D-Lys means D-lysine and D-Hlys means D-homolysine. ζ-(B)D-Hlys, ε-(B)D-Lys, and ε-$(B)_2$-D-Lys represent D-homolysine and D-lysine each having the side chain amino group substituted with one or two substituent (B) groups, as indicated. D-Orn means D-ornithine and δ-(B)α-(B')D-Orn means D-ornithine substituted with (B') at the alpha carbon and substituted with (B) at the side chain δ-amino group. D-Dap means D-2,3-diaminopropionic acid. D-Dbu represents the D-isomer of alpha, gamma-diamino butyric acid and $(B)_2$D-Dbu represents alpha, gamma-diamino butyric acid which is substituted with two substituent (B) groups at the gamma amino group. Unless otherwise stated, each of the (B) groups of such doubly substituted residues are independently chosen from H— and $C_1$-$C_4$-alkyl. As used herein, D-Amf means D-($NH_2CH_2$-)Phe, i.e., the D-isomer of phenylalanine substituted with aminomethyl on its phenyl ring and D-4Amf represents the particular D-Amf in which the aminomethyl is attached at the 4-position of the ring. D-Gmf means D-Amf(amidino) which represents D-Phe wherein the phenyl ring is substituted with —$CH_2NHC(NH)NH_2$. Amd represents amidino, —$C(NH)NH_2$, and the designations (Amd)D-Amf and D-Amf(Amd) are also interchangeably used for D-Gmf. The designations Ily and Ior are respectively used to mean isopropyl Lys and isopropyl Orn, wherein the side chain amino group is alkylated with an isopropyl group. Alkyl means an alkane radical which can be a straight, branched, and cyclic alkyl group such as, but not limited to, methyl, ethyl, propyl, isopropyl, cyclopropyl, butyl, t-butyl, sec-butyl, pentyl, cyclopentyl, hexyl, cyclohexyl, cyclohexylethyl. $C_1$ to $C_8$ alkyl refers to alkyl groups having between one and eight carbon atoms. Similarly, $C_1$-$C_6$ alkyl refers to alkyl groups having between one and six carbon atoms. Likewise, $C_1$-$C_4$ alkyl refers to alkyl groups having between one and four carbon atoms. By lower alkyl is meant $C_1$-$C_6$ alkyl. Me, Et, Pr, Ipr, Bu, and Pn are interchangeably used to represent the common alkyl groups: methyl, ethyl, propyl, isopropyl, butyl, and pentyl, respectively. Although the linkage for an alkyl group is typically at one end of an alkyl chain, the linkage may be elsewhere in the chain, e.g. 3-pentyl which may also be referred to as ethylpropyl, or 1-ethylprop-1-yl. Alkyl-substituted, such as $C_1$ to $C_6$ alkyl-substituted amidino, indicates that the relevant moiety is substituted with one or more alkyl groups.

Where a specified moiety of the compounds of group (dd) is null, the moiety is absent and if such moiety is indicated to be attached to two other moieties, such two other moieties are connected by one covalent bond. Where a connecting moiety is shown herein as attached to a ring at any position on the ring, and attached to two other moieties, such as $R_1$ and $R_2$, in the case where the connecting moiety is specified to be null, then the $R_1$ and $R_2$ moieties can each be independently attached to any position on the ring. The terms "heterocycle", "heterocyclic ring" and "heterocyclyl" are used interchangeably herein and refer to a ring or ring moiety having at least one non-carbon ring atom, also called a heteroatom, which can be a nitrogen atom, a sulfur atom, or an oxygen atom. Where a ring is specified as having a certain number of members, the number defines the number of ring atoms without reference to any substituents or hydrogen atoms bonded to the ring atoms. Heterocycles, heterocyclic rings and heterocyclyl moieties can include multiple heteroatoms independently selected from nitrogen, sulfur, or oxygen atom in the ring. Rings can be substituted at any available position. For example, but without limitation, 6- and 7-membered rings are often substituted in the 4-ring position and 5-membered rings are commonly substituted in the 3-position, wherein the ring is attached to the peptide amide chain at the 1-ring position. The term "saturated" means an absence of double or triple bonds and the use of the term in connection with rings describes rings having no double or triple bonds within the ring, but does not preclude double or triple bonds from being present in substituents attached to the ring. The term "non-aromatic" in the context of a particular ring refers to an absence of aromaticity in that ring, but does not preclude the presence of double bonds within the ring, including double bonds which are part of an aromatic ring fused to the ring in question. Nor is a ring atom of a saturated heterocyclic ring moiety precluded from being double-bonded to a non-ring atom, such as for instance a ring sulfur atom being double-bonded to an oxygen atom substituent. As used herein, heterocycles, heterocyclic rings and heterocyclyl moieties also include saturated, partially unsaturated and heteroaromatic rings and fused bicyclic ring structures unless otherwise specified. A heterocycle, heterocyclic ring or heterocyclyl moiety can be fused to a second ring, which can be a saturated, partially unsaturated, or aromatic ring, which ring can be a heterocycle or a carbocycle. Where indicated, two substituents can be optionally taken together to form an additional ring. Rings may be substituted at any available position. A heterocycle, heterocyclic ring and heterocyclyl moiety can, where indicted, be optionally substituted at one or more ring positions with one or more independently selected substituents, such as for instance, $C_1$-$C_6$ alkyl, $C_3$-$C_8$ cycloalkyl, $C_1$-$C_6$ alkoxy, halo $C_1$-$C_6$ alkyl, optionally substituted phenyl, aryl, heterocyclyl, oxo, —OH, —Cl, —F, —NH$_2$, —NO$_2$, —CN, —COOH and amidino. Suitable optional substituents of the phenyl substituent include for instance, but without limitation, one or more groups selected from $C_1$-$C_3$ alkyl, $C_1$-$C_3$alkoxy, halo $C_1$-$C_3$ alkyl, oxo, —OH, —Cl, —F, —NH$_2$, —NO$_2$, —CN, —COOH and amidino. D-Phe and substituted D-Phe are examples of a suitable amino acid for residue $Xaa_1$ in Formula I. The phenyl ring can be substituted at any of the 2-, 3- and/or 4-positions. Particular examples of permitted substitutions include, for instance, chlorine or fluorine at the 2- or 4-positions. Also the alpha-carbon atom may be methylated. Other equivalent residues which represent conservative changes to D-Phe can also be used. These include D-Ala (cyclopentyl), D-Ala(thienyl), D-Tyr and D-Tic. The residue at the second position, $Xaa_2$ can also be D-Phe or substituted D-Phe with such substitutions including a substituent on the 4-position carbon of the phenyl ring, or on both the 3- and 4-positions. Alternatively, $Xaa_2$ can be D-Trp, D-Tyr or D-alanine substituted by naphthyl. The third position residue, $Xaa_3$ can be any non-polar amino acid residue, such as for instance, D-Nle, D-Leu, (α-Me)D-Leu, D-Hle, D-Met or D-Val. However, D-Ala(cyclopropyl, cyclobutyl, cyclopentyl or cyclohexyl) or D-Phe can also be used as $Xaa_3$. The fourth position residue $Xaa_4$ can be any positively charged amino acid residue, such as for instance, D-Arg and D-Har, which can be optionally substituted with lower alkyl groups, such as one or two ethyl groups. Alternatively, D-Nar and any other equivalent residues can be used, such as, for instance, D-Lys or D-Orn (either of which can be ω-amino group alkylated, for example by methyl or isopropyl groups, or methylated at the α-carbon group). Moreover, D-Dbu, D-4-Amf (which can be optionally substituted with amidino), and D-Hlys are also suitable amino acids at this position. The chemical designation "tetrapeptide-[ω(4-amino-piperidine-4-carboxylic acid)]" is used to indicate the aminoacyl moiety of the synthetic peptide amides of the invention derived from 4-aminopiperidine-4-carboxylic acid, wherein the nitrogen atom of the piperidine ring is bound to the C-terminal carbonyl-carbon of the tetrapeptide fragment, unless otherwise indicated.

Compounds of the group (dd) as disclosed in U.S. Pat. No. 7,713,937 contain one or more chiral centers, each of which has two possible three-dimensional spatial arrangements (configurations) of the four substituents around the central carbon atom. These are known as "stereoisomers", and more specifically as "enantiomers" (all chiral centers inverted) or "diastereoisomers" (two or more chiral centers, at least one chiral center remaining the same). In a specific embodiment of the invention, the amino acids which make up the tetrapeptide backbone, $Xaa_1Xaa_2Xaa_3Xaa_4$ are specified to be D-amino acids i.e., the opposite configuration to those generally found in mammals. Reference to stereoisomers of the synthetic peptide amides concerns chiral centers other than the alpha carbons of the D-amino acids, which make up $Xaa_1$-$Xaa_4$. Thus, stereoisomers of synthetic peptide amides wherein each of $Xaa_1$-$Xaa_4$ are specified to be D-amino acids, do not include L-amino acids or racemic mixtures of the amino acids at these positions. Similarly, reference to racemates herein concerns a center other than the alpha carbons of the D-amino acids which make up $Xaa_1$-$Xaa_4$. Chiral centers in the synthetic peptide amides of the invention for which a stereoisomer may take either the R or S configuration include chiral centers in the moiety attached to the carboxy-terminus of $Xaa_4$, and also chiral centers in any amino acid side chain substituents of $Xaa_1$-$Xaa_4$. The synthetic peptide amides can be used or prepared in alternate forms. For example, many amino-containing compounds can be used or prepared as an acid salt. Often such salts improve isolation and handling properties of the compound. For example, depending on the reagents, reaction conditions and the like, compounds such as the synthetic peptide amides described herein can be used or prepared, for example, as the hydrochloride or tosylate salts. The use of isomorphic crystalline forms, all chiral and racemic forms, N-oxide, hydrates, solvates, and acid salt hydrates, are also contemplated to be within the scope of the present invention. Certain acidic or basic synthetic peptide amides of the present invention may exist as zwitterions. All forms of these synthetic peptide amide compounds, including free acid, free base and zwitterions, are contemplated for use in the methods of the present invention. It is well known in the art that compounds containing both amino and carboxyl groups often exist in equilibrium with their zwitterionic forms. Thus, for any compound described herein that contains, for example, both amino and carboxyl groups, it will also be understood to include the corresponding zwitterion.

In a preferred embodiment, the kappa agonist is a peripherally restricted kappa agonist, including one or more of ICI-204,448, Asimadoline, FE 200665, Fedotozine, any compound disclosed in U.S. Pat. No. 7,713,937 (including but not limited to Cara Therapeutics compound CR854), any peptide disclosed in U.S. Pat. No. 5,965,701, combinations thereof, or pharmaceutical salts thereof. The theoretical benefits of a peripherally restricted agent (be it a kappa agonist, NKB/NK3R antagonist, or a substance P/NK1R antagonist) is that it would have only limited access to the higher centers of the brain—areas controlling cognition, mood, affect, movement, and integrative sensory function (which are within the blood-brain barrier), but still have full access to parts of the brain that are outside of the blood brain barrier, including those areas of the hypothalamus that generate the VMS. This novel approach would avoid the "side effects" of centrally active agents (that cross the blood brain barrier), such as dysphoria and euphoria, mental confusion, drowsiness, diminished attentiveness, depression, etc. Since efficacious kappa agonists produce compliance-limiting dysphoric responses when absorbed into brain; agents that do not efficiently penetrate the blood-brain barrier will produce the desired effect (e.g., reduction of hot-flash symptoms) without adverse cognitive or mood disturbance.

In another embodiment, the compound comprises a neurokinin type 3 receptor antagonist (NK3R). Neurokinin B (NKB) acts directly on KNDy neurons through NK3R to amplify their activity, and likewise, NK3R antagonists block KNDy neuronal activity (Navarro et al., Am J Physiol Endocrinol Metab. 2011 January; 300(1):E202-10.; Navarro et al., Endocrinology. 2011 November; 152(11):4265-75; Ruiz-Pino F et al., 2012 October; 153(10):4818-29).

The term "antagonist" refers to a compound that can bind to a neurokinin B receptor (NK3R) but has little or no functional activity of its own at the receptor—thus disrupting, blocking or otherwise interfering with the action of the naturally occurring, endogenous ligand (i.e., NKB). An antagonist may be a ligand that directly binds to the receptor. Alternatively, an antagonist may combine with a receptor indirectly by, for example, (a) forming a complex with another molecule that directly binds to the receptor, or (b) otherwise results in the modification of another compound so that the other compound directly binds to the NK3R. In other embodiments, the term "antagonist" may include "inverse agonists", which bind to NK3R and inhibit constitutive activity.

Any suitable NK3R antagonist can be used, including but not limited to (or stereoisomers, mixture of stereoisomers, prodrugs, pharmaceutically acceptable salts, hydrates, solvates, acid salt hydrates, N-oxides and isomorphic crystalline forms thereof):

(i) SB222200 (Available from, for example, Tocris Bioscience)

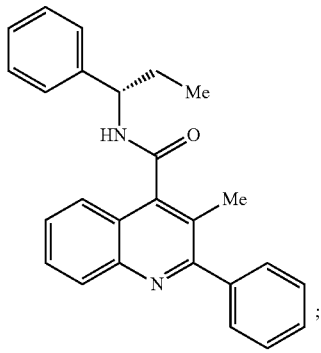 [SMILES: CC[C@H](NC(=O)c1c(C)c(-c2ccccc2)nc2ccccc12)c1ccccc1]

(ii) SR 142801 (Osanetant) (Available from, for example, Axon Medchem, Germany)

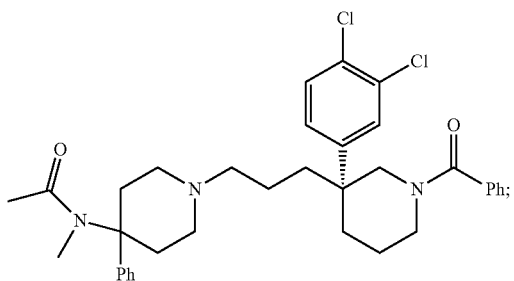 [SMILES: CC(=O)N(C)C1(c2ccccc2)CCN(CCC[C@]2(c3ccc(Cl)c(Cl)c3)CCCN(C(=O)c3ccccc3)C2)CC1]

(iii) SB 218795—(Available from, for example, Tocris Bioscience); (R)-[[2-Phenyl-4-quinolinyl)carbonyl]amino]-methyl ester benzeneacetic acid

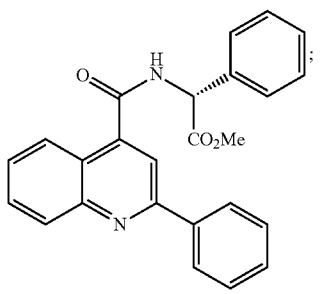 [SMILES: COC(=O)[C@H](NC(=O)c1cc(-c2ccccc2)nc2ccccc12)c1ccccc1]

(iv) SSR 146977 HCl (Available from, for example, Tocris Bioscience); N1-[1-3-[(3R)-1-Benzoyl-3-(3-(3,4-dichlorophenyl)-3-piperidinyl]propyl]-4-phenyl-piperidinyl]-N,N-dimethylurea hydrochloride

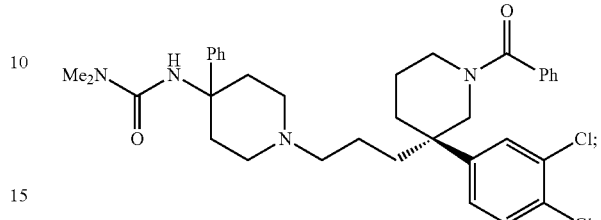

(v) AZD2624—(Astra Zeneca)

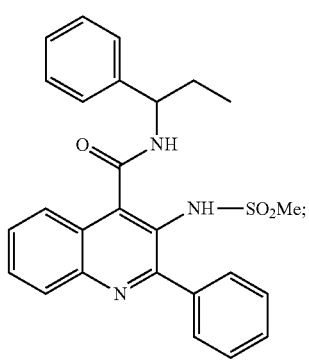

AZD2624 and (vi) Talnetant (SB 223412) (Available from, for example, MedChem Express); (S)-N-(1-phenylpropyl)-3-hydroxy-2-phenylquinoline-4-carboxamide

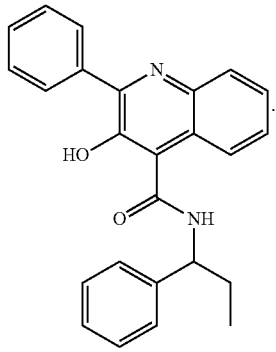 [SMILES: CCC(NC(=O)c1c(O)c(-c2ccccc2)nc2ccccc12)c1ccccc1]

In another embodiment, the compound comprises a neurokinin type 1 receptor antagonist (NK1R). Substance P acts on KNDy neurons through NK1R to amplify their activity, and likewise, NK1R antagonists block KNDy neuronal activity.

The term "antagonist" refers to a compound that can bind to NK1R but has little or no functional activity of its own at the receptor—thus disrupting, blocking or otherwise interfering with the action of the naturally occurring, endogenous ligand (Substance P). An antagonist may' be a ligand that directly binds to the receptor. Alternatively, an antagonist may combine with a receptor indirectly by, for example, (a) forming a complex with another molecule that directly binds to the receptor, or (b) otherwise results in the modification of another compound so that the other compound directly binds to the NK1R. In other embodiments, the term "antagonist" may include "inverse agonists", which bind to NK1R and inhibit constitutive activity.

Any suitable NK1R antagonist can be used, including but not limited to (or stereoisomers, mixture of stereoisomers, prodrugs, pharmaceutically acceptable salts, hydrates, solvates, acid salt hydrates, N-oxides and isomorphic crystalline forms thereof):

(i) SR140333/Nolpitantium (Available from, for example, Tocris Bioscience) 1-[2-[(3S)-3-(3,4-Dichlorophenyl)-1-[2-[3-(1-methylethoxy)phenyl]acetyl]-3-piperidinyl]ethyl]-4-phenyl-1-azoniabicyclo[2.2.2]octane chloride (peripherally restricted)

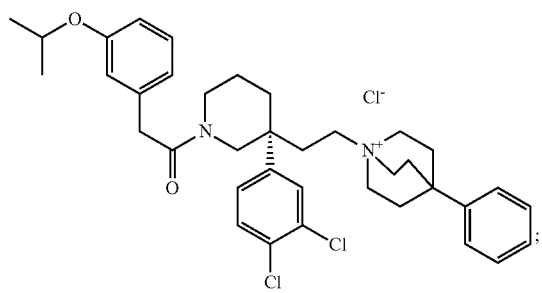 [SMILES: CC(C)Oc1cccc(CC(=O)N2CCC[C@](CC[N+]34CCC(c5ccccc5)(CC3)CC4)(c3ccc(Cl)c(Cl)c3)C2)c1 ; [Cl-]]

(ii) L-733,060 hydrochloride (Available from, for example, Tocris Bioscience) (2S,3S)-3-[[3,5-bis(Trifluoromethyl)phenyl]methoxy]-2-phenylpiperidine hydrochloride

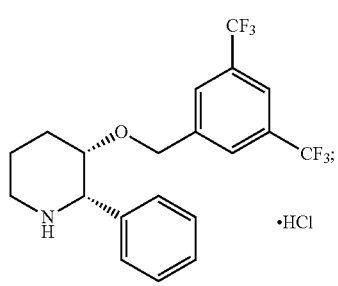 [SMILES: FC(F)(F)c1cc(CO[C@H]2CCCN[C@H]2c2ccccc2)cc(C(F)(F)F)c1 ; Cl]

(iii) CP 96345: (Available from, for example, Tocris Bioscience) (2S,3S)-N-(2-Methoxyphenyl)methyl-2-diphenylmethyl-1-azabicyclo[2.2.2]octan-3-amine

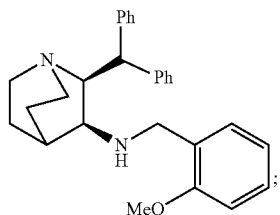 [SMILES: COc1ccccc1CN[C@H]1C2CCN(CC2)[C@H]1Cc1ccccc1 ; "Ph"]

(iv) Aprepitant: 5-([[(2R,3S)-2-((R)-1-[3,5-bis(trifluoromethyl)phenyl]ethoxy)-3-(4-fluorophenyl)morpholino]methyl)-1H-1,2,4-triazol-3(2H)-one (Merck, CO)

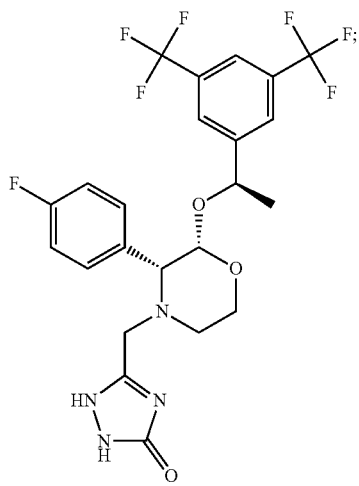 [SMILES: C[C@@H](O[C@@H]1OCCN(Cc2nc(=O)[nH][nH]2)[C@@H]1c1ccc(F)cc1)c1cc(C(F)(F)F)cc(C(F)(F)F)c1]

(v) RP 67580 (Available from, for example, Tocris Bioscience): (3aR,7aR)-Octahydro-2-[1-imino-2-(2-methoxyphenyl)ethyl]-7,7-diphenyl-4H-isoindol

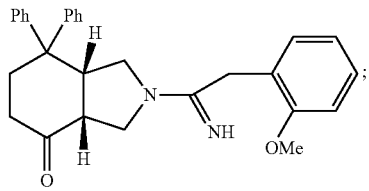 [SMILES: COc1ccccc1CC(=N)N1C[C@@H]2C(=O)CCC(c3ccccc3)(c3ccccc3)[C@@H]2C1]

(vi) RPR-100893/dapitant (Rhone-Poulenc)

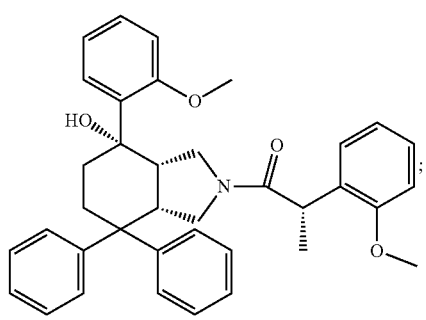 [SMILES: COc1ccccc1[C@H](C)C(=O)N1C[C@@H]2[C@H](C1)C(c1ccccc1)(c1ccccc1)CC[C@@]2(O)c1ccccc1OC]

(vii) CP-122721; [(+)-(2S,3S)-3-(2-methoxy-5-trifluoromethoxybenzyl)amino-2-phenylpiperidine];

(viii) CJ-11974/ezlopitant (Pfizer): (2S,3S)-2-benzhydryl-N-[(5-isopropyl-2-methoxy-phenyl)methyl]quinuclidin-3-amine;

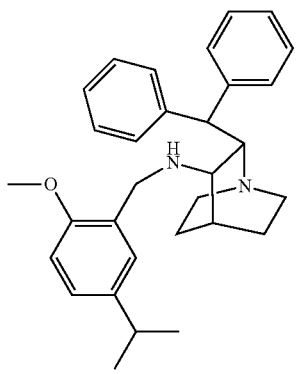 [SMILES: COc1ccc(C(C)C)cc1CNC1C2CCN(CC2)C1C(c1ccccc1)c1ccccc1]

(ix) L-754,274 (Merck);

(x) GR-203040: (Available from, for example, Sigma Aldrich) ((2S,3S)-2-methoxy-5-tetrazol-1-yl-benzyl-(2-phenyl-piperidin-3-yl)-amine) (CAS Number 168398-02-5);

(xi) GR-205171/vofopitant (Glaxo) (Available from, for example, BOC Sciences); CAS 168266-51-1; synonyms (a) 2S,3S)-N-{2-Methoxy-5-[5-(trifluoromethyl)-1H-tetrazol-1-yl]benzyl}-2-phenyl-3-piperidinamine dihydrochloride; (b)—Piperidinamine, N-[[2-methoxy-5-[5-(trifluoromethyl)-1H-tetrazol-1-yl]phenyl]methyl]-2-phenyl-, (2S,3S)-; (c)—Piperidinamine, N-[[2-methoxy-5-[5-(trifluoromethyl)-1H-tetrazol-1-yl]phenyl]methyl]-2-phenyl-, (2S-cis)-

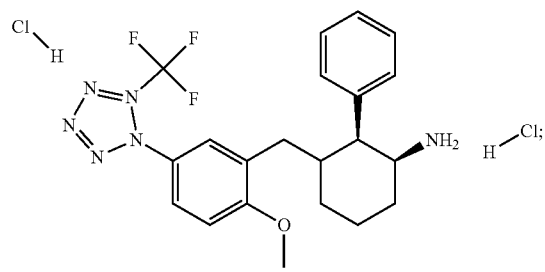

(xii) LY-303870/lanepitant (Eli Lilly): (R)-N-[2-[Acetyl[3H3][(2-methoxyphenyl)-methyl]amino]-1-(1H-indol-3-ylmethyl)ethyl][1,4'-bipiperidine]-1'-acetamide

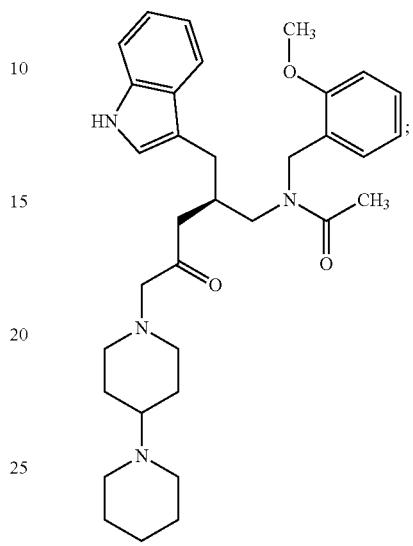

(xiii) CP 99994 (Available from, for example, Tocris Bioscience): (2S,3S)-N-[(2-Methoxyphenyl)methyl]-2-phenyl-3-piperidinamine dihydrochloride

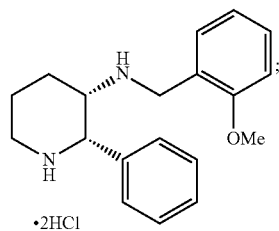 [SMILES: COc1ccccc1CN[C@H]1CCCN[C@H]1c1ccccc1]

(xiv) FK 888 (Available from, for example, Tocris Bioscience): (4R)-4-Hydroxy-1-[(1-methyl-1H-indol-3-yl)carbonyl]-L-prolyl-N-methyl-3-(2-naphthalenyl)-N-(phenylmethyl)-L-alaninamide

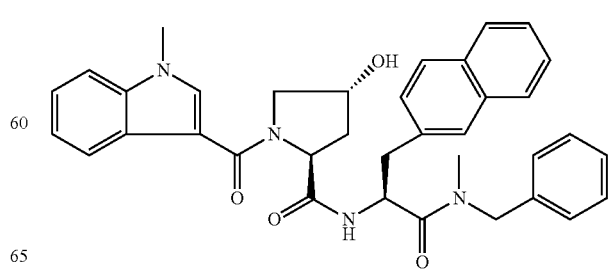

(xv) GR 82334: (Available from, for example, Tocris Bioscience):

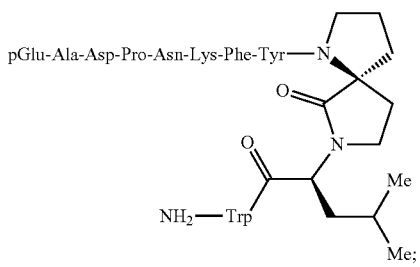

(xvi) L 760735 (Available from, for example, Tocris Bioscience): 5-[(2R,3S)-2-[(1R)-1-[3,5-Bis(trifluoromethyl) phenyl]ethoxy]-3-(4-fluorophenyl)-4-morpholinyl] methyl-N,N-dimethyl-1H-1,2,3-triazole-4-methanamine hydrochloride

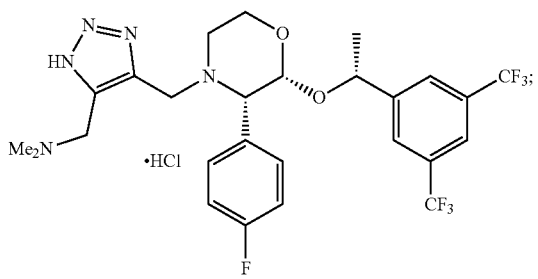 [SMILES: C[C@@H](O[C@H]1OCCN(Cc2nn[nH]c2CN(C)C)[C@H]1c1ccc(F)cc1)c1cc(C(F)(F)F)cc(C(F)(F)F)c1 ; Cl]

(xvii) L-732,138 (Available from, for example, Tocris Bioscience): N-Acetyl-L-tryptophan 3,5-bis(trifluoromethyl) benzyl ester

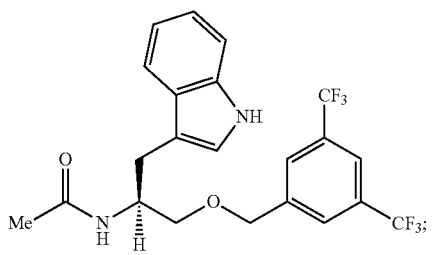

(xviii) SDZ NKT 343 (Available from, for example, Tocris Bioscience): 1-[[(2-Nitrophenyl)amino]carbonyl]-L-prolyl-N-methyl-3-(2-naphthalenyl)-N-(phenylmethyl)-L-alaninamide

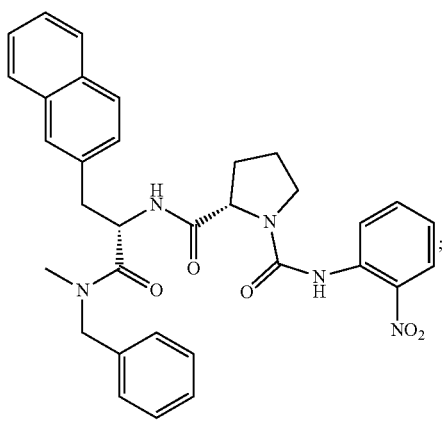 [SMILES: CN(Cc1ccccc1)C(=O)[C@H](Cc1ccc2ccccc2c1)NC(=O)[C@@H]1CCCN1C(=O)Nc1ccccc1[N+](=O)[O-]]

and (xix) Spantide I (Available from, for example, Tocris Bioscience): [D-Arg$^1$,D-Trp$^{7,9}$,Leu$^{11}$]-Substance P.

In one embodiment, the methods may combine use of two or more compounds selected from the group consisting of kappa agonists, NK3R antagonists, and NK1R antagonists. Thus, in a further aspect, the present invention comprises a pharmaceutical composition, comprising:

(1) two or more of a kappa agonist, an NK3R antagonist, an NK1R antagonist, or salts thereof; and (2) a pharmaceutically acceptable carrier.

The kappa agonist, NK3R antagonist, and/or NK1R antagonist for use in the compositions of the invention can be any suitable for a given purpose, including but not limited to any that are disclosed above for use in the methods of the invention. In one embodiment is the compounds are peripherally restricted.

Optionally, the compounds for use in the methods of the invention (or the pharmaceutical compositions of the invention) can be administered in combination with a second agent, including but not limited to hormone therapy. In one non-limiting embodiment, the short term estrogen therapy (2-3 months, for example) could be administered to block VMS, followed by kappa agonist treatment to hold the VMS down.

"Pharmaceutically acceptable" means approved or approvable by a regulatory agency of the federal or state government, or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained. The term "pharmaceutically acceptable salt" of a compound means a salt that is pharmaceutically acceptable and that possesses the desired pharmacological activity of the parent compound. Such salts include, for example, acid addition salts and base addition salts.

In certain aspects, the present disclosure provides for a pharmaceutical composition comprising the compounds of the present disclosure together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, and the like.

The term "pharmaceutically acceptable vehicle" refers to a diluent, adjuvant, excipient or carrier with which a compound of the present disclosure is administered. "Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. In addition, antioxidants and suspending agents can be used.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990). Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like. The present disclosure includes a pharmaceutical composition comprising a compound of the present disclosure including isomers, racemic or non-racemic mixtures of isomers, or pharmaceutically acceptable salts or solvates thereof together with one or more pharmaceutically acceptable carriers, and optionally other therapeutic and/or prophylactic ingredients.

In general, the compounds are administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present disclosure for a given, disease.

Thus, the compounds can be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is intravenous or oral (or alternative mucosal delivery, such as vaginal or nasal routes) using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: poly cations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compounds of the present disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Thus, for example, capsules can be prepared by conventional procedures so that the dosage unit is 100 mg of the compounds of the present disclosure, 100 mg of cellulose and 10 mg of magnesium stearate. A large number of unit capsules can also prepared by filling standard two-piece hard gelatin capsules each with 100 mg of powdered active ingredient, 150 mg of lactose, 50 mg of cellulose, and 10 mg magnesium stearate. Or, tablets can be prepared by conventional procedures so that the dosage unit is 100 mg of the compounds of the present disclosure, 150 mg of lactose, 50 mg of cellulose and 10 mg of magnesium stearate. A large number of tablets can also be prepared by conventional procedures such that the dosage unit was 100 mg of the compounds of the present disclosure, and other ingredients can be 0.2 mg of colloidal silicon dioxide, 5 mg of magnesium stearate, 250 mg of microcrystalline cellulose, 10 mg of starch and 100 mg of lactose. Appropriate coatings can be applied to increase palatability or delay absorption.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the present disclosure into, the body of a patient through a needle or a catheter, propelled by a sterile syringe or some other mechanical device such as an continuous infusion system. A formulation provided by the present disclosure can be administered using a syringe, injector, pump, or any other device recognized in the art for parenteral administration.

Sterile injectable suspensions can be formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained. Preparations according to the present disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

The formulations can optionally contain an isotonicity agent. The formulations preferably contain an isotonicity agent, and glycerin is the most preferred isotonicity agent. The concentration of glycerin, when it is used, is in the range known in the art, such as, for example, about 1 mg/mL to about 20 mg/mL.

The pH of the parenteral formulations can be controlled by a buffering agent, such as phosphate, acetate, TRIS or L-arginine. The concentration of the buffering agent is preferably adequate to provide buffering of the pH during storage to maintain the pH at a target pH±0.2 pH unit. The preferred pH is between about 7 and about 8 when measured at room temperature.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) can optionally be added to the formulation, and can be useful if the formulations will contact plastic materials. In addition, the parenteral formulations can contain various antibacterial and antifungal agents, for example, parabens, chlorobutanol, phenol, sorbic acid, thimerosal, and the like.

Sterile injectable solutions can be prepared by incorporating one or more of the compounds of the present disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the present disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

Pharmaceutical compositions for use in the methods of the invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and non-sensitizing.

Formulations for buccal administration include tablets, lozenges, gels and the like. Alternatively, buccal administration can be effected using a transmucosal delivery system as known to those skilled in the art. The compounds of the present disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compounds of the present disclosure can be formulated for aerosol administration, particularly to the respiratory tract and including intranasal administration. The compound will generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In other aspects, the present disclosure provides for kits that can be used to perform the methods described herein. In various aspects, the kits comprise the compounds of the present disclosure in one or more containers. In some aspects, the kits contain all of the components necessary and/or sufficient to administer the compounds of the present disclosure to a subject, including instructions for administering the compounds.

REFERENCES

1. Pachman D R, Jones J M, Loprinzi C L 2010 Management of menopause-associated vasomotor symptoms: Current treatment options, challenges and future directions. Int J Women Health 2:123-135.
2. Reed S D, Newton K M, LaCroix A Z, Grothaus L C, Ehrlich K 2007 Night sweats, sleep disturbance, and depression associated with diminished libido in late menopausal transition and early postmenopause: baseline data from the Herbal Alternatives for Menopause Trial (HALT). Am J Obstet Gynecol 196:593.e1-7; discussion 593.e7.
3. Deecher D C, Dorries K 2007 Understanding the pathophysiology of vasomotor symptoms (hot flushes and night sweats) that occur in perimenopause, menopause, and postmenopause life stages. Arch Womens Ment Health 10:247-257.
4. Freedman R R 2005 Pathophysiology and treatment of menopausal hot flashes. Semin. Reprod Med 23:117-125.
5. Sturdee D W 2008 The menopausal hot flush—anything new? Maturitas 60:42-49.
6. Maclennan A H, Broadbent J L, Lester S, Moore V 2004 Oral oestrogen and combined oestrogen/progestogen therapy versus placebo for hot flushes. Cochrane Database Syst Rev CD002978.
7. Notelovitz M, Lenihan J P, McDermott M, Kerber I J, Nanavati N, Arce J 2000 Initial 17beta-estradiol dose for treating vasomotor symptoms. Obstet Gynecol 95:726-731.
8. Utian W H, Archer D F, Bachmann G A, Gallagher C, Grodstein F, Heiman J R, Henderson V W, Hodis H N, Karas R H, Lobo R A, Manson J E, Reid R L, Schmidt P J, Stuenkel C A 2008 Estrogen and progestogen use in postmenopausal women: July 2008 position statement of The North American Menopause Society. Menopause 15:584-602.
9. 2005 National Institutes of Health State-of-the-Science Conference statement: management of menopause-related symptoms. Ann Intern Med 142:1003-1013.
10. Rossouw J E, Anderson G L, Prentice R L, LaCroix A Z, Kooperberg C, Stefanick M L, Jackson R D, Beresford S A, Howard B V, Johnson K C, Kotchen J M, Ockene J 2002 Risks and benefits of estrogen plus progestin in healthy postmenopausal women: principal results From the Women's Health Initiative randomized controlled trial. JAMA 288:321-333.
11. Carpenter J S, Neal J G 2005 Other complementary and alternative medicine modalities: acupuncture, magnets, reflexology, and homeopathy. Am J Med 118 Suppl 12B: 109-117.
12. Loprinzi C L, Dueck A C, Khoyratty B S, Barton D L, Jafar S, Rowland K M J, Atherton P J, Marsa G W, Knutson W H, Bearden J Dr, Kottschade L, Fitch T R 2009 A phase III randomized, double-blind, placebo-controlled trial of gabapentin in the management of hot flashes in men (NOOCB). Ann Oncol 20:542-549.
13. Mom C H, Buijs C, Willemse P H, Mourits M J, de Vries E G 2006 Hot flushes in breast cancer patients. Crit Rev Oncol Hematol 57:63-77.
14. Nachtigall L E 2010 Therapy: nonhormonal treatment of hot flashes—a viable alternative? Nat Rev Endocrinol 6:66-67.

15. Sideras K, Loprinzi C L 2010 Nonhormonal management of hot flashes for women on risk reduction therapy. J Natl Compr Canc Netw 8:1171-1179.
16. Freedman R R 2005 Hot flashes: behavioral treatments, mechanisms, and relation to sleep. Am J Med 118 Suppl 12B:124-130.
17. Meld=DR, Shamonki I M, Frumar A M, Tataryn I V, Chang R J, Judd H L 1979 Elevations in skin temperature of the finger as an objective index of postmenopausal hot flashes: standardization of the technique. Am J Obstet Gynecol 135:713-717.
18. Tataryn I V, Meldrum D R, Lu K H, Frumar A M, Judd H L 1979 LH, FSH and skin temperaure during the menopausal hot flash. J Clin Endocrinol Metab 49:152-154.
19. Gottsch M L, Cunningham M J, Smith J T, Popa S M, Acohido B V, Crowley W F, Seminara S, Clifton D K, Steiner R A 2004 A role for kisspeptins in the regulation of gonadotropin secretion in the mouse. Endocrinology 145:4073-4077.
20. Han S K, Gottsch M L, Lee K J, Popa S M, Smith J T, Jakawich S K, Clifton D K, Steiner R A, Herbison A E 2005 Activation of gonadotropin-releasing hormone neurons by kisspeptin as a neuroendocrine switch for the onset of puberty. J Neurosci 25:11349-11356.
21. Keen K L, Wegner F H, Bloom S R, Ghatei M A, Terasawa E 2008 An increase in kisspeptin-54 release occurs with the pubertal increase in luteinizing hormone-releasing hormone-1 release in the stalk-median eminence of female rhesus monkeys in vivo. Endocrinology 149:4151-4157.
22. Navarro V M, Gottsch M L, Chavkin C, Okamura H, Clifton D K, Steiner R A 2009 Regulation of gonadotropin-releasing hormone secretion by kisspeptin/dynorphin/neurokinin B neurons in the arcuate nucleus of the mouse. J Neurosci 29:11859-11866.
23. Roseweir A K, Kauffman A S, Smith J T, Guerriero K A, Morgan K, Pielecka-Fortuna J, Pineda R, Gottsch M L, Tena-Sempere M, Moenter S M, Terasawa E, Clarke I J, Steiner R A, Millar R P 2009 Discovery of potent kisspeptin antagonists delineate physiological mechanisms of gonadotropin regulation. J Neurosci 29:3920-3929.
24. Smith J T, Cunningham M J, Rissman E F, Clifton D K, Steiner R A 2005 Regulation of Kiss1 gene expression in the brain of the female mouse. Endocrinology 146:3686-3692.
25. Wakabayashi Y, Nakada T, Murata K, Ohkura S, Mogi K, Navarro V M, Clifton D K, Mori Y, Tsukamura H, Maeda K, Steiner R A, Okamura H 2010 Neurokinin B and dynorphin A in kisspeptin neurons of the arcuate nucleus participate in generation of periodic oscillation of neural activity driving pulsatile gonadotropin-releasing hormone secretion in the goat. J Neurosci 30:3124-3132.
26. Benarroch E E 2007 Thermoregulation: recent concepts and remaining questions. Neurology 69:1293-1297.
27. Maeda K-I, Ohkura S, Uenoyama Y, Wakabayashi Y, Oka Y, Tsukamura H, Okamura H 2010 Neurobiological mechanisms underlying GnRH pulse generation by the hypothalamus. Brain Res 1364:103-15.
28. Ohkura S, Takase K, Matsuyama S, Mogi K, Ichimaru T, Wakabayashi Y, Uenoyama Y, Mori Y, Steiner R A, Tsukamura H, Maeda K I, Okamura H 2009 Gonadotrophin-releasing hormone pulse generator activity in the hypothalamus of the goat. J Neuroendocrinol 21:813-821.
29. Gallo R V 1990 Kappa-opioid receptor involvement in the regulation of pulsatile luteinizing hormone release during early pregnancy in the rat. J Neuroendocrinol 2:685-691.
30. Gilbeau P M, Hosobuchi Y, Lee N M 1986 Dynorphin effects on plasma concentrations of anterior pituitary hormones in the nonhuman primate. J Pharmacol Exp Ther 238:974-977.
31. Kinoshita F, Nakai Y, Katakami H, Imura H 1982 Suppressive effect of dynorphin-(1-13) on luteinizing hormone release in conscious castrated rats. Life Sci 30:1915-1919.
32. Zhen S, Gallo R V 1992 The effect of blockade of kappa-opioid receptors in the medial basal hypothalamus and medial preoptic area on luteinizing hormone release during midpregnancy in the rat. Endocrinology 131:1650-1656.
33. Ambach G, Palkovits M, Szentagothai J 1976 Blood supply of the rat hypothalamus. IV. Retrochiasmatic area, median eminence, arcuate nucleus. Acta Morphol Acad Sci Hung 24:93-119.
34. Palkovits M 2008 Stress-induced activation of neurons in the ventromedial arcuate nucleus: a blood-brain-CSF interface of the hypothalamus. Ann N Y Acad Sci 1148:57-63.
35. Shaver S W, Pang J J, Wainman D S, Wall K M, Gross P M 1992 Morphology and function of capillary networks in subregions of the rat tuber cinereum. Cell Tissue Res 267:437-448.
36. Ramaswamy S, Seminara S B, Ali B, Ciofi P, Amin N A, Plant T M 2010 Neurokinin B stimulates GnRH release in the male monkey (*Macaca* mulatta) and is colocalized with kisspeptin in the arcuate nucleus. Endocrinology 151:4494-4503.
37. Charig C R, Rundle J S 1989 Flushing. Long-term side effect of orchiectomy in treatment of prostatic carcinoma. Urology 33:175-178.
38. Engstrom C 2005 Hot flash experience in men with prostate cancer: a concept analysis. Oncol Nurs Forum 32:1043-1048.
39. Karling P, Hammar M, Varenhorst E 1994 Prevalence and duration of hot flushes after surgical or medical castration in men with prostatic carcinoma. J Urol 152:1170-1173.
40. Ruka K A, Burger L L, Moenter S M. Regulation of arcuate neurons coexpressing kisspeptin, neurokinin B, and dynorphin by modulators of neurokinin 3 and κ-opioid receptors in adult male mice. Endocrinology 2013, August; 154(8):2761-71. doi: 10.1210/en. 2013-1268.
41. de Croft S, Boehm U, Herbison A E. Neurokinin B activates arcuate kisspeptin neurons through multiple tachykinin receptors in the male mouse. Endocrinology 2013, August; 154(8):2750-60. doi: 10.1210/en. 2013-1231.

EXAMPLES

Below are examples of specific embodiments for carrying out the present disclosure. The examples are offered for illustrative purposes only, and are not intended to limit the scope of the present disclosure in any way.
1. Animal Studies Confirm Efficacy of a PRKA to Block GnRH/LH Secretion The deleterious effects associated with an acute loss of circulating estradiol during the perimenopausal transition towards menopause include an inability to properly thermoregulate and therefore an inability to maintain a comfortable body temperature in the majority of women. The inability of perimenopausal women to thermoregulate properly is characterized by uncomfortable vasomotor symptoms (VMS) including debilitating hot flashes followed by chills, sweating and facial flushing. These VMS contribute to sleep disruptions, irritability, anxiety and low mood. Although estrogen therapy (ET) effectively reduces the occurrence and severity of uncomfortable VMS, ET can pose significant health risks. Therefore, we sought to investigate alternative therapies involving peripherally-restricted kappa agonists (PRKAs), which pose little/no side effects. Although the factors that initiate the uncomfortable VMS during the acute loss of circulating estradiol are not well understood, estrogen-sensitive circuits in the brain clearly play a role—the estrogen-sensitive neurocircuitry of the arcuate nucleus (ARC) within the hypothalamus is a possible therapeutic target of PRKAs. Hot flashes in women occur in coincidence with pulsatile LH secretion; pulsatile LH release and the temporally-matched menopausal VMS may be governed by the same specialized neurons within the ARC—these specialized neurons co-express kisspeptin, neurokinin B (NKB), type 3 NKB receptors (NK3R), dynorphin, and substance P (so-called KNDy neurons). KNDy neurons also express estrogen receptor alpha (ERα) and are inhibited by estradiol.

We thus tested whether kappa opioid receptor agonists could be used to treat hot flashes. We aimed to establish whether PRKA administration decreases circulating LH levels in mice, a first step in establishing whether this agent would likely act to inhibit KNDy neurons in menopausal women to alleviate menopausal VMS.

Materials and Methods
Animals

Female mice (000664 C57BL/6J) were obtained from The Jackson Laboratory (Sacramento, Calif., USA) at 8 weeks of age. All animals were housed on a 12:12-h light-dark cycle (lights off at 1800) with food and water available ad libitum. All experiments were conducted in accordance with the National Institutes of Health (NIH) Animal Care and Use Guidelines and with approval of the Animal Care and Use Committee of the University of Washington.

Ovariectomies

Mice were ovariectomized 13 days prior to the experiment, which occurred at approximately 11 weeks of age. Mice were anesthetized with isoflurane and bilaterally ovariectomized (OVX). Briefly, the animal's ventral skin was shaved and cleaned, and small incisions were made in the skin and abdominal musculature. The gonads were identified and excised, the abdominal muscle was sutured, and the skin incision was closed with surgical clips.

Treatments and Experimental Design

Mice were injected i.p. (<500 µl) with vehicle [0.9% sterile saline (Hospira, Lake Forest, Ill., USA) with 3.6% sterile DMSO (Sigma Aldrich, Inc., St. Louis, Mo., USA), n=7] or the following doses of the PRKA, ICI204,448 hydrochloride (Tocris Bioscience, Bristol, UK), diluted in sterile saline/DMSO: 0.1 mg/kg (0.018% DMSO, n=6), 1 mg/kg (0.18% DMSO, n=4), 10 mg/kg (1.8% DMSO, n=5), or 20 mg/kg (3.6% DMSO, n=7). N.B. 1 mg/kg and 10 mg/kg groups run in different experiment/assay. To assess the effects of ICI204,448 hydrochloride on LH secretion, blood samples were obtained 10 minutes prior to and 20 minutes after injection. Blood collections were obtained via retroorbital bleeding (□250 µl) of animals under isoflurane anesthesia. Blood was centrifuged and the serum stored at −20° C. until it was assayed for LH via radioimmunoassay.

Results

Figure 2:
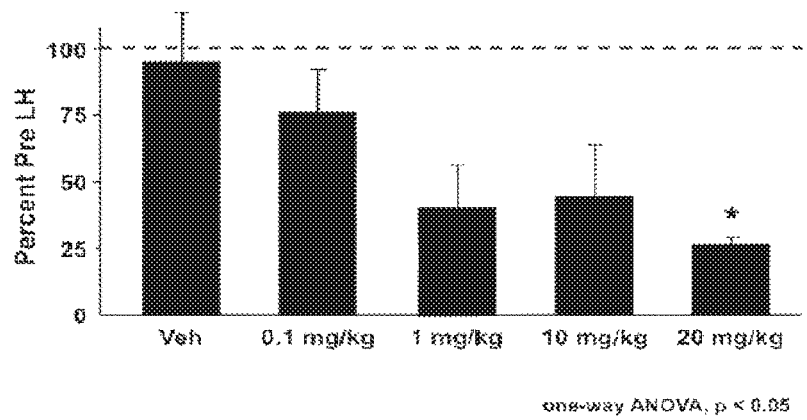
FIG. 2 is a graph showing an ICI-induced dose-dependent decrease in LH secretion in mice. N.B. 1 mg/kg and 10 mg/kg in different experiment/assay.

We injected 3 groups of ovariectomized mice (n=6-7/group) with the PRKA, ICI 204,448 hydrochloride (Tocris), i.p. as a High Dose (20 mg/kg), Low Dose (0.1 mg/kg), or saline Vehicle. Blood samples were taken ten minutes before and 20 minutes after injection. A 2-way repeated measures analysis of variance of LH yielded a significant treatment× time interaction (P<0.05), and a Bonferroni Post-hoc test revealed that post injection, LH was significantly decreased in the High Dose group vs. both Low Dose and Vehicle groups (P<0.01 and P<0.001, respectively). (See FIG. 2) These results suggest that KNDy neurons are a target of PRKAs and provide proof of concept for utilizing such agents for a treatment of VMS in perimenopausal women.

2. Using Kappa-Opioid Agonists to Treat Vasomotor Symptoms of Menopause: Results from Rodent and Human Studies Many kappa ligands including dynorphin have complicated central effects on the brain: dysphoria, analgesia, stress-relief effects (14-16). Such side effects make these agents less than ideal for long-term use to control hot flashes. Thus, a peripherally-restricted kappa-opioid receptor agonist that would have access to the arcuate (infundibular) nucleus, which lies outside the blood brain barrier, could be especially effective for treating hot flashes. Such an agent would restrict activity of the kisspeptin neurons, but avoid cognitive and extraneous undesirable effects of kappa ligands on the central nervous system (CNS). Thus, our first objective was to test the ability of one of these agents (ICI 204,448 HCl) to block LH secretion in mice (see Example 1), as proof of principle that such a technique could inhibit kisspeptin neuronal activity, and thereby block hot flashes. Unfortunately, none of the peripherally-restricted kappa agonists are approved for clinical use. However, there are some other types of kappa agonists that are approved for clinical use, including Talwin Nx (pentazocine+naloxone). Talwin Nx does cross the blood brain barrier and may have a psychotomimetic effect (17). However, this compound could still have value for obtaining proof of principle that inhibiting arcuate (infundibular) kisspeptin neurons can limit hot flashes. We administered Talwin Nx in a short-term in-patient setting to women suffering hot flashes and measured its ability to attenuate hot flashes.

Results
Talwin Nx in Human
Methods and Experimental Design

Women ages 45-60, >6 months amenorrheic, with ≥6 mod-severe daily hot flashes were recruited and gave full consent to participate in a double-blind study to test the effects of a kappa agonist (pentazocine) on the frequency of hot flashes (subjectively reported and verified by skin conductance changes). Ten women were given oral placebo, 50/0.5 mg or 25/0.25 mg pentazocine/naloxone, each therapy randomly assigned to be taken on 3 separate days over 8 hours. Skin conductance was objectively-measured using the Bahr monitor. Analyses were performed using Friedman ANOVA.

Radioimmunoassays (RIA)

All hormone assays were performed in duplicate by the University of Virginia Ligand Assay Laboratory (Charlottesville, Va.). Mouse LH Sandwich: Reportable Range: 0.04-37.4 ng/mL, intra-assay coefficient of variation (CV) is 5% (2 assays). N.B. 1 mg/kg and 10 mg/kg groups run in different assay. All of the women had circulating levels of FSH and estradiol (E2) indicative of menopause: FSH>30 mIU/mL, with an average value of 81.5±9.5 mIU/mL (reportable range: 0.1-170 mIU/mL); all women had E2 levels under 17 pg/nL, with 8 out of 9 women below the detectable limit of the assay (reportable range: 12.3-1700.0 pg/nL).

Figure 3:
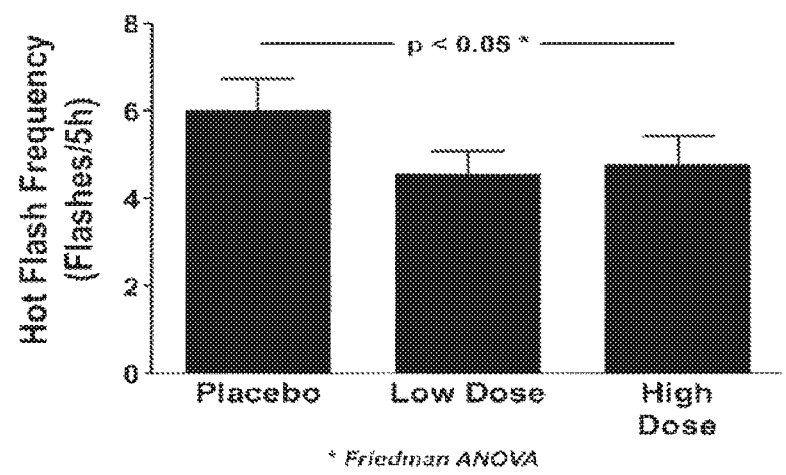
FIG. 3 is a graph showing the effects of an oral administration of pentazocine plus naloxone (TalwinNx) on the frequency of hot flashes in menopausal women (measured over a period of 6 hours following oral ingestion), showing the ability of a kappa agonist (pentazocine) to inhibit hot flashes.

Pentazocine and naloxone had modest, yet significant effect on limiting the frequency of hot flashes (approximately a 20% reduction; see FIG. 3). The main side effect was nausea. Addition of naloxone can be presumed to have exerted no significant effects following oral administration since the dose is biologically inert. Naloxone was added to oral version of agent to prevent its abuse as an i.v. substance of abuse.

REFERENCES FOR EXAMPLE 2

1. R. F. Casper, S. S. Yen, *Clin Endocrinol (Oxf)* 22, 293 (1985).
2. J. Gambone et al., *J Clin Endocrinol Metab* 59, 1097 (1984).
3. K. A. Guerriero, K. L. Keen, R. P. Millar, E. Terasawa, *Endocrinology* 153, 825 (2012).
4. M. A. Mittelman-Smith et al., *Endocrinology* 153, 2800 (2012).
5. R. L. Goodman et al., *Endocrinology* 153, 5918 (2012).
6. H. K. Choe et al., *Proc Natl Acad Sci USA* 110, 5677 (2013).
7. K. L. Keen, F. H. Wegner, S. R. Bloom, M. A. Ghatei, E. Terasawa, *Endocrinology* 149, 4151 (2008).
8. S. Ohkura et al., *J Neuroendocrinol* 21, 813 (2009).
9. V. M. Navarro et al., *J Neurosci* 29, 11859 (2009).
10. V. M. Navarro et al., *Am J Physiol Endocrinol Metab* 300, E202 (2011).
11. Y. Wakabayashi et al., *J Neurosci* 30, 3124 (2010).
12. P. Mostari et al., *J Reprod Dev* 59, 266 (2013).
13. T. Nakahara et al., *J Reprod Dev* 59, 479 (2013).
14. J. V. Aldrich, J. P. McLaughlin, *AAPS J* 11, 312 (2009).
15. M. F. Peters et al., *Eur J Pharmacol* 661, 27 (2011).
16. J. L. Ryan et al., *J Endod* 34, 552 (2008).
17. J. Q. Swift, K. M. Hargreaves, *Compendium* 14, 1048, 1050 passim; quiz 1060 (1993).
18. S. L'Esperance, S. Frenette, A. Dionne, J. Y. Dionne, *Support Care Cancer* 21, 1461 (2013).
19. A. Sarkissian, J. O. Neher, R. Singh, L. St Arma, *J Fam Pract* 61, 759 (2012).
20. A. M. Rometo, S. J. Krajewski, M. L. Voytko, N. E. Rance, *J Clin Endocrinol Metab* 92, 2744 (2007).

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure. Accordingly, the disclosure is not limited.

We claim:

1. A method for treating or limiting the development of one or more vasomotor symptoms (VMS) in a female menopausal patient in need thereof, comprising administering estrogen to the patient for two to three months followed by treatment with an effective amount of osanetant, or a stereoisomer, mixture of stereoisomers, prodrug, pharmaceutically acceptable salt, hydrate, solvate, acid salt hydrate, N-oxide or isomorphic crystalline form thereof.

* * * * *